US012797394B2

(12) United States Patent
Ricchetti et al.

(10) Patent No.: US 12,797,394 B2
(45) Date of Patent: Nov. 17, 2026

(54) MnTBAP AND M(III)N-SUBSTITUTED PYRIDYLPORPHYRINS(MnPS)FOR USE IN REVERSING SEPSIS-INDUCED MICROGLIAL CELLS ALTERATIONS AND/OR FOR TREATING SEPSIS OR SEPSIS-ASSOCIATED ENCEPHALOPATHY

(71) Applicants: INSTITUT PASTEUR, Paris Cedex (FR); CENTRE NATIONAL DE LA RECHERCHE SCIENTIFIQUE, Paris Cedex (FR); ASSISTANCE PUBLIQUE—HOPITAUX DE PARIS, Paris Cedex (FR); UNIVERSITE PARIS CITE, Paris (FR); GROUPE HOSPITALIER UNIVERSITAIRE PARIS—PSYCHIATRIE ET NEUROSCIENCES, Paris Cedex (FR)

(72) Inventors: Miria Ricchetti, Paris (FR); Fabrice Chretien, Paris (FR); Franck Verdonk, Paris (FR); Laurent Arnaud Chatre, Paris (FR)

(73) Assignees: INSTITUT PASTEUR, Paris (FR); CENTRE NATIONAL DE LA RECHERCHE SCIENTIFIQUE, Paris (FR); ASSISTANCE PUBLIQUE—HOPITAUX DE PARIS, Paris (FR); UNIVERSITE PARIS CITE, Paris (FR); GROUPE HOSPITALIER UNIVERSITAIRE PARIS—PSYCHIATRIE ET NEUROSCIENCES, Paris (FR)

( * ) Notice: Subject to any disclaimer, the term of this patent is extended or adjusted under 35 U.S.C. 154(b) by 493 days.

(21) Appl. No.: 18/547,437

(22) PCT Filed: Mar. 18, 2022

(86) PCT No.: PCT/EP2022/057224
§ 371 (c)(1),
(2) Date: Aug. 22, 2023

(87) PCT Pub. No.: WO2022/195100
PCT Pub. Date: Sep. 22, 2022

(65) Prior Publication Data

US 2024/0148749 A1 May 9, 2024

(30) Foreign Application Priority Data

Mar. 18, 2021 (EP) .................................... 21305335

(51) Int. Cl.
*A61K 31/555* (2006.01)
*A61P 25/28* (2006.01)

(52) U.S. Cl.
CPC ............ *A61K 31/555* (2013.01); *A61P 25/28* (2018.01)

(58) Field of Classification Search
CPC .................................................... A61K 31/555
See application file for complete search history.

(56) References Cited

FOREIGN PATENT DOCUMENTS

| | | | | |
|---|---|---|---|---|
| WO | 95/31197 A1 | | 11/1995 | |
| WO | WO95/31197 | * | 11/1995 | A61K 31/40 |
| WO | 2009/052411 A2 | | 4/2009 | |
| WO | WO2009/052411 | * | 4/2009 | A61K 31/40 |
| WO | 2020/055929 A1 | | 3/2020 | |
| WO | WO2020/055929 | * | 3/2020 | A61K 31/40 |

OTHER PUBLICATIONS

Mckinnon et al. , Microcirculation (2007) vol. 14, pp. 697-707.*
McKinnon et al. Ascorbate Inhibits Reduced Arteriolar Conducted Vasoconstriction in Septic Mouse Cremaster Muscle, Microcirculation, 2007, 14(7), 697-707.

* cited by examiner

*Primary Examiner* — Paul V Ward
(74) *Attorney, Agent, or Firm* — Arrigo, Lee, Guttman & Mouta-Bellum LLP

(57) ABSTRACT

The invention relates to MnTBAP or Mn(III) substituted pyridylporphyrin (MnP) compounds selected among MnTE-2-pYP5+, MnTEHex-2-Pyp5+ and MnTnBuOE-2-Pyp5+ for use in treating sepsis and/or reversing sepsis-induced microglial cells alteration(s), and/or reversing associated long-term cognitive impairment in a subject diagnosed with sepsis or sepsis-associated encephalopathy (SAE), and/or treating long-term cognitive impairment in a subject suffering from sepsis or sepsis-associated encephalopathy (SAE).

17 Claims, 16 Drawing Sheets

Figures 1A, 1B, 1C:
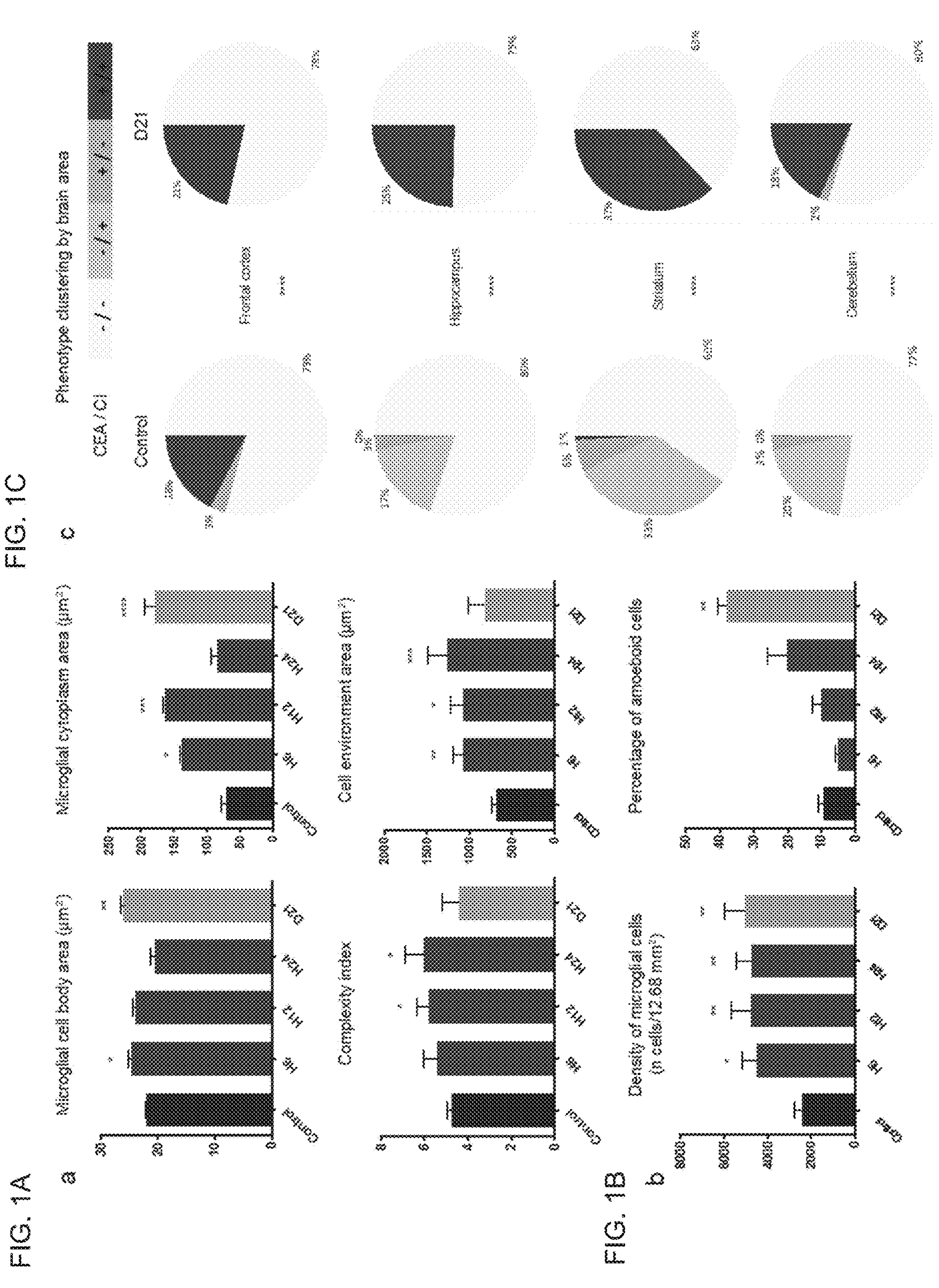

Specification includes a Sequence Listing.

a
Microglial cell body area (µm²)
Complexity index
Microglial cytoplasm area (µm²)
Cell environment area (µm²)

b
Density of microglial cells (n cells/12.68 mm²)
Percentage of amoeboid cells
Control
H6
H12
H24
D21 c
Phenotype clustering by brain area
CEA / CI
- / -
- / +
+ / -
Control
D21
Frontal cortex
Hippocampus
Striatum
Cerebellum d b c d FIG. 3B
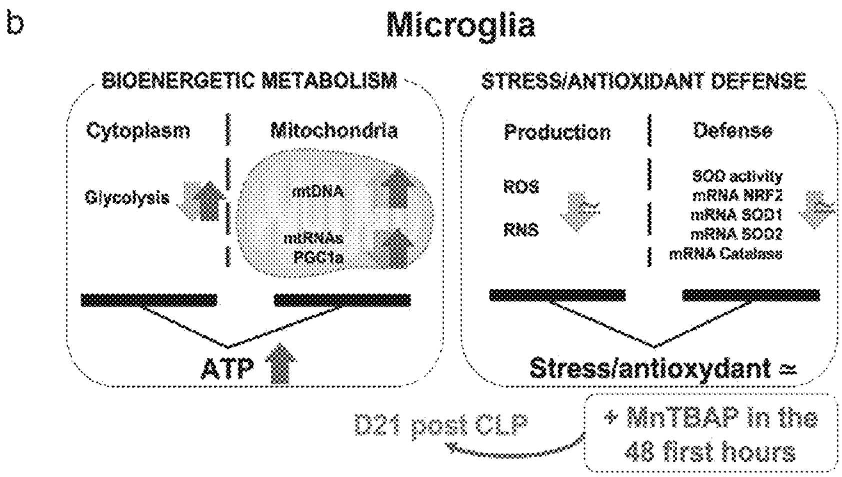
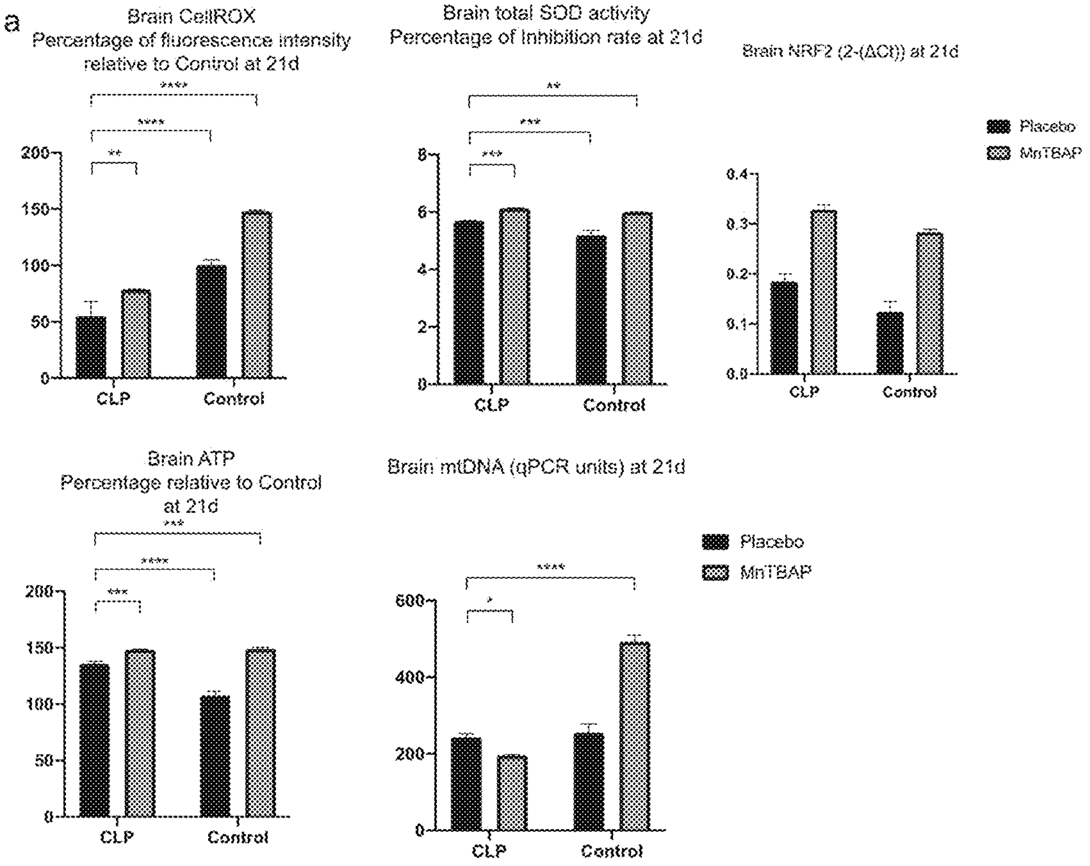
FIG. 4A a
Brain SOD1 expression (2-(ΔCt)) at 21d
Brain SOD2 expression (2-(ΔCt)) at 21d
Brain catalase expression (2-(ΔCt)) at 21d b
Brain Acetyl-CoA (nmol/g of proteins) at 21d
Brain PGC1alpha expression (2-(ΔCt)) at 21d c
Brain 16S rRNA expression (2-(ΔCt)) at 21d
Brain Cytochrome b expression (2-(ΔCt)) at 21d
CLP
Control
Placebo
MnTBAP

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Forward primer Mouse TBP

<400> SEQUENCE: 1

cttcaccaat gactcctatg                                                20


<210> SEQ ID NO 2
<211> LENGTH: 20
<212> TYPE: DNA
<213> ORGANISM: Artificial Sequence
<220> FEATURE:
<223> OTHER INFORMATION: Reverse primer Mouse TBP
```

<400> SEQUENCE: 2
tgactgcagc aaatcgcttg 20

<210> SEQ ID NO 3
<211> LENGTH: 21
<212> TYPE: DNA
<213> ORGANISM: Artificial Sequence
<220> FEATURE:
<223> OTHER INFORMATION: Forward primer Mouse Catalase or Mouse NRF2

<400> SEQUENCE: 3
agagagcgga ttcctgagag a 21

<210> SEQ ID NO 4
<211> LENGTH: 21
<212> TYPE: DNA
<213> ORGANISM: Artificial Sequence
<220> FEATURE:
<223> OTHER INFORMATION: Reverse primer Mouse Catalase or Mouse NRF2

<400> SEQUENCE: 4
acctttccct tggagtatct g 21

<210> SEQ ID NO 5
<211> LENGTH: 21
<212> TYPE: DNA
<213> ORGANISM: Artificial Sequence
<220> FEATURE:
<223> OTHER INFORMATION: Forward primer Mouse SOD1

<400> SEQUENCE: 5
ggacctcatt ttaatcctca c 21

<210> SEQ ID NO 6
<211> LENGTH: 19
<212> TYPE: DNA
<213> ORGANISM: Artificial Sequence
<220> FEATURE:
<223> OTHER INFORMATION: Reverse primer Mouse SOD1

<400> SEQUENCE: 6
tgcccaggtc tccaacatg 19

<210> SEQ ID NO 7
<211> LENGTH: 21
<212> TYPE: DNA
<213> ORGANISM: Artificial Sequence
<220> FEATURE:
<223> OTHER INFORMATION: Forward primer Mouse SOD2

<400> SEQUENCE: 7
cagacctgcc ttacgactat g 21

<210> SEQ ID NO 8
<211> LENGTH: 19
<212> TYPE: DNA
<213> ORGANISM: Artificial Sequence
<220> FEATURE:
<223> OTHER INFORMATION: Reverse primer Mouse SOD2

<400> SEQUENCE: 8
ctcggtggcg ttgagattg 19

<210> SEQ ID NO 9

<211> LENGTH: 18
<212> TYPE: DNA
<213> ORGANISM: Artificial Sequence
<220> FEATURE:
<223> OTHER INFORMATION: Forward primer Mouse PGC1A (Pprgc1a)

<400> SEQUENCE: 9
ggacagtctc cccgtgat 18

<210> SEQ ID NO 10
<211> LENGTH: 18
<212> TYPE: DNA
<213> ORGANISM: Artificial Sequence
<220> FEATURE:
<223> OTHER INFORMATION: Reverse primer Mouse PGC1A (Pprgc1a)

<400> SEQUENCE: 10
tccatctgtc agtgcatc 18

<210> SEQ ID NO 11
<211> LENGTH: 20
<212> TYPE: DNA
<213> ORGANISM: Artificial Sequence
<220> FEATURE:
<223> OTHER INFORMATION: Forward primer Mouse 16S rRNA

<400> SEQUENCE: 11
gggactagca tgaacggcta 20

<210> SEQ ID NO 12
<211> LENGTH: 20
<212> TYPE: DNA
<213> ORGANISM: Artificial Sequence
<220> FEATURE:
<223> OTHER INFORMATION: Reverse primer Mouse 16S rRNA

<400> SEQUENCE: 12
ccccaaccga aatttcaaac 20

<210> SEQ ID NO 13
<211> LENGTH: 20
<212> TYPE: DNA
<213> ORGANISM: Artificial Sequence
<220> FEATURE:
<223> OTHER INFORMATION: Forward primer Mouse CYTB

<400> SEQUENCE: 13
acgtccttcc atgaggacaa 20

<210> SEQ ID NO 14
<211> LENGTH: 20
<212> TYPE: DNA
<213> ORGANISM: Artificial Sequence
<220> FEATURE:
<223> OTHER INFORMATION: Reverse primer Mouse CYTB

<400> SEQUENCE: 14
gaggtgaacg attgctaggg 20

<210> SEQ ID NO 15
<211> LENGTH: 19
<212> TYPE: DNA

-continued

<213> ORGANISM: Artificial Sequence
<220> FEATURE:
<223> OTHER INFORMATION: Forward primer Mouse NDUFV1

<400> SEQUENCE: 15
cttccccact ggcctcaag 19

<210> SEQ ID NO 16
<211> LENGTH: 20
<212> TYPE: DNA
<213> ORGANISM: Artificial Sequence
<220> FEATURE:
<223> OTHER INFORMATION: Reverse primer Mouse NDUFV1

<400> SEQUENCE: 16
ccaaaaccca gtgatccagc 20

<210> SEQ ID NO 17
<211> LENGTH: 19
<212> TYPE: DNA
<213> ORGANISM: Artificial Sequence
<220> FEATURE:
<223> OTHER INFORMATION: Forward primer Mouse CO1

<400> SEQUENCE: 17
tgctagccgc aggcattac 19

<210> SEQ ID NO 18
<211> LENGTH: 20
<212> TYPE: DNA
<213> ORGANISM: Artificial Sequence
<220> FEATURE:
<223> OTHER INFORMATION: Reverse primer Mouse CO1

<400> SEQUENCE: 18
ggtgcccaaa gaatcagaac 20

MnTBAP AND M(III)N-SUBSTITUTED PYRIDYLPORPHYRINS(MnPS)FOR USE IN REVERSING SEPSIS-INDUCED MICROGLIAL CELLS ALTERATIONS AND/OR FOR TREATING SEPSIS OR SEPSIS-ASSOCIATED ENCEPHALOPATHY

The present invention pertains to the field of therapies aimed at assisting recovery of sepsis especially in severe forms, in particular where brain, neurologic or cognitive damage(s) is(are) at stake. The invention more particularly concerns therapies also seeking, or further seeking, to alleviate short and/or long term symptoms or complications related to the occurrence of a septic episode in a subject, especially brain, neurologic or cognitive symptoms or complications.

The invention relates to a therapy for reversing sepsis-induced microglial cells alteration(s), and/or associated long-term cognitive impairment.

The invention also relates to methods of treatment, in particular methods for treatment and/or alleviation of symptoms or complications of sepsis as defined herein, and to means, especially particular substances/compounds or compositions encompassing the same, for use in these methods.

The invention is of particular interest in the context of treatment of a subject having sepsis, or displaying symptom (s) thereof, in particular, but not only, when brain dysfunction is found. In particular, the present invention is aimed at controlling the outcome of sepsis as defined herein by improving the outcome of the sepsis episode, thereby constituting a rescue therapy. The present invention is also aimed, alone or in combination with the preceding, at alleviating short and/or long term symptoms, complications, and/or conditions related to the occurrence of a septic episode, as further detailed herein. This can encompass treatment or alleviation or attenuation of psychocognitive or cognitive disorders, brain dysfunction, and brain oxidative damage, even after the sepsis episode has resolved. In this respect, the invention is also aimed at preventing late cognitive defects or attenuating foreseeable cognitive function deficit, or improving cognitive function in sepsis survivors, when administration of active ingredient as defined herein is made after the onset of a septic event, in a subject in need thereof. According to a particular aspect, administration of active ingredient as defined herein can be performed in the early period of sepsis development.

Sepsis results from a systemic inflammatory response that is triggered by infection and can induce multiple organ failure. Sepsis represents a major worldwide public health issue associated with increased short-and long-term morbidity, and mortality ranging from 21% to 38% in ICU (ProCESS Investigators et al., 2014; Vincent et al., 2019; Rudd et al., 2020) and up to 48% in survivors one year later (Prescott et al., 2018; Courtright et al., 2020). Sepsis is defined as life-threatening organ dysfunction caused by a dysregulated host response to infection (Singer et al., 2016). Because sepsis is a major cause of mortality in intensive care units, early recognition or diagnosis is recommended for attempting sepsis management. It is considered that focused management, which does nevertheless not constitute a dedicated therapy, may improve the outcomes in sepsis. Actions to be taken can be administration of antibiotics and of intravenous fluids to obtain adequate blood pressure or blood supply to organs. Other monitoring actions may involve blood cultures, lactate and hemoglobin determination, urine output monitoring, and high-flow oxygen provision. Nevertheless, among the organ failure in acute phases, a sepsis-associated encephalopathy (SAE) occurs in up to 80% of cases (Hosokawa et al., 2014) and is characterized by a disorder of consciousness ranging from delirium to coma (Gofton and Young, 2012). SAE is associated with increased risk of mortality and long-term cognitive impairment and psychological disorders (Pandharipande et al., 2014; Iwashyna et al., 2010b; Heming et al., 2017; Prescott and Angus, 2018), as part of a "post-sepsis syndrome" (Mostel et al., 2019). The pathophysiology of this syndrome remains non-elucidated but might involve innate immune cells reprogramming (van der Slikke et al., 2020). Within the brain, microglial cells contribute to both innate and adaptive immune brain responses and are involved in the maintenance of brain homeostasis (Ginhoux et al., 2013). Their activation is promoted by systemic inflammation in the sepsis setting (Annane and Sharshar, 2015a) and can lead either to persistent neuro-inflammation which is described up to 14 days after sepsis induction in rodent models (Zaghloul et al., 2017) or to a "primed" microglial state that contributes to the pathogenesis of neurodegenerative disease (Perry and Holmes, 2014; Cunningham et al., 2009). Different mechanisms may underlie this phenomenon such as long-term epigenetic and immunological endotypes changes, but recently cellular metabolism impairments are also evoked (Manfredini et al., 2019). Brain tissue has unique characteristics that make it more susceptible to mitochondrial dysfunction and oxidative stress associated with sepsis (Bozza et al., 2013). These metabolic alterations could contribute to long-term impairment, as it is suggested by recent studies involving activation of brain biogenesis (Manfredini et al., 2019) or mitochondrial transplantation (Yan et al., 2020) to improve cognition 10 days after in murine models of sepsis.

As stated in [Guerreiro MO, Petronilho F, Andrades M, Constantino L, et al. 2010], several molecular mechanisms of inflammation and cellular damage have been implicated in the pathogenesis of sepsis, including those related to the generation of cytokines, eicosanoids, and reactive oxygen species (ROS). ROS are believed to be important mediators of cellular injury, contributing to the development of multiple organ failure and mortality in sepsis. In this context, antioxidants have been used in animal models of sepsis, but no clear benefit was demonstrated in humans.

However, as of now, long-term microglial changes following sepsis resolution and their relationship with cognitive impairment have not been characterized. Using a multiscale approach in a murine model of sepsis, from metabolic to functional levels, it is described herein the deciphering of microglial alterations at early (from 6 to 24 hours) and late (21 days) time points after sepsis. From these experiments, it could be hypothesized that long-term cognitive dysfunction results from a mitochondrial dysfunction of the microglial cells, induced by circulating reactive oxygen species (ROS) and reactive nitrogen species (RNS). To address this hypothesis, it is reported herein the cognitive, cellular and metabolic reactions to early injection of ROS/RNS modulator superoxide dismutase (SOD) mimetic (Liu et al., 2013a; Chatre et al., 2015), the synthetic metalloprophyrin Manganese(III)tetrakis (4-benzoic acid) porphyrin (MnTBAP).

In fact, there is currently no effective, especially dedicated, treatment against sepsis in humans, and especially no treatment aimed at addressing either one or both between 1/the immediate consequences (of a sepsis episode or subsequent events, which range from death to severe symptoms, in a subject in need thereof, and 2/long-term complications, in particular long-term psychocognitive disorders, that can arise as a result. Immediate consequences can encompass death but also preceding organ dysfunction(s) and other consequences or symptoms as further detailed herein.

In particular, it remains a need to preserve patients from the damages, especially short or even more, long term damages, resulting from the occurrence of a septic episode, or at least reduce their extent and/or gravity.

Also, there is currently no effective treatment or protective strategy that would take into account the occurrence brain dysfunction, or its short or long term impact on the health status of a subject, following sepsis or the onset, in order to prevent and/or abolish or alleviate the risks associated therewith. Also, there is also currently no effective treatment or protective strategy, in particular neuroprotective, brain protective and/or cognitive function protective strategy, taking into account long-term complications, in particular long-term psychocognitive disorders that may arise following a septic episode.

There is also no treatment or protective strategy, in particular neuroprotective, brain protective and/or cognitive function protective strategy, taking into account a possible reversal of sepsis-induced microglial cells alteration(s), thereby having effect on associated long-term cognitive impairment, even at a distance of the sepsis event giving rise to said long-term cognitive impairment.

The present invention provides solutions to at least part of these needs. The inventors studied the impact of sepsis induced by CLP (cecal ligation puncture) at the i/clinical, ii/tissue and iii/cellular level in mice. As reported herein, using a mouse model of sepsis survival, it was found that 21 days after sepsis, microglial cells exhibit morphological and immunologic markers of activated and cytotoxic phenotypes combined with downregulation of both the nitroso-redox stress and the antioxidant defense, and a mitochondrial metabolic reprogramming. These microglial changes were associated with cognitive dysfunction and both reversed after intraperitoneal injection of a reactive oxygen/nitrogen species (ROS/RNS) modulator superoxide dismutase (SOD) mimetic (MnTBAP) within the early stages of sepsis. Administration of MnTBAP also significantly reduced mortality in septic mice.

These experiments, which are at the basis of the present invention, and their results, are further detailed hereafter.

From them, it could be assessed that sepsis-associated cognitive impairment is partly related to protracted metabolic-related microglial dysfunction, which results from systemic reactive oxygen/nitrogen species generated in the acute phase of sepsis. These findings provide new pathophysiological insights and of SAE and open new therapeutic perspectives.

The inventors provided evidence that a short treatment of septic mice, following sepsis onset, with a nitroso-redox stress scavenger at the systemic level, over a 48 h period of time after sepsis onset, was sufficient to reduce oxidative and nitrosative stress, protect the brain, highlighted by higher cognitive performance including in the long-term and, importantly, decrease the mortality of septic mice.

MnTBAP is known from patent application WO 2015/121459 to be a nitroso-redox stress scavenger compound capable of scavenging ROS species at the cellular level. It has been proposed to treat or delay Cockayne syndrome or symptoms thereof, and/or restore level(s) of particular protein(s), especially to treat or delay Cockayne syndrome. However, WO 2015/121459 is not concerned by therapies directed to sepsis or the consequences of such conditions.

The invention relates to a MnTBAP compound or a Mn(III) substituted pyridylporphyrin (MnP) compound according to any one of the following formula:

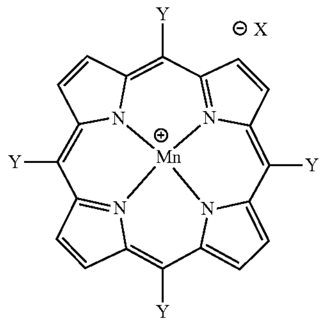

Where
Y is

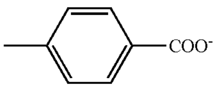
or
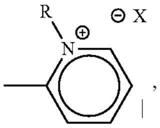
, and

R is selected amongst ethyl (MnTE-2-Pyp5+), n-hexyl (MnTEHex-2-Pyp5+) and n-butyl-$OCH_2CH_2$— (MnTnBuOE-2- Pyp5+), and X is an anion, and where the compound is for use:

i. in treating sepsis, in particular alleviating symptoms thereof, and/or preventing complications associated therewith, in particular complications susceptible to arise after sepsis resolution, and/or ii. reversing sepsis-induced microglial cells alteration(s), especially brain microglia, notably sepsis-induced metabolic reprogramming of microglia, more notably brain microglia, and/or reversing associated long-term cognitive impairment in a subject diagnosed with sepsis or sepsis-associated encephalopathy (SAE), and/or iii. treating long-term cognitive impairment in a subject suffering from sepsis or sepsis-associated encephalopathy (SAE), in particular where the compound is administered after the occurrence of a sepsis episode.

The skilled person is readily aware that X is any anion as appropriate, for example Cl, PF6, tosylate, besylate, mesylate, etc. . . . The medium in which the compound is found conventionally determines the anion.

By "sepsis", it is made reference to the updated definition published in "The Third International Consensus Definitions for Sepsis and Septic Shock (Sepsis-3)" (Singer et al., (23 Feb. 2016) JAMA. 315 (8): 801-10): sepsis is a life-threatening organ dysfunction caused by a dysregulated host response to an infection. Organ dysfunction can be identified using the so-called Sepsis-related Organ Failure Assessment score, also known as Sequential Organ Failure Assessment score (SOFA score), documented in Singer et al.: organ dysfunction may be considered present when an acute change in total SOFA score is equal or superior to 2 points consequent to an infection. Link is made to Box 3 and Table 1 of Singer et al., incorporated by reference and shown below, regarding the criteria/parameters to be assessed for determining a SOFA score.

| System | Score 0 | 1 | 2 | 3 | 4 |
|---|---|---|---|---|---|
| Respiration | | | | | |
| PaO2/FiO2, mm Hg (kPa) | ≥400 (53.3) | <400 (53.3) | >300 (40 | <20 (26.7) with respiratory support | <100 (13.3) with respiratory support |
| Coagulation | | | | | |
| Platelets, $10^3$/μL | ≥150 | <150 | <100 | <50 | <20 |
| Liver | | | | | |
| Bilirubin, mg/dL (μmol/L) | <1.2 (20) | 1.2-1.9 (20-32) | 2.0-5.9 (33-101) | 6.0-11.9 (102-204) | >12.0 (204) |
| Cardiovascular | MAP ≥70 mm Hg | MAP <70 mm Hg | Dopamine <5 or dobutamine (any dose)[b] | Dopamine 5.1-15 or epinephrine ≤0.1 or norepinephrine ≤0.1[b] | Dopamine <15 or epinephrine >0.1 or norepinephrine >0.1[b] |
| Central nervous system | | | | | |
| Glasgow Coma Scale score [c] | 15 | 13-14 | 10-12 | 6-9 | <6 |
| Renal | | | | | |
| Creatinine, mg/dL (μmol/L) | <1.2 (110) | 1.2-1.9 (110-170) | 2.0-3.4 (171-299) | 3.5-4.9 (300-440) | >5.0 (440) |
| Urine output, mL/d | | | | <500 | <200 |

Abbreviations:
FiO2, fraction of inspired Oxygen;
MAP, mean arterial pressure;
PaO2, partial pressure of oxygen
[b]Catecholmaine doses are given as μg/kg/min for at least one hour.
[c] Glasgow Coma Scale score range from 3-15; higher scores indicate better neurological function.

Since criteria for organ dysfunction like SOFA may require clinical and laboratory variables that may be missing or difficult to obtain in a timely manner, a simpler model termed Quick SOFA Score (quickSOFA or qSOFA) has been established, especially usable at the bedside, which uses only 3 clinical variables and has an acceptable predictive validity. The qSOFA simplifies the SOFA score by only including its 3 clinical criteria and by including "any altered mentation" instead of requiring a Glasgow Coma Scale score (GCS) 513. When assessing a qSOFA score, the following parameters are given the following scores:

Low blood pressure (SBP≤100 mmHg): 1

High respiratory rate (≥22 breaths/min): 1

Presence of altered mentation: 1.

The score ranges from 0 to 3 points. The presence of 2 or more qSOFA points near the onset of infection is associated with a greater risk of death or prolonged intensive care unit stay. These are outcomes that are more common in infected patients who may be septic than those with uncomplicated infection.

Accordingly, the present invention applies to subjects susceptible to be diagnosed as having sepsis or diagnosed as having entered a sepsis episode, accordingly to the definitions in the art. The invention thus also applies, according to a particular embodiment, to subjects engaged in an ongoing diagnosis protocol because suspected to be at risk of sepsis, but not yet diagnosed (which are therefore, according to a particular embodiment, subjects susceptible to be diagnosed as septic), or, according to another embodiment, to subjects diagnosed as having sepsis including in more severe forms thereof. Assessment of the presence of a sepsis episode including in more severe forms thereof can be made according to clinically relevant parameters, such as those which are indicated herein, although in a non-limitative way.

Biomarkers for sepsis status exist and may alternatively be used, although the definition of sepsis is clinical and follows the guidelines provided above. Some markers such as CRP and PCT have been evaluated for assisting the diagnosis (for a review see Pierrakos, C., Velissaris, D., Bisdorff, M. et al. Biomarkers of sepsis: time for a reappraisal. Crit Care 24, 287 (2020). https://doi.org/10.1186/s13054-020-02993-5).

According to a particular embodiment, the invention is concerned with the clinical situation where sepsis is associated with cognitive impairment (also: cognitive disorders and/or brain dysfunction), according to any situation or embodiment disclosed herein, and/or protracted metabolic-related microglial dysfunction, according to any situation or embodiment referring to microglial alterations, especially microglial cell alterations, as disclosed herein.

According to the above, presence of sepsis including in more severe forms thereof is preferably determined through scoring systems.

According to a particular embodiment, a compound is therapeutically administered:

a. to a subject with a suspected infection or presence of an infection which is still to be determined, having a quick SOFA score (qSOFA score) at least equal to 1 point, in particular equal to 2 or 3 points, or b. to a subject diagnosed as suffering from sepsis, said subject displaying symptom(s) corresponding to an acute change in total Sepsis-related Organ Failure Assessment score (SOFA score) equal or superior to 2 points subsequently to an infection.

Reference is made to Singer et al., 2016, discussed above, for complete guidance. SOFA variables encompass PaO2/FiO2 ratio, Glasgow Coma Scale score, Mean Arterial Pressure, Administration of vasopressors with type and dose rate of infusion, Serum creatinine or urine output, Bilirubin level and Platelet count. qSOFA variables encompass Respiratory rate, mental status and systolic blood pressure. Thresholds to be used for each parameter are reported in the table above, in Singer et al., 2016 which is incorporated by reference in its entirety, and herein.

These procedures are suitable to identify infected patients who are likely to be septic. The SOFA score is aimed at clinically characterizing a septic patient, in particular with the view of gathering data that can be compared in a clinical context. SOFA score can indeed be scored retrospectively. These tools provide guidance with respect to the identification, even post-identification, of patients susceptible to qualify as subjects suffering from sepsis. However, it will be understood that the present invention either applies to a subject diagnosed with sepsis according to any one of the procedure described above, or in the course of being diagnosed using such procedures, in the presence of a suspicion of sepsis.

According to a particular embodiment, when a qSOFA score is tested, one of the tested parameters is the mental status. According to a more particular embodiment, when the tested parameter (among others) is the mental status, the result of the test identifies the presence of a cognitive impairment in the tested subject.

According to a particular embodiment, when a SOFA score is tested, one of the tested parameters is the Glasgow Coma Scale score (GCS). According to a more particular embodiment, when the tested parameter (among others) is the Glasgow Coma Scale score (GCS), the result of the test identifies the presence of a cognitive impairment in the tested subject, in particular where the Glasgow Coma Scale score (GCS) is 513.

According to a particular embodiment, the patient is defined as presenting a protracted metabolic-related microglial dysfunction, as evaluated according to the common knowledge in the field and/or according to the guidance provided herein when assessing microglial metabolic status or determining the presence of "microglial cells alteration(s) or "morphological and/or immune alterations and/or metabolic reprogramming", according to the definitions provided herein.

According to a particular embodiment, administration is made to a subject diagnosed as being in a situation of septic shock and/or displaying altered mentation, in particular suffering from sepsis-associated encephalopathy.

Septic shock is defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia (see Singer et al. 2016, discussed above).

Sepsis-Associated Encephalopathy (SAE) can be defined as a symptom present in either sepsis or septic shock if the criteria for defining the latter are met, where mental alterations can be found. It is observed that the qSOFA scoring include mental status assessment in the limited set of paramters it uses. It can also be seen as a complication of sepsis since it may sequentially arise once a sepsis episode is entered. Altered mentation can be defined in this context as any Glasgow Coma Scale Score less than 15 (see Singer et al., 2016 discussed above).

As defined herein, "symptoms" accompany a sepsis episode, either suspected or diagnosed, in particular an ongoing sepsis episode. According to another aspect, "complications" are events that are susceptible to further worsen the clinical situation of the patient at either stage, even after a transitory improvement of its clinical situation. There may a short-term positive outcome and a resolved septic episode, with later stage complications arising at a later point of time, as it will be in particular discussed hereafter regarding cognitive dysfunction, especially long-term cognitive dysfunction(s) that can arise subsequently to a septic episode, at a later point of time.

According to a particular embodiment, symptoms of sepsis and/or complications of sepsis encompass one or several item(s) of the following list: systemic inflammation, oxidative damage, in particular brain oxidative damage, neuro-muscular disorder(s), microglial cells alteration(s) in particular morphological and/or immune alterations and/or metabolic reprogramming, especially microglia metabolic reprogramming, neuro-inflammation, behavioral impairment, cognitive dysfunction(s) or impairment, brains disorder(s) including neuromyopathy and/or sepsis-associated encephalopathy (SAE), and any combination thereof.

According to another aspect, which can be cumulative to a treatment or taken alone, the invention concerns the reversal of sepsis-induced microglial cells alteration(s), and/or reversal of associated long-term cognitive impairment in a subject diagnosed with sepsis or sepsis-associated encephalopathy (SAE).

By "microglial cells alteration(s) or "morphological and/or immune alterations and/or metabolic reprogramming" it is made reference to the fact shown herein that a sepsis event "impaired durably microglial cells or morphological and immunologic markers of activated and/or cytotoxic phenotypes combined with downregulation of both the nitroso-redox stress and a mitochondrial metabolic reprogramming". Therefore, "microglial cells alteration(s)" are synonym of and can be shown by one or more of:

a) the acquisition of morphological markers of activated and cytotoxic phenotypes by microglial cells, and/or
b) the acquisition of immunologic markers of activated and cytotoxic phenotypes by microglial cells, and/or
c) the downregulation of the nitroso-redox stress in microglial cells, and/or
d) change(s) in mitochondrial metabolism that amounts to a "reprogramming" because of their extent, as illustrated herein. Details of metabolic markers that can be followed are provided hereafter and in the experimental section.

Regarding a), the Results section herein shows in the paragraph "Sepsis induces long term morphological and phenotypic microglial alterations in survivors", "Cellular levels" that, for example, microglial cell morphology and density can be measured. This provides the skilled person with exemplary guidance regarding how to determine presence of microglial cells with activated and cytotoxic phenotypes, as also documented in the literature. The skilled person can thus readily define morphological markers for assessment of presence of "microglial cells alteration(s)" as required.

Regarding b), the Results section herein describes in the paragraph "Sepsis induces long term morphological and phenotypic microglial alterations in survivors", "Immunophenotype level" parameters involved in a cytotoxic microglial phenotype or in a neurotoxic microglial phenotype. Table 1 also describes measurable parameters, e.g., Quantification of pro-inflammatory markers (CD32, CD86 and Ptgs2 mRNA), anti-inflammatory markers (Lgals3, IGF1 and CD206 mRNA), immuno-regulator markers (IL1-RA, IL4-Rα and SOCS3 mRNA) and cytokine mRNA. The skilled person is therefore provided with exemplary guidance regarding immunologic markers of activated and cytotoxic phenotypes by microglial cell, so as to assess the presence of "microglial cells alteration(s)" as required, according to that criteria.

Regarding c), the paragraph "Sepsis induces lasting metabolic reprogramming in microglial cells" in the Results section herein describes that levels of two major reactive species, namely ROS H2O2 and RNS peroxynitrite, have been measured, as well as the expression of antioxidant defense genes NRF2 transcription factor, superoxide dismutases 1 and 2 (SOD1 and mitochondrial SOD2) and catalase, and SOD protein activity. Accordingly, the skilled person can readily assess downregulation of the nitroso-redox stress in microglial cells, using proposed parameters.

Regarding d), the paragraph "Sepsis induces lasting metabolic reprogramming in microglial cells" in the Results section herein describes that ATP production, Acetyl-Coa levels, metabolism markers (PGC1 alpha), mitochondrial DNA (mtDNA) and RNA (mtRNA) could be measured. Such metabolic data confirmed that sepsis induces from early stage to 21 days in survivors from sepsis a major metabolic reprogramming in microglial cells with ultimately a metabolic shift towards mitochondrial OXPHOS.

The skilled person can readily apprehend that the proposed parameters are by no means limitative, guidance can be found herein and in the literature in order to effect measurement of suitable parameters for assessing the presence of a microglial cells alteration(s) caused by sepsis, and conversely, reversal of the same.

According to a particular embodiment, microglial cells used for assessment, especially of the above parameters, of for assays in the context of the invention, are brain microglial cells.

The experimental section herein also provides guidance for determination of presence of cognitive impairment in a subject, and thus long-term cognitive impairment when measured at a later point of time after a sepsis episode that has resolved. The skilled person can thus perfectly assess whether reversal of long-term cognitive impairment is present.

As shown in the experimental section, reversal of sepsis-induced microglial cells alteration(s), especially microglial reprogramming, upon treatment according to the invention, went with reversal of cognition alterations.

According to another aspect, the invention also applies, in line with the experiments reported herein, to therapeutic situations where cognitive dysfunction(s) are found. Said cognitive dyfunction(s) as long-term impairment complication(s) can be alterations in memory, and/or alterations in attention, and/or alterations in concentration, and/or global loss of cognitive function. These can arise both at the sepsis stage or, as seen above, as part of long term consequence(s) after resolution of a sepsis episode.

According to another aspect, the invention relates to a compound for use according to embodiment described herein, wherein said compound acts as a neuroprotective, and/or brain protective, and/or cognitive function protective agent, in particular acts on microglia cell phenotype and/or metabolism, especially to induce a neuroprotective microglial phenotype. In a particular aspect, the said compound therapeutic effect is to induce a switch of microglial cells phenotype from a neurotoxic microglial phenotype to neuroprotective microglial phenotype upon treatment, especially on brain microglial cells.

According to a particular embodiment, said compound acts as a neuroprotective, and/or brain protective, and/or cognitive function protective agent as described in the above paragraph, at a certain distance in time of the sepsis event, i.e., prevents deleterious effects, as late complications of a sepsis event, on the cognition of the treated subject.

According to a particular embodiment, the invention relates a compound for use as described in any embodiment herein, for treating long-term cognitive impairment in a subject suffering from sepsis or sepsis-associated encephalopathy (SAE), in particular where the compound is administered after the occurrence of a sepsis episode, especially the occurrence of a sepsis episode as determined according to any embodiment described herein, and according to any administration regimen described herein.

According to a particular embodiment, the invention relates a compound for use as described in any embodiment herein, in the treatment of long-term cognitive impairment associated with a sepsis episode, through reversal treatment of sepsis-induced microglial cells alteration(s), wherein said compound is administered at an early stage, especially within the first 24 or 48 hours after onset or diagnosis, to a patient diagnosed or presenting symptoms of sepsis or sepsis-associated encephalopathy (SAE).

According to a particular embodiment, the invention relates a compound for use as described in any embodiment herein, in restoring long-term cognitive function after a sepsis episode, wherein said compound is administered at an early stage, especially within the first 24 or 48 hours after onset or diagnosis, to a patient diagnosed or presenting symptoms of sepsis or sepsis-associated encephalopathy (SAE).

According to a particular embodiment, the invention relates a compound for use as described in any embodiment herein, for use in treating or alleviating associated long-term cognitive impairment in a subject diagnosed with sepsis or sepsis-associated encephalopathy (SAE) through reversal treatment of sepsis-induced microglial cells alteration(s), wherein said compound is administered at an early stage, especially within the first 24 or 48 hours after onset or diagnosis to a patient diagnosed or presenting symptoms of sepsis or sepsis-associated encephalopathy (SAE).

According to a particular embodiment applicable throughout the description, an administration regime is as such: the compound is first administered to a subject in need thereof between the moment of sepsis onset and 48 hours, in particular 24 hours, after the moment of sepsis onset, or between the moment of the diagnosis of the sepsis episode and 48 hours, in particular 24 hours, after the diagnosis of the sepsis episode.

According to a particular embodiment applicable throughout the description, an administration regime is as such: the administration regime involves one or several dose administration(s) over time, in especially 2, or 3, or 4, or 5 dose administration(s), more especially administration of 4 doses successively administered every 12 hours starting at sepsis onset or from the diagnosis of sepsis for the first administration.

According to a particular embodiment applicable throughout the description, an administration regime is as such: the administration regime involves administration of 4 doses successively administered every 6 hours starting at sepsis onset or from the diagnosis of sepsis for the first administration.

By "treatment" or "therapeutic treatment", it is meant that the performed steps of administration result in improving the clinical condition of a subject in need thereof, who suffers from the condition(s) defined herein. Such treatment aims at improving the clinical status of the subject, especially animal or human patient, by eliminating or lowering or alleviating the symptoms associated with the condition(s) defined herein and/or in a particular embodiment, restoring to health.

According to a particular embodiment, it is meant by "treating sepsis" the fact of abolishing, or preventing, or decreasing the mortality associated with this condition, in an extent that the odds to survive to the sepsis are increased. In other words, the treatment of the invention can be defined as a rescue therapy. "Treatment" in the context of a sepsis is in particular aimed at controlling the outcome of said episode, by improving the chances to survive to the episode. According to a particular embodiment, a treatment according to the invention comes with 40%, or 50%, or 60%, or 70% reduction of the mortality rate for the treated subject.

As seen herein, according to a particular embodiment, it is also meant protecting the subject from more severe consequences, on its health status, of the treated condition, compared to the consequences that would arise in the absence of treatment. This includes eliminating or lowering or alleviating the symptoms associated with the condition(s) defined herein.

By "symptoms of sepsis" is meant symptoms associated with the onset of, or an established sepsis episode. These symptoms can be observed at various levels. At the biological level, symptoms can, non limitatively, encompass systemic inflammation, oxidative damage, in particular brain oxidative damage, neuro-muscular disorder(s), microglial cells alteration(s) including as defined herein, neuro-inflammation, behavioral impairment (such as locomotor activity impairement), cognitive dysfunction(s) or impairment, brains disorder(s) including neuromyopathy.and encephalopathy (also termed brain dysfunction herein, or sepsis-associated encephalopathy (SAE)). Symptoms can also be identified on the basis of the parameters used in a scoring system for diagnosing sepsis including in more severe forms thereof, as detailed above. Parameters observable at the tissue or cellular level, including biomarkers can accordingly be assessed in case such symptoms are not immediately visible to the eye.

"Symptoms" can be observed in a subject from the onset of the septic condition (initial or early symptoms), or during the course of the sepsis condition (ongoing symptoms), independently of a proper clinical diagnosis of the underlying condition. They accordingly can be observed during the course of sepsis. In other words, "symptoms" may be defined as short-term consequences of sepsis. The outcome of a sepsis episode, encompasses recovery or death and also complications.

According to a particular embodiment, combined with sepsis treatment, as defined herein, the invention is also directed to preventing complications associated with sepsis, in particular complications susceptible to arise after sepsis resolution.

By "complications associated with sepsis", or "complications associated with the prior occurrence of sepsis episode", it is conversely meant symptom(s), condition(s) or even disorder(s) or disease(s) occurring after the sepsis episode has resolved. According to a particular aspect, such complications may be later determined to be related to the prior occurrence of a sepsis episode in the subject. Accordingly, "complications" may be observed in sepsis survivors. "Complications", as defined herein, may encompass the "symptoms" listed above, the only difference being that they are observed after sepsis or inflammatory-related episode resolution. According to a particular aspect, "complications" refer to brain dysfunction(s) or disorder(s) that can be observed after the sepsis or inflammatory-related episode resolved. Survivors of sepsis or an inflammatory-related episode can present long-term cognitive impairment, including alterations in memory, attention, concentration, and global loss of cognitive function (long-term cognitive deficit). "Complications" may further include diseases that may later arise and be correlated with the occurrence of sepsis or inflammatory-related episode in the observed patient. For instance, emergence of chronic oxidative stress that can result from a sepsis, may promotes brain abnormalities and pathologies. For example, Langa et al. report in JAMA. 2010 Oct 27; 304(16): 1787-1794. doi: 10.1001/jama.2010.1553 that «Incident severe sepsis was associated with a clinically and statistically significant increase in moderate/severe cognitive impairment among survivors." And Tseng et al. report in Oncotarget. 2017 Oct 13; 8(48): 84300-84308, doi: 10.18632/oncotarget.20899 that "Septicemia is associated with increased risk for dementia".

By "treating symptoms thereof", it is meant eliminating, abolishing or lowering the symptoms defined herein, especially restoring health, so that health status of the subject can be considered as tending to or reversing to a healthy status.

By "alleviating symptoms thereof", it is meant alleviating the symptoms associated with the condition(s) defined herein.

By "treating or alleviating complications associated with sepsis", or "preventing complications associated with sepsis", it is meant abolishing, or lowering the complications as defined herein, or preventing the occurrence of said complications, as defined herein, so that health status of the surviving subject having suffered from the condition(s) defined herein can be considered as tending to or reversing to a healthy status.

In particular, by "alleviating symptoms thereof and/or complications associated therewith", which is also within the scope of the present disclosure, it is meant decreasing, lessening or diminishing the extent of said symptoms or complications, in the absence of reversion to normal, or protecting from a worsening of said symptoms or complications.

In sepsis, oxidative stress may result in both oxidative damage and an exacerbated inflammatory environment, the latter of which can in turn result in microglial cells activation, especially when the oxidative stress occurs in the brain (brain oxidative stress), and possibly neurodegeneration and/or neurological sequela on the short and/or long term.

Oxidative stress encompasses "nitroso-redox stress", which is defined as the alteration of the nitroso-redox balance. The nitroso-redox balance consists in the interaction between nitric oxide (NO) and reactive oxygen species (ROS) production. ROS are reactive species of oxygen (where the reactive molecule has atoms of oxygen). RNS (reactive nitroso species) are reactive species of nitrogen (where the reactive molecule has nitrogen atoms). Reactive species means that these are highly reactive molecules. The definition of ROS and RNS is well defined in the literature, and readily available to the skilled person. The nitroso-redox balance has relevant signaling function in the organism and its impairment may result in dysfunctions.

Presence at the cellular level of a nitroso-redox imbalance, that can in particular be assessed through detection and quantification of ROS and/or RNS species in fluid samples of an assayed subject, may therefore favour or be potentially responsible for brain and microglial cells alterations during sepsis, and thus, potentially be responsible for brain dysfunction, cognitive dysfunction, and/or neuro-damages, on the short or long term.

The compound known under its common name "MnT-BAP" is a nitroso-redox stress scavenger compound. By "nitroso-redox stress scavenger compound(s)", it is meant a compound having for functional achievement(s) to act on the nitroso-redox balance by scavenging one or, preferably both, amongst reactive oxygen species (ROS) and reactive nitrogen species (RNS). Such compounds may be antioxidant(s), in particular antioxidant(s) with a porphyrine core or moiety.

However, differently from antioxidants, that are numerous, the nitroso-redox stress scavengers are very rare. To be precise, no molecule to date can be considered only as antioxidant (anti-ROS) or only as anti-RNS (=anti-nitroso compound), as at a minimal levels each molecule also affects the other category. But the extent of the effect on the other category can be minimal or insignificant. When it is made reference to "nitroso-redox stress scavengers" in present description and as suited for use in present invention, it is meant molecules that have a significant activity on both categories. Thus, although some molecules may have nitroso-redox stress scavenger activities, MnTBAP remains unique for the extent of effect on both categories, and for this, it is considered a unique molecule with these capacities. The invention therefore also encompasses, as compounds of interest, Manganese [=Mn] porphyrine derivative(s) or analog(s), in particular MnTBAP derivative(s) or analog(s), that have for functional achievement(s) to act on the nitroso-redox balance by scavenging one or, preferably both, amongst reactive oxygen species (ROS) and reactive nitrogen species (RNS), especially according to any definition provided herein.

The skilled person can readily determine whether a compound is nitroso-redox stress scavenger having both the properties to scavenge ROS and RNS. The literature is replete with information in this regard: measurement of ROS and RNS species levels can thus readily be achieved in experimental setups by the skilled person. The experimental section of present application provides further guidance. ROS and RNS levels, as well as their balance ROS/RNS were assessed by the levels of two major reactive species, namely ROS $H_2O_2$ and RNS peroxynitrite. For example, use can be made of fluorogenic dyes such as those commercialized under the trademark CellROX™. Any agent enabling measurement of absolute or relative values of levels for these species, or species known to be associated with nitroso-redox stress and qualifying as nitroso-redox stress scavenger and meeting the conditions set herein, may be used.

In more detail, the levels of ROS and RNS can be assessed using standard technologies and kits like those based on the principle of DCFHDA (2',7'-Dichlorodihydrofluorescin diacetate, for instance Sigma-Aldrich) to assess prevalently ROS levels, and DHR123 (Dihydrorhodamine 123, for instance Sigma-Aldrich) to assess prevalently RNS.

More sophisticated techniques to identify ROS and RNS, which is also more specific than DCFHDA and DHR123, for instance using mass spectrometry can also be used.

Another possibility to measure ROS and/or RNS is not to assess them directly, but measure the effect they have on protein(s): ROS generate protein oxidation, RNS generate protein nitration. The global levels of protein oxidation (or carbonylation) can be detected using immunofluorescence or Western blots with appropriates antibodies: for protein carbonylation anti dinitrophenyl (DNP)-specific antibody (for instance byMerck Millipore) can be used after DNP treatment. For protein nitration the anti-3-nitrotyrosine-specific antibody (for instance Ref: A21285; Life Technologies/Invitrogen) can be used.

These technologies are not exhaustive, but provide the skilled person, as a subset of the information readily available in the literature, all necessary elements to determine whether Manganese [=Mn] porphyrine derivative(s) or analog(s), in particular MnTBAP derivative(s) or analog(s), scavenge one or, preferably both, amongst reactive oxygen species (ROS) and reactive nitrogen species (RNS).

It is said that a compound has anti-ROS activity when the observed decrease in ROS species level(s), especially $H_2O_2$ level, in a cell or a collection of cells as assayed, is more than 10%, 20, 30%, 40%, 50%, 60%, 70%, 80% or 90%, measured 2 to 6 hours after end of administration of the scavenger compound, by reference to a control, when measured in vitro.

It is said that a compound has anti-RNS activity when the observed decrease in RNS species level(s), especially peroxynitrite level, in a cell or a collection of cells as assayed, is more than 10%, 20, 30%, 40%, 50%, 60%, 70%, 80% or 90% measured 2 to 6 hours after end of administration of the scavenger compound, by reference to a control, when measured in vitro.

Preferably in the context of present invention, the reduction effect on the level of reactive species is observed for both ROS and RNS, to an extent of at least 10% (=remaining 90%), 20, 30%, 40%, 50%, 60%, 70%, 80% or 90% of level reduction measured 2 to 6 hours after end of administration of the scavenger compound, by reference to a control, when measured in vitro.

It is anticipated that the effect of administration of compound with anti-ROS and/or anti-RNS activity may be as long as up to 12 hours after end of treatment. Therefore, would ROS and RNS species levels be assayed from a sample drawn from a patient, in order to be representative of what happens in that patient (rather than from an in vitro experiment as envisioned above), then the duration of time indicated above for assessing the reduction of reactive species can reach up to 12 hours after end of compound administration. In the experiments reported herein, the inventors treated mice in the first 12 h after induction of sepsis. To see effect on sepsis, at least 24 h were necessary. However, for just assessing the reduction of ROS and RNS species (e.g., in cells, or in blood), a few hours (2-6 h) are enough. The skilled person will therefore understand that the above-mentioned durations of time are therefore indicative and not limitative, and can be readily adapted following the guidance provided herein.

Of note, as reported herein, changes in $H_2O_2$ and RNS peroxynitrite level also amount to changes in the microglial metabolic state.

MnTBAP pertains to the category of SOD mimetics (Superoxide Dismutase mimetics—SODm) and Peroxynitrite Scavenger(s), and is more particularly a Metalloporphyrin, even more particularly a Manganese Porphyrin. Actually, a stated above there are not at all many active ingredients having both anti-ROS and anti-RNS capacities (which determines altogether the nitroso-redox balance). Several MnTBAP derivatives exist, belonging to the family of MnTBAP, i.e., porphyrin derivatives, which can act as nitroso-redox stress scavengers and capture both ROS ans RNS species. Some are described hereafter and Manganese [=Mn] porphyrine derivative(s) or analog(s), in particular MnTBAP derivative(s) or analog(s), scavenging preferably both amongst reactive oxygen species (ROS) and reactive nitrogen species (RNS), and having functional achievement (s) to act on the nitroso-redox balance according to any definition provided herein by scavenging preferably both, amongst reactive oxygen species (ROS) and reactive nitrogen species (RNS), in particular to achieve a reduction effect on the level of reactive species to an extent of at least 10% (=remaining 90%), 20, 30%, 40%, 50%, 60%, 70%, 80% or 90% of level reduction for both ROS and RNS, also encompassed within present invention and description. The same can be used within any embodiment as otherwise described herein.

The MnTBAP compound and the further compounds encompassed in the chemical formula provided here below are molecules with high levels of anti-ROS/anti-RNS, which make them suited for instant invention.

According to a particular embodiment, MnTBAP or Mn(III) substituted pyridylporphyrin (MnP) compounds suited for instant invention have any one of the following formula:

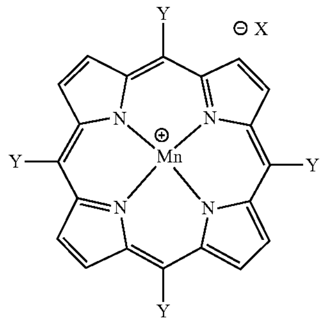

Where

Y is

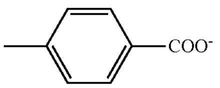

or

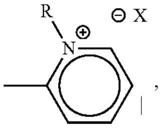

, and

R is selected amongst ethyl (MnTE-2-Pyp5+), n-hexyl (MnTEHex-2-Pyp5+) and n-butyl-$OCH_2CH_2$— (MnTnBuOE-2- Pyp5+), and X is an anion.

According to a particular embodiment, by MnTBAP, it is meant a compound having one of the formula (I) or (II):

(I)

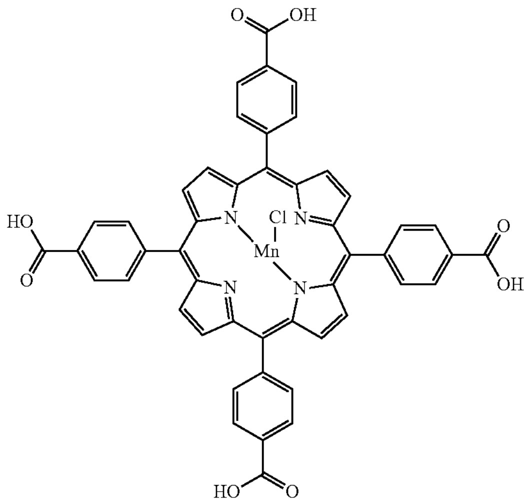

(II)

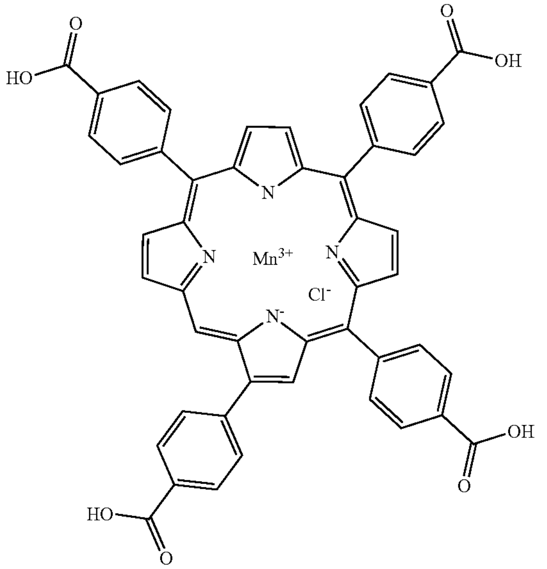

MnTBAP has the molecular formula C48H28ClMnN4O8 and encompasses compounds corresponding to the IUPAC name Chloro[4,4',4",4'"-(5,10,15,20-porphyrintetrayl-κ2N21,N23)tetrabenzoato(2-)]manganese or systematic names Chloro [4,4',4",4'"-(5,10,15,20-porphyrintetrayl-κ2N21,N23) tetrabenzoato(2-)] Manganese or Manganese (3+) chloride 5,10,15,20-tetrakis(4-carboxyphenyl)porphine-21,23-diide (1:1:1) or any one of the names Mn(III) meso-Tetra (4-carboxyphenyl) porphine chloride or Manganese(III)-tetrakis(4-benzoic acid)porphyrin or Mn(III) tetrakis(4-benzoic acid)porphyrin, or manganese [III] tetrakis (5, 10, 15, 20 benzoic acid) porphyrin, or Manganese (III) tetrakis (4-benzoic acid) porphyrin chloride or their equivalents depending on the nomenclature referred to for the name used.

MnTBAP can be found under its salt form (II) or as a complex (I) or mixtures thereof. Commercial preparations of MnTBAP exist that may contain MnTBAP with amounts of Mn-free ligand. Such preparations are also suitable for carrying out the present invention.

Other suitable compounds are termed MnTE-2-$Pyp^{5+}$, MnTnHex-2-$Pyp^{5+}$, and MnTnBuOE-2- $Pyp^{5+}$ herein.

$MnTE-2-Pyp^{5+}$, also termed manganese(III) 5,10,15,20-tetrakis(N-ethylpyridinium-2-yl) porphyrin or basically Mn(III) meso-tetrakis(N-ethyl-pyridinium-2-yl)porphyrin, is also known in the literature under abbreviations BMX-010, AEOL10113 and FBC007. Similarly to MnTBAP, $MnTE-2-Pyp^{5+}$, can be found under its salt form (with different oxidization levels) or as a complex or mixtures thereof.

Another compound of interest is $MnTnHex-2-Pyp^{5+}$, also termed manganese(III) 5,10,15,20-tetrakis(N-n-hexyl-pyridinium-2-yl) porphyrin or basically Mn(III) meso-tetrakis (N-n-hexylpyridinium-2-yl)porphyrin. Similarly to the other compounds, $MnTnHex-2-Pyp^{5+}$, can be found under its salt form (with different oxidization levels) or as a complex or mixtures thereof.

Another compound of interest is MnTnBuOE-2- $Pyp^{5+}$, also termed manganese(III) 5,10,15,20-tetrakis(N-n-butoxyethyl-pyridinium-2-yl) porphyrin or basically Mn(III) meso-tetrakis(N-n-butoxyethyl-pyridinium-2-yl)porphyrin, is also known in the literature under abbreviations BMX-001. Similarly to the other compounds, and MnTnBuOE-2- $Pyp^{5+}$, can be found under its salt form (with different oxidization levels) or as a complex or mixtures thereof.

As shown in the experimental section, it could be determined that appropriate attenuation of oxidative stress during sepsis can induce a beneficial effect at a distance of administration, more precisely in the long term, well after resolution of sepsis, especially on cognitive function. In other words, the administered MnTBAP compound has been shown to act as a neuroprotective agent to this end, especially under the circumstances described herein in particular through reversal sepsis-induced microglial cells alteration(s), when administered to septic mice.

"By neuroprotective agent", it is meant that the agent has beneficial effects, in particular compared to an absence of treatment, with respect to the "symptoms" or "complications" defined above that may be linked or are linked to neuro-damages. Such symptoms or complications may be, non-limitatively, neuro-muscular disorder(s), behavioral impairment (such as locomotor activity impairement), cognitive dysfunction(s) or impairment, brains disorder(s) including neuromyopathy and encephalopathy (also termed brain dysfunction herein, or sepsis-associated encephalopathy (SAE)).

Accordingly, in a particular embodiment the compounds of the invention as described herein are for use in alleviating symptoms of sepsis upon administration, and for preventing complications associated therewith which are susceptible to arise after sepsis resolution, through reversal of sepsis-induced microglial cells alteration(s), especially microglial cells alteration(s) of brain microglia, notably reprogramming of brain microglia.

In a particular embodiment the compounds of the invention as described herein are for use in alleviating symptoms of sepsis upon administration, and reversing of associated long-term cognitive impairment in a subject which has been subjected to a sepsis episode or sepsis-associated encephalopathy (SAE) episode (which have resolved when long-term cognitive impairment possibly arise).

In a particular embodiment the compounds of the invention as described herein are for use for preventing complications associated with sepsis which are susceptible to arise after sepsis resolution, by reversing sepsis-induced microglial cells alteration(s), thereby treating complications, especially long-term complications, notably long-term cognitive impairment, in a subject which has been subjected to a sepsis episode or sepsis-associated encephalopathy (SAE) episode.

According to another aspect, the compounds described herein have the property to act as a brain protective agent and/or cognitive function protective agent in the context of a subject suffering from sepsis, in particular for treating or alleviating complications associated therewith, including preventing complications associated therewith.

By "brain protective agent", it is meant that the agent has beneficial effects, in particular compared to an absence of treatment, with respect to "symptoms" (upon administration) or "complications" (on the long term) defined above that may be linked or are linked to damages affecting the brain or the brain function(s). Such symptoms or complications may be, non-limitatively, behavioral impairment (such as locomotor activity impairement), cognitive dysfunction (s) or impairment, brain oxidative damage, brain disorder(s) including neuromyopathy and encephalopathy (also termed brain dysfunction herein, or sepsis-associated encephalopathy (SAE)), or brain abnormalities such as neurodegenerative diseases (Alzheimer, FTDementia, Parkinson . . . ) or psychological alterations including depression, PTSD or other psychiatric diseases.

By "cognitive function protective agent", it is meant that the agent has beneficial effects, compared to an absence of treatment, with respect to the "symptoms" (upon administration) or "complicapults to a relative or absolute reference (which would be defined in healthy subjects.

Accordingly, the invention further relates to the use of compounds are described herein for improving or increasing antioxidant defence when treating sepsis as defined herein, and/or treating or alleviating symptoms thereof and/or complications associated therewith, as defined herein, especially in a subject having recovered from the condition(s) detailed herein, according to any combinations in the therapeutic effects sought.

Antioxidant defence may be assessed by investigating the SOD activity in treated subjects, compared to reference values obtained in a parallel experiment in the absence of treatment or corresponding to those found in healthy subject(s). Increase in antioxidant defence can be defined as a modulation with respect to the corresponding status that can be observed in subjects considered as healthy, said modulation tending to the restoration of functions at a level equal or superior to that found in a healthy subject. Modulation can be expressed in terms of percentage, and does not have to be complete. For example, modulation can be about 10%, 20%, 30%, 40%, 50%, 60%, 70%, 80%, 80%, 90%, 100% or greater, such as 110%, 120%, 130%, 140%, 150% or any percentage in between as compared to a control reference analyzed for the same parameter for reference.

According to another aspect, antioxidant defence improvement can be associated with any of the "protection" aspects discussed above. In particular, the present invention can be used to prevent, diminish or alleviate brain oxidative damage, in association with any one or all of the other effect(s) disclosed herein, or in isolation, according to the treatment features disclosed in any embodiment herein.

The invention also relates to compounds as described herein for use for counteracting oxidative stress, especially nitroso-redox stress, in particular in the brain, induced by sepsis or a similar event, for protecting the brain and/or cognitive function(s), in a patient suffering or susceptible of suffering from or having recovered from sepsis as defined herein, optionally for further treating one of said conditions or both, and/or treating or alleviating symptoms and/or complications thereof, especially in a subject having recovered from the consition(s) defined herein, as defined or disclosed in any of the embodiments described herein.

"Protection" aspects and "antioxidant defence" effects are highly relevant for improving the long-term consequences of a sepsis episode or related episode, in sepsis survivors.

According to a particular aspect, the present invention is therefore of interest in the context of the treatment of a subject having sepsis or symptom(s) and/or complication(s) thereof, alone or in combination with a rescue therapy, to alleviate short and/or long term symptoms and complications related to the occurrence of a septic episode, as defined herein, especially symptoms and/or complications that encompass psychocognitive or cognitive disorders, brain dysfunction, and brain oxidative damage, as defined herein. Prevention of late cognitive defects and/or cognitive function improvement in sepsis survivors, when MnTBAP is administered after the onset of a sepsis or related event, in a subject in need thereof, is also another aspect of the invention.

According to a particular embodiment, the treated sepsis condition is selected amongst: post-operative sepsis, neonatal sepsis, medical sepsis without prior knowledge of the circumstances giving rise to the condition, i.e., all patients diagnosed as having sepsis or for which suspicion of sepsis is present.

According to a particular embodiment, the subject is a mammal, in particular a human subject.

According to a particular embodiment, a compound as defined herein is first administered to a subject in need thereof within the first 24 hours after the onset of a sepsis episode according to any definition provided herein, or within the first 24 hours after the diagnosis or assessment of a suspicion of the presence of a sepsis episode. In lay terms, the said compound can be administered at an early stage.

Determining the exact time of onset of a sepsis episode may be difficult in real life, except perhaps when the event giving rise to the sepsis episode is perfectly identified, such as it may be the case in some iatrogenic events (iatrogenic sepsis episode). Nonetheless, diagnosis of sepsis often occurs within hours of the actual onset of the sepsis episode, so that it is possible to administrate a treatment at an early stage with one or several administration(s) as soon as possible after diagnosis while remaining in an "early stage" window" with respect to sepsis actual onset. According to a particular embodiment, administration(s) may be repeated in the time period spanning the further 48 hours or 96 hours after sepsis diagnosis.

According to a particular embodiment, a compound as defined herein is first administered to a subject in need thereof within the first 48 hours after the onset of a sepsis episode according to any definition provided herein, or within the first 48 hours after the diagnosis or assessment of a suspicion of the presence of a sepsis episode.

According to a particular embodiment, a compound as defined herein is first administered to a subject in need thereof within the first 96 hours after the onset of a sepsis episode according to any definition provided herein, or within the first 96 hours after the diagnosis or assessment of a suspicion of the presence of a sepsis episode.

According to a particular embodiment, a compound as defined herein is administered according to a regimen involving one or at least one, or involving several dose administrations over time, in particular 2, or 3, or 4, or 5 dose administration(s).

According to a particular embodiment, a compound as defined herein is administered 4 times within 24 or 48 or 96 hours of the onset, or diagnosis, or assessment of a suspicion, of the presence of a sepsis or related-condition episode.

According to a particular embodiment, a compound as defined herein is administered each (within interval(s) of) 12 hours, one, or two, or three or four time(s) after the onset, or diagnosis, or assessment of a suspicion, of the presence of a sepsis or related-condition episode.

According to a particular embodiment, a compound as defined herein is administered at a dose that is sufficient to induce the effects described herein, in particular a dose ranging from 5 to 15 mg/kg of active ingredient, or any range between 5, 6, 7, 8, 9, and 10 mg/kg as the lower value of the range and 11, 12, 13, 14 and 15 mg/kg of active ingredient as the higher value of the range, in particular a dose of 10 mg/kg. According to a particular aspect, variations in the dosage may occur when several administrations are made, according to all possible combinations within the ranges disclosed herein (for both the dosage and administration sequences).

According to a particular embodiment, in particular when the administered compounds are deemed to have better potency than MnTBAP, a compound as defined herein is administered at a dose ranging from 0.1 to 5 mg/kg of active ingredient, or 0.1 to 2 mg/kg of active ingredient, or any range between 0.1, 0.2, 0.3, 0.4, 0.5, 0.6, 0.7, 0.8, 0.9 and 1 mg/kg as the lower value of the range and 1.1, 1.2, 1.3, 1.4, 1.5, 1.6, 1.7, 1.8, 1.9 and 2.0 mg/kg of active ingredient as the higher value of the range, in particular a dose of 1 mg/kg. According to a particular aspect, variations in the dosage may occur when several administrations are made, according to all possible combinations within the ranges disclosed herein (for both the dosage and administration sequences).

According to a particular embodiment, a compound as defined herein is administered via any route that the person of ordinary skill in the art may find appropriate. According to an embodiment, said administration route is a non-invasive route, more particularly a route that does not require the use of any canula or other highly invasive instrument.

According to an embodiment, said administration route is the oral route.

According to an embodiment, said administration route is a systemic route.

According to an embodiment of the application, said administration route is a non-oral route, more particularly the intranasal route, the subcutaneous route, the intradermal route, the intramuscular route, the intravascular route.

The invention also relates to a composition, especially a pharmaceutical composition or medicament comprising, especially for the therapeutic purposes defined herein, at least a compound as defined herein, in particular MnTBAP, as an active ingredient, and a further usual pharmaceutical vehicle or adjuvant. Such a composition may encompass a compound as defined herein, in particular MnTBAP according to any one of formula (I) or (II) as disclosed herein, or mixture(s) thereof, including mixtures of several active ingredients (salt or complex) as defined herein.

The composition, especially pharmaceutical composition or medicament according to the invention can be in a form appropriate for (and, in particular, can comprise a vehicle appropriate for) any one of the route(s) of administrations detailed above.

The invention also relates to a method for the treatment of sepsis or a sepsis-related condition as defined herein, and/or for the treatment or lowering of symptoms thereof and/or complications associated therewith, as defined herein, in a subject in need thereof, as defined herein, the method comprising administering to a subject a compound or a composition comprising the same as defined herein, especially a therapeutically effective amount of the same, according to any one of the embodiments disclosed herein, and all possible combinations thereof. Instant description makes use of the "for use" wording for defining therapeutic applications. Throughout the description, a wording using the expression "method of" can be alternatively be used without the intended meaning being different.

The invention also relates to the use of a compound according to any one of the embodiments described herein, for the preparation of a medicament having the therapeutic purpose(s) or effect(s) described herein. Reference is made to any one of the embodiments described herein, and all combinations thereof, with respect to purpose(s) of said medicament.

Other examples and features of the invention will be apparent when reading the examples and the figures, which illustrate the experiments conducted by the inventors, in complement to the features and definitions given in the present description.

LEGEND OF THE FIGURES

FIG. 1. After induction of sepsis, microglial cells showed rapid morphological modifications that lasted in the long term despite resolution of sepsis Four regions of the brain have been explored: Hippocampus, Frontal Cortex, Striatum, and Cerebellum at different time points after sepsis. Results of the four regions are cumulated in a, b, d.

(a) Bar charts represents the characteristics of the microglial cell morphology: the cell body area and the cytoplasm area in $\mu m^2$, and morphological criteria extrapolated from the Acapella™ script: the complexity index (CI) and the covered environment area (CEA), in μm2.

(b) The microglial distribution was characterized using multiple parameters : density, calculated by dividing the number of microglial cells selected by the scanned tissue area (12.68 $mm^2$) and the percentage of amoeboid cells, as the ratio between the number of amoeboid cells and the total number of microglial cells analysed.

(c) Highlighting sub-populations by region. The pie charts represent the proportions of sub-populations defined by a cutoff calculated as the average of each morphological criterion (CI and CEA) in the control group by region of interest and by group (control and D21 groups): in yellow, sub-population with low CEA and low CI (−/−); in orange, sub-population with low CEA and high CI (−/+); in dark orange, sub-population with high CEA and low CI (+/−); and in red, sub-population with high CEA and high CI (+/+).

(d) Characterization of microglial cells by morphological criteria. Confocal images, representing a sub part of an analysed image in the frontal cortex region after maximum intensity projection. Individual microglia based on GFP fluorescence appear in white outline. Scale bar=50 μm. Ramification detection based on GFP fluorescence with the Acapella™ software. The complexity index (green) and the covered environment area (CEA in orange) have been derived from ramification detection. Scale bar=10 μm. For illustration, the images are contrast-adjusted to aid visualizing the GFP expression. For all time points mice were between 8 and 12 weeks old, and n=6 animals were analyzed per condition. Control mice were non-operated but anesthetized Data are represented as mean ±SD. ANOVA Kruskal-Wallis test was used to compare the different groups with the control group. *p<0.05, p<0.01, *p<0.001, ****p<0.0001.

FIG. 2. Sepsis induced rapid nitroso-redox stress and antioxidant defense dysfunction in serum, and from rapid to long term microglial reduction in oxidative stress, in antioxidant defense and bioenergetic reprogramming (a) Microglial ROS and RNS levels measured by CellRox; SOD activity measured by colorimetric analysis; quantitative RT-qPCR showing mRNA expression of microglial NRF-2; percentage of ATP content in microglial cells from control mice and at different time points post-sepsis, expressed relative to control; quantitative PCR measurements of the mtDNA content (12S region); relative percentage of OXPHOS/glycolytic ATP expressed relative to control in microglial cells extracted at different time points post-sepsis and in control mice.

(b) Individual schemes illustrating the microglial sequelae 21 days after sepsis in terms of bio-energetic metabolism and anti-oxydant defense.

(c) Individual scheme illustrating the serum sequelae 21 days after sepsis in terms of bio-energetic metabolism and anti-oxydant defense.

(d) Serum ROS (prevalently $H_2O_2$) and RNS (prevalently peroxynitrite, or $ONOO^-$) measured by DCFDA and DHR123 fluorescent probes, respectively; total Super Oxide Dismutase (SOD) activity measured by colorimetric analysis in serum in controls and at different time points post-sepsis. Dosages, activity, RT-qPCR and qPCR from three independent experiments, mean ±SD. *P≤0.05, P≤0.01, *P≤0.001, based on ANOVA test.

FIG. 3. Systemic MnTBAP treatment successfully counteracted long term sepsis effects (21 days) in microglial oxidative stress management, antioxidant defense and bioenergetic reprogramming (a) Microglial ROS levels measured by CellRox; SOD activity measured by colorimetric analysis; quantitative RT-qPCR showing the relative expression levels of microglial NRF-2; percentage of microglial ATP content relative to control; quantitative PCR measurements of mtDNA content (12S region); relative percentage of OXPHOS/glycolytic ATP in microglial cells extracted from control and CLP mice with or without MnTBAP. Data shown are mean values (±SD). Gray bars represent MnTBAP-treated mice from either CLP or control groups, and black bars represent placebo-treated mice from either CLP or Control groups. Two-way analyses of variance (ANOVAs) (CLP vs control× MnTBAP vs Placebo) were performed. When a significant interaction was observed, planned comparisons were performed for the CLP/Placebo group against the three other groups. The significance of the planned comparisons is indicated with asterisks (*p<0.05, p<0.01, *p<0.001, ****p<0.0001) .

(b) Individual schemes illustrating the effect of MnTBAP on the microglial sequelae 21 days after sepsis in terms of bio-energetic metabolism and antioxidant defense.

FIG. 4. Systemic MnTBAP treatment strongly reduced septic-mice mortality and restored cognition associated with partial rescue of oxidative stress management, increase in antioxidant defense and in bioenergetic metabolism in the brain (a) Brain ROS levels measured by CellRox; SOD activity measured by colorimetric analysis; quantitative RT-qPCR showing mRNA expression levels of brain NRF-2; percentage of microglial ATP content relative to control; quantitative PCR measurements of mtDNA content (12S region) in brain extracted from control and CLP mice with and without MnTBAP.

(b( )Individual schemes illustrating the effect of MnTBAP on the brain sequelae 21 days after sepsis in terms of bio-energetic metabolism and anti-oxidant defense.

(c) Novel object recognition and novel object location in percentage of exploration time of control and CLP mice with or without MnTBAP (n=10-12 per group). Data shown are mean values (±SD). Gray bars represent MnTBAP-treated mice from either CLP or control groups, and black bars represent placebo-treated mice from either CLP or Control groups. Two-way analyses of variance (ANOVAs) (CLP vs Control×MnTBAP vs Placebo) were performed. When a significant interaction was observed, planned comparisons were performed for the CLP/Placebo group against the three other groups. The significance of the planned comparisons is indicated with asterisks (*p<0.05, p<0.01, *p<0.001, ****p<0.0001).

(d) Survival curve of control and CLP mice with or without MnTBAP during time (n=10-12 per group). A log-rank (Mantel-Cox) p value for trend was calculated.

FIG. 5. CLP is a clinical pertinent model of sepsis (a) Diagram of the experimental set-up and procedure for the murine model.

(b) Survival curves of C57BL/6JRj (black line) and CX3CR1$^{GFP/+}$ (green line) mice after CLP. This experiment was performed in 108 mice (60 CX3CR1GFP/+ and 48 C57BL/6 JRj mice) and compared to 12 untreated control mice. A log-rank test was used for statistical analysis.

(c) Clinical parameters including percentage of weight loss compared to pre-operative weight, body temperature and locomotor score at 6, 12, 24 hours and 21 days post CLP.

(d) Haematoxylin and eosin of caecum in the control condition and at 24 h or 21 days post sepsis at 20× magnification. Twenty-four hours caecal sections showed histological abnormalities with edema, severe infiltration of the caecal serosa and caecal sub-mucosa by neutrophils associated with cell debris. Scale bar, 50 μm.

(e) Bar charts represents the level of protein expression in pg ml$^{-1}$ of plasma of IL1α, TNFα, IL6, IL10, IL13 and MCP-1 using Luminex®

Control mice were non-operated but anesthetized. For all time points mice were between 8 and 12 weeks old, and n=6 animals were analyzed per condition. Data are represented as mean ±SD. ANOVA Kruskal-Wallis test was used to compare the different groups with the control group. *p<0.05, p<0.01, *p<0.001.

Figures 6A, 6B:
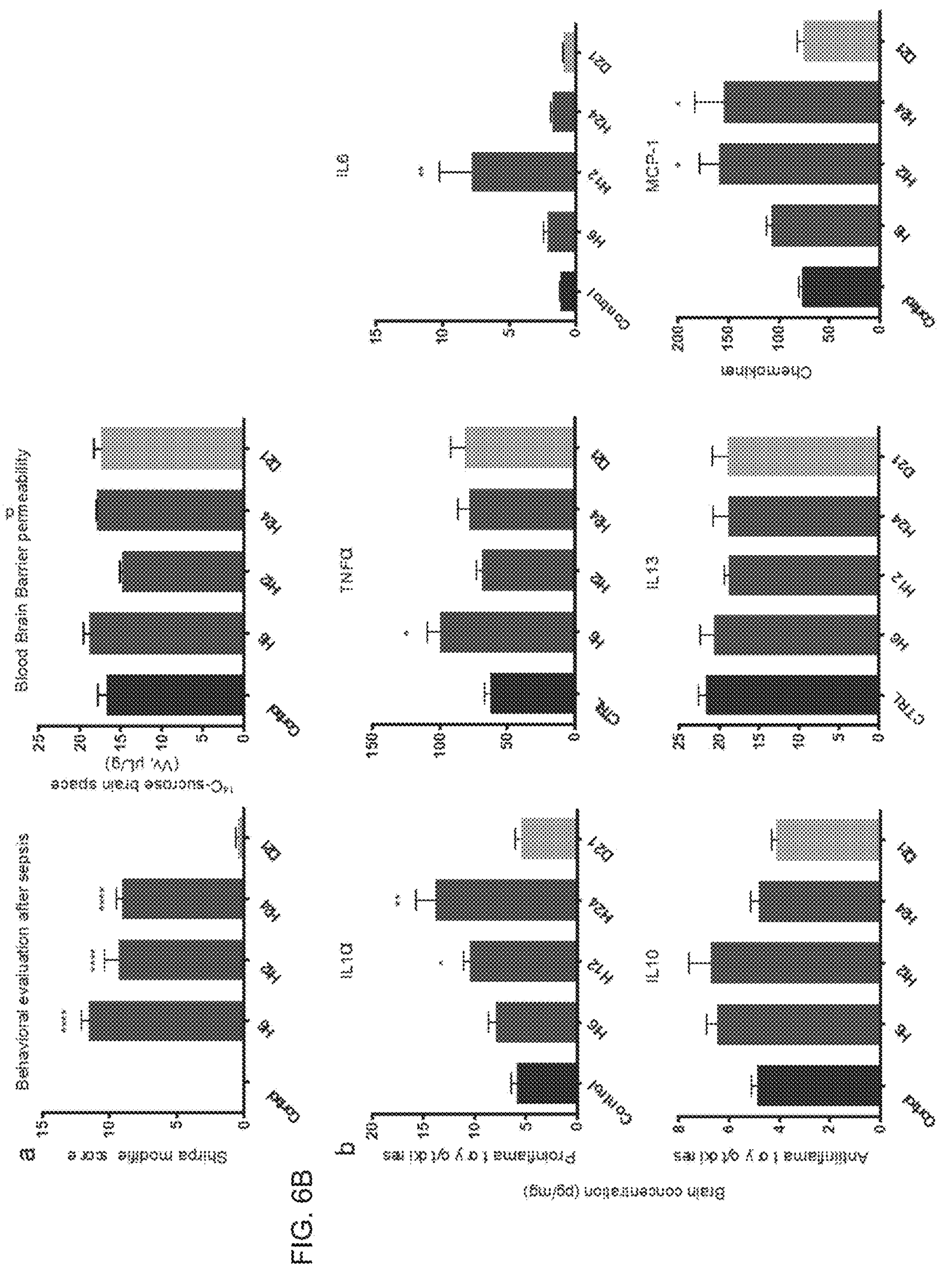

FIG. 6. CLP induces neuroinflammation at early stages without BBB leakage.

(a) Bar charts represents the modified SHIRPA score allowing to evaluate the mice behavior at different time points after sepsis.

(b) Bar charts represents the level of protein expression in pg mg$^{-1}$ of brain tissue of IL1α, TNFα, IL6, IL10, IL13 and MCP-1 using Luminex®.

(c) Haematoxylin and eosin of hippocampus in the control condition and at 24 h or 21 days post sepsis at 20× magnification. Scale bar, 50 μm. lba-1 and GFAP staining of hippocampus in the control condition and at 24 h or 21 days post sepsis.

Control mice were non-operated but anesthetized. For all time points mice were between 8 and 12 weeks old, and n=5 to 6 animals were analyzed per condition. Data are represented as mean ±SD. ANOVA Kruskal-Wallis test was used to compare the different groups with the control group. *p<0.05, p<0.01, *p<0.001.

FIG. 7. CLP reduces microglial antioxidant defense, affects central bioenergetic metabolite Acetyl-CoA level alteration and mitochondrial dysfunction (a) Expression of genes coding for antioxidants SOD1, SOD2, and Catalase quantified by RT-qPCR from RNA isolated from microglial cells extracted from control mice and at different time points post-sepsis.

(b) Levels of the central bioenergetic metabolite Acetyl-CoA expressed in nmol/g, and expression of the gene coding for PGC-1alpha quantified by RT-qPCR from RNA isolated from microglial cells extracted from control mice and at different time points post-sepsis.

(c) Expression of genes coding for CytB mRNA and 16S rRNA quantified by RT-qPCR from RNA isolated from microglial cells extracted from control mice and at different time points post-sepsis. Dosage and RT-qPCR, n=3 independent experiments, mean ±SD *P≤0.05, P≤0.01, *P≤0.001, based on the ANOVA test.

FIG. 8. Systemic MnTBAP treatment counteracts CLP effects in microglia through stimulation of the antioxidant, reduction of bioenergetic metabolite acetyl-CoA level and improvement of mitochondrial parameters (a) Expression of genes coding for the antioxidants SOD1, SOD2, and Catalase quantified by RT-qPCR from RNA isolated from microglial cells extracted from control and CLP mice with or without MnTBAP.

(b) Levels of the central bioenergetic metabolite Acetyl-CoA expressed in nmol/g, and expression of the gene coding for PGC-1alpha quantified by RT-qPCR from RNA isolated from microglial cells extracted from control and CLP mice with or without MnTBAP.

(c) Expression of genes coding for mitochondrial-coded CytB mRNA and 16S rRNA quantified by RT-qPCR from RNA isolated from microglial cells extracted from control and CLP mice with or without MnTBAP. Data shown are mean values (±SD). Gray bars represent MnTBAP-treated mice from either CLP or control groups, and black bars represent placebo-treated mice from either CLP or Control groups. Two-way analyses of variance (ANOVAs) (CLP vs Control×MnTBAP vs Placebo) were performed. When a significant interaction was observed, planned comparisons were performed for the CLP/Placebo group against the three other groups. The significance of the planned comparisons is indicated with asterisks (*p<0.05, p<0.01, *p<0.001, ****p<0.0001).

FIG. 9. Systemic MnTBAP treatment counteracts CLP effects in brain through stimulation of antioxidant defense expression and reduction of the bioenergetic metabolite acetyl-CoA level but not through mitochondrial parameters (a) Expression of genes coding for antioxidant SOD1, SOD2 and Catalase quantified by RT-qPCR from RNA isolated from brains extracted from control and CLP mice with or without MnTBAP.

(b) Levels of the central bioenergetic metabolite Acetyl-CoA expressed in nmol/g. Expression of genes coding for PGC-lalpha quantified by RT-qPCR from RNA isolated from brains extracted from control and CLP mice with or without MnTBAP.

(c) Expression of genes coding for mitochondrial-coded CytB mRNA and 16S rRNA quantified by RT-qPCR from RNA isolated from brains extracted from control and CLP mice with or without MnTBAP. Data shown are mean values (±SD). Gray bars represent MnTBAP-treated mice from either CLP or control groups, and black bars represent placebo-treated mice from either CLP or Control groups. Two-way analyses of variance (ANOVAs) (CLP vs Control× MnTBAP vs Placebo) were performed. When a significant interaction was observed, planned comparisons were performed for the CLPI/Placebo group against the three other groups. The significance of the planned comparisons is indicated with asterisks (*p<0.05, p<0.01, *p<0.001, ****p<0.0001) .

Figure 10:
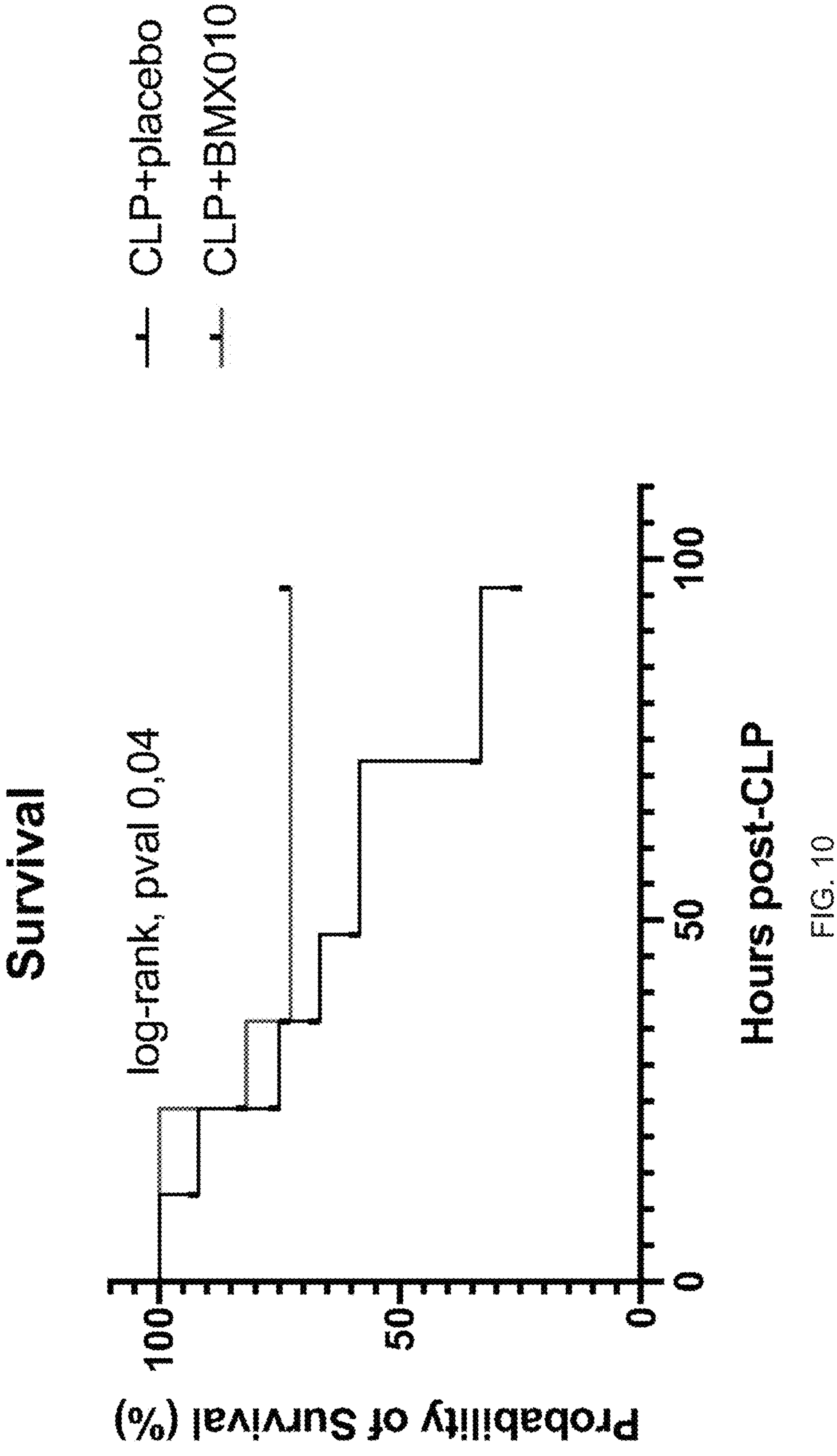

FIG. 10. Results of BMX-010 compound versus placebo in a CLP experiment, with regards to survival of mice hours post-CLP (probability of survival (%) shown over time): BMX-010 outperforms placebo.

MATERIAL AND METHODS

Animal Modeling

Experimental protocols were conducted in accordance with the French and European regulations on Animal Welfare and with Public Health Service recommendations. They have been reviewed and approved by the Institut Pasteur Ethics Committee.

The experiments were performed on C57BL/6JRj mice purchased from Janvier Laboratory or in-house knock-in (KI) CX3CR1$^{GFP/+}$ mice. The CX3CR1$^{GFP/+}$ mice express EGFP in monocytes, dendritic cells, NK cells, and brain microglia under the control of the endogenous CX3CR1 locus (Jung et al., 2000). The mice were housed in cages in groups of 7, in a temperature (22±1.5° C.) and humidity-controlled environment, with a 12 h light/dark cycle. All animals used in the study were between 10 and 12 weeks old. Sample-size estimates for animal experiments were based on prior animal-modelling studies used in the Unit for the investigation of caecal ligation and puncture (CLP).

At the time of experimentation, animals were randomly distributed for control and CLP. There was no investigator blinding in animal experimentation, and no animals were excluded from analysis, except those who died before surgery or analyses. The same experimenter did all the animal experiments with a protocoled surgical procedure.

Cecal Ligation and Puncture (CLP) and Control Mice

We used peritonitis induced by CLP as a model of sepsis (Rittirsch et al., 2009). Briefly, animals were anesthetized with ketamine (Imalgene® 1000 100 mg/kg, Merial, France) and Xylazine (Rompun® 2% 20 mg/kg, Bayer, Germany) prior to surgery. After laparotomy, caecum was ligatured at the distal third with a 4.0 suture and the distal part was perforated twice with a 21 Gauge needle.

Control animals were anesthetized using the same protocol and received no surgical procedure.

All animals in the CLP and the control groups were rehydrated and treated with analgesic (Buprenorphin 0.3 mg/kg, Axience SAS, France) twice a day for 2 days following surgery. Mice were sacrified at the time points indicated in the results or when moribund, in accord with criteria established in the animal-use protocol. The protocol is detailed in Supp FIG. 1*a*.

Pharmacological Intervention

In a second step of experiences, the control and CLP mice were randomized to receive an intraperitoneal (IP) injection of 100 μL of isotonic saline solution (NaCl 0.9%), or of Manganese (III) tetrakis (4-benzoic acid)porphyrin chloride (MnTBAP; Enzo®, ALX-430-069) at a dose of 10 mg/kg every 12 hours for 48 hours. MnTBAP is commercially available: it is for example manufactured by Sigma-Aldrich, Calbiochem, etc. For use it is dissolved following the guidance provided by the manufacturer.

At the end, four groups were compared: control-placebo, control-MnTBAP, CLP-placebo, CLP-MnTBAP, which each included 12 to 16 mice.

Clinical Analyses

Clinical score was assessed 6, 12 and 24 hours and 21 days after CLP using a modified SmithKline Beecham, Harwell, Imperial College and Royal London Hospital phenotype assessment (SHIRPA) (Rogers et al., 1997) of the maximum score of fourteen. Weight, temperature and locomotor activity using an open field box were measured at the same time points. We determined survival rate twice a day for 21 days after CLP. The symptoms included in the a modified SmithKline Beecham, Harwell, Imperial College and Royal London Hospital phenotype assessment (SHIRPA) are tremors, periorbital exudates, piloerection, lethargy, vocalisation, positional passivity, no escapement to threat, long transfer arousal and diarrhoea. Each condition was scored from 0 to 2.

Cognitive Analyses

Twice a week after the CLP, survival mice were gently handled for at least four 5-min sessions to habituate to the experimenter. Then, 20 and 21 days after CLP, mice were submitted to the novel object location (NOL) and novel object recognition (NOR) tests. The protocol usedfor the novel object location (NOL) and novel object recognition (NOR) tests was adapted from Leger et al. (Leger et al., 2013). A short habituation (less than 5 minutes), familiarization session and 1 h-interval test of the NOL test were performed on D20. A short habituation (less than 5 minutes) and familiarization session of the NOR test were performed on D20 right after the NOL test. The NOR test were performed 24 hours later (21 days after sepsis).

The familiarization sessions consisted on 10 min of free exploration of two identical objects, placed inside the same open field arena that the mice had visited on the previous day. At either 1 h or 24 h after the familiarization session, one of the familiar objects was replaced by a new one (NOR) or at a new location (NOL), and mice were re-exposed to the arena for 5 min for the test. Objects were randomly assigned as A, B or C for each individual, and so was the location of the novel object in the test sessions (left or right), to avoid preference biases. Time exploring the objects, i.e. when the snout of the mouse was directed towards the objects from a distance shorter than 2 cm (except when climbing), was registered during both test sessions. Then, the percentage of exploration of the new object was calculated, reflecting the retention of the familiar object memory at long-term (24 h). An exploration level above 50% (chance level) indicates good memory retention.

Histological Analysis and Immunohistochemistry

Mice were anesthetized and brains were immediately removed and cut in a trans-sagittal plane in the interhemispheric fissure. Hemispheres were fixed during 48 hours in 4% buffered formalin (QPath, Labonord SAS, Templemars, France) or zinc (0.5% zinc chloride, 0.5% zinc acetate in 0.1 M Tris base buffer). After fixation, all tissue specimens were processed according to standard procedures and were paraffin embedded. Paraffin sections of 4-μm thickness of the right hemisphere were stained with hematoxylin and eosin to assess histopathological modifications of the tissue. For immunohistochemistry analyses, paraffin sections of 4-μm thickness of the left hemisphere were incubated with antibodies directed against microglial cell (rabbit antibody to lba-1; Wako Chemicals, Richmond, VA, 1:500) and astrocytes (chicken anti-GFAP; Abcam, ab4674, 1:2000). Primary antibodies were revealed by Dy488-, Cy3- or tetramethylrhodamine-labeled secondary antibodies (Jackson InnnnunoResearch Laboratories, Baltimore, PA). A classical protocol was used: rehydratation, blocking with 20% goat serum and 0.5% Triton-X 100 for two hours, incubation with primary antibody (Dako Diluent buffer, Glostrup, Denmark) overnight at 4° C. followed by incubation with secondary antibody for four hours at room temperature. The counterstained sections were mounted on slides, coverslipped and analyzed by an independent neuropathologist.

Microglial Morphology Analyses

Morphological analysis was realized according the protocol described previously by the authors (Verdonk et al., 2016b). Briefly, microglial cells morphology was assessed on 100 μm thick free-floating slices of CX3CR1$^{GFP/+}$ brains (VT1000 S, Leica, Germany). Using a spinning disk confocal system (Cell Voyager-CV1000, Yokogawa, Japan) with a UPLSAPO 40x/NA 0.9 objective and the 488 nm laser, four regions of interest were acquired: Striatum, Frontal Cortex, Hippocampus and Cerebellum, covering approximately 3.17 mm$^2$ of tissue per region with depth of 30 μm at 2 μm increment (16 focal depths). Before shape characterization analysis, focal stacks of each mosaic were reconstructed using automated free PlugIn of the ImageJ software interface. An automatic image analysis was then performed using a custom designed script developed with the Acapella™ image analysis software (version 2.7-Perkin Elmer Technologies). Different parameters could be extracted for each microglial cell on more than 20,000 cells per condition: cell body and cytoplasm area, defined as the cell body area associated with the cytoplasmic area of the primary ramifications expressed in μm$^2$; branching characteristics such as the total number and length (μm) of ramifications, the number of primary, secondary and tertiary ramifications; roundness (ratio between surface and perimeter of cell body) and GFP intensity by whole cell. A second set of calculated criteria extrapolated from the previous ones, yielded the Complexity Index (CI) and Covered Environment Area (CEA). CI corresponds to a mean complexity by primary ramification in order to characterize objectively the complexity of each cell. CEA represents to the 2D total surface covered by its ramifications and is defined as the area of the polygon formed by linking the extremities of its ramifications, expressed in μm$^2$. The density of microglial cells per brain was calculated by dividing the number of microglial cells by the scanned tissue area (±12.68 mm$^2$/region).

Microglial Extraction by CD11b+Magnetic-Cell Sorting

Brains were collected for cell dissociation and Cdllb-positive cell separation using a magnetic coupled antibody (MACS® Technology), according to the manufacturer's protocol (Miltenyi Biotec, Bergisch Gladbach, Germany) and as previously described (Schang et al., 2014). In brief, mice were intracardially perfused with NaCl 0,9%. The brains are then dissociated using the Neural Tissue Dissociation Kit containing trypsin and the gentleMACS Octo Dissociator with Heaters. From the resulting brain homogenate, cd11 b-positive cells were enriched using the anti-cd11 b MicroBeads. After elution the isolated cells were centrifuged for 5 min at 200G and conserved at −80° C.

The purity of the eluted DC11 b-positive fraction was verified by FACS analysis gated on GFP. FACS experiment revealed that more than 95% of the isolated cells were GFP cells.

RNA Extraction and Quantification of Gene Expression by Real-Time qPCR

Total RNA was isolated from cells using the RNAeasy Micro kit (Qiagen), and reverse-transcribed using Superscript® III Reverse transcriptase (Invitrogen). Real-time quantitative PCR was performed in duplicate for each sample using Power Sybr Green PCR Master Mix (Applied Biosystems) and the rate of dye incorporation was monitored using the StepOne™ Plus RealTime PCR system (Applied Biosystems). Data were analyzed by StepOne Plus RT PCR software v2.1 and Microsoft excel. Amplification specificity was assessed with a melting curve analysis. TBP transcript levels were used for normalisation of each target (=ΔCT). Real-time PCR $C_T$ values were analyzed using the $2^{-(\Delta Ct)}$ method to calculate the fold expression (Schmittgen et al., 2008). The data are presented as relative mRNA units with respect to control group (expressed as fold over control value). Primer sequences available upon request.

RT-qPCR and qPCR Primer List Regarding the mtDNA Content

| Gene | | RT-qPCR primers | SEQ ID NO: |
|---|---|---|---|
| Mouse TBP | Forward | CTTCACCAATGACTCCTATG | 1 |
| | Reverse | TGACTGCAGCAAATCGCTTG | 2 |
| | Reference | *Cooper et al. 2006, Genes & Dev. 20:2996-3009* | |
| | DOI | 10.1101/gad.1483906 | |
| Mouse Catalase | Forward | AGAGAGCGGATTCCTGAGAGA | 3 |
| | Reverse | ACCTTTCCCTTGGAGTATCTG | 4 |
| | Reference | *Choi et al. 2009, PLoS One, 4(11):e8011* | |
| | DOI | 10.1371/journal.pone.0008011 | |
| Mouse NRF2 | Forward | AGAGAGCGGATTCCTGAGAGA | 3 |
| | Reverse | ACCTTTCCCTTGGAGTATCTG | 4 |
| | Reference | *Choi et al. 2009, PLoS One, 4(11):e8011* | |
| | DOI | 10.1371/journal.pone.0008011 | |

-continued

| Gene | | RT-qPCR primers | SEQ ID NO: |
|---|---|---|---|
| Mouse SOD1 | Forward | GGACCTCATTTTAATCCTCAC | 5 |
| | Reverse | TGCCCAGGTCTCCAACATG | 6 |
| | Reference | *Bhusari et al. 2008, J of Thermal Biology, 33, 157-167* | |
| | DOI | 10.1016/j.jtherbio.2008.01.001 | |
| Mouse SOD2 | Forward | CAGACCTGCCTTACGACTATG | 7 |
| | Reverse | CTCGGTGGCGTTGAGATTG | 8 |
| | Reference | *Choi et al. 2009, PLoS One, 4(11):e8011* | |
| | DOI | 10.1371/journal.pone.0008011 | |
| Mouse PGC1A (Pprgc1a) | Forward | GGACAGTCTCCCCGTGAT | 9 |
| | Reverse | TCCATCTGTCAGTGCATC | 10 |
| | Reference | *Viscomi et al. 2009, Human Molecular Genetics, 18(1):12-26* | |
| | DOI | 10.1093/hmg/ddn309 | |
| Mouse 16S rRNA | Forward | GGGACTAGCATGAACGGCTA | 11 |
| | Reverse | CCCCAACCGAAATTTCAAAC | 12 |
| | Reference | Schmidt et al. 2008; Mol Cell Biol, 28(5):1489-1502 | |
| | DOI | 10.1128/MCB.01090-07 | |
| Mouse CYTB | Forward | ACGTCCTTCCATGAGGACAA | 13 |
| | Reverse | GAGGTGAACGATTGCTAGGG | 14 |
| | Reference | *Schmidt et al. 2008; Mol Cell Biol, 28(5):1489-1502* | |
| | DOI | 10.1128/MCB.01090-07 | |
| Mouse NDUFV1 | Forward | CTTCCCCACTGGCCTCAAG | 15 |
| | Reverse | CCAAAACCCAGTGATCCAGC | 16 |
| | Reference | *Guo et al. 2009. Mitochondrion, 9(4):261-265* | |
| | DOI | 10.1016/j.mito.2009.03.003 | |
| Mouse CO1 | Forward | TGCTAGCCGCAGGCATTAC | 17 |
| | Reverse | GGTGCCCAAAGAATCAGAAC | 18 |
| | Reference | *Guo et al. 2009. Mitochondrion, 9(4):261-265* | |
| | DOI | 10.1016/j.mito.2009.03.003 | |

Nomenclature of Microglial Phenotype

We have adopted nomenclature consistent with previous work in microglia (Chhor et al., 2013). We distinguished 3 types of phenotypes according to the mRNA expression levels of markers listed in brackets: pro-inflammatory phentoype (Ptgs2, Cd32, Cd86), alternative phenotype (Lgals3, Igf1 and CD206) and immunoregulatory phenotype (Il1rn, Il4ra, Socs3).

Chemokines and Cytokines Measurement by Luminex® Assay

Blood: Serum Blood was put on ice and plasma was collected by centrifugation at 800 g for 15 min at 4° C., aliquoted and stored at −80° C. until analysis.

Brain: snap frozen brain samples (n=6 per condition and per time point) were thawed, lysed by mechanical agitation (lysing matrix), and supernatant was aliquoted and stored at −80° C. until analysis.

These samples were processed for Luminex® multiple cytokine and chemokine analysis (Bio-Plex® Pro™ Mouse Cytokine Standard 23-flex, Group I and Standard 9-flex, Group II). Fifty microlitres of sample was analyzed on the Bio-flex system (Bio-Rad) in accordance with the manufacturers instructions. Data analyses for all assays were performed using the Bio-flex Manager software. Cytokine detection by Luminex xMAP technology is comparable to that with enzyme-linked immunosorbent assay (ELISA; correlation coefficient r ranges from 0.75 to 0.99) (Staples et al., 2013). Normalization was done by weight of the frozen brain sample.

Protein Extraction

Microglial cells and brain samples were resuspended in lysis buffer (50 mM Tris·HCl pH 7.5, 150 mM NaCl, 1% Triton X-100, 0.1% SDS, 1 mM EDTA, and protease inhibitor mixture), mechanically homogenized with a piston, briefly vortexed and incubated for 30 min at 4° C. Lysed samples were briefly centrifuged to remove debris, and the whole supernatant extract was collected. Aliquots of the supernatant were immediately used for the assessment of ROS level, RNS level, dual ROS/RNS level, SOD activity, and Acetyl-Coa level. The protein content was determined with the Bradford reagent (Sigma-Aldrich).

Detection of ROS/RNS With CellROX in Microglial Cells and Brain Extract

Both ROS and RNS were measured by incubating CellROX (Life Technologies) with 30 μg of freshly extracted total proteins for 45 min at 37° C. in the dark in 96-wells plate in triplicate. Fluorescence intensity was measured using near-infra-red fluorescence setting with the plate reader Odyssey Infrared Imaging system scanner and Odyssey application software v3.0 (LI-COR Biosciences, Lincoln, NE).

Detection of ROS With DCFHDA in Serum

The ROS level was measured by incubating DCFHDA (2',7'-Dichlorodihydrofluorescin diacetate, Sigma-Aldrich) with a serum volume of 10 μl for 45 min at 37° C. in the dark in 96-wells plate in triplicate. Green fluorescence intensity was measured using green fluorescence setting with the plate reader Odyssey Infrared Imaging system scanner and Odyssey application software v3.0 (LI-COR Biosciences, Lincoln, NE).

Detection of RNS Peroxynitrite With DHR123 in Serum

The RNS peroxynitrite level was measured by incubating DHR123 (Dihydrorhodamine 123, Sigma-Aldrich) with a serum volume of 10 µl for 45 min at 37° C. in the dark in 96-wells plate in triplicate. Green fluorescence intensity was measured using green fluorescence setting with the plate reader Odyssey Infrared Imaging system scanner and Odyssey application software v3.0 (LI-COR Biosciences, Lincoln, NE).

SOD Activity

SOD activity was measured with Superoxide Dismutase Activity Colorimetric Assay kit (Abcam, ab65354), following the manufacturer's instructions. This measurement assesses SOD-dependent inhibition of superoxide anion reduction. Tests were performed with 30 µg of freshly extracted total proteins, quantified by Bradford assay, or with 10 µl of serum, in triplicate.

Quantification of mtDNA Content by qPCR

Total DNA was prepared using extraction buffer (0.2 mg $ml^{-1}$ proteinase K, 0.2% SDS and 5 mM EDTA in PBS) and incubated at 50° C. for 3 h. DNA was precipitated with 3 M sodium acetate (pH 5.2) and isopropanol for 20 min on ice before centrifugation at 8,000 g at 4° C. The DNA pellet was washed and briefly air-dried. qPCR amplification was performed on total DNA using the StepOne Plus RealTime PCR system (Applied Biosystems) and Power Sybr Green PCR Master mix (ABI) following the manufacturer's instruction. A fragment of mitochondrial COI gene, the established marker for mtDNA content in mouse cells, was amplified using the nuclear encoded Ndufv1 gene as endogenous reference. The level of mtDNA was calculated using the $\Delta C_T$ of average $C_T$ of mtDNA and nDNA ($\Delta C_T = C_T$ nDNA$-C_T$ mtDNA) as $2^{-(\Delta Ct)}$. Primer sequences available upon request.

ATP Steady-State Level and OXPHOS/Glycolysis Ratio in Microglial Cells

Total ATP levels and OXPHOS/Glycolysis ratio were measured for 10,000 freshly isolated microglial cells, and for OXPHOS/Glycolysis ratio 10 µM oligomycin (Sigma-Aldrich) was used for 1 h at 37° C. to inhibit mitochondrial ATP synthesis and assess glycolysis contribution. The CellTiter-Glo luminescent assay was used following the manufacturer's procedure (Promega).

ATP Steady-State Level in Brain Extract

Total ATP levels were measured with 30 µg of daily fresh total protein extract from brain extract using the CellTiter-Glo luminescent assay following the manufacturer's procedure (Promega).

Acetyl-CoA Level in Microglial Cells and Brain Extract

Acetyl-CoA levels were measured with 30 µg of daily fresh total protein extract from brain extract and microglial cells using the Acetyl-Coenzyme A assay following the manufacturer's procedure (Sigma Aldrich, MAK039).

MnTnBuOE-2-Pyp5+ Testing

Experimental protocols were conducted in accordance with the French and European regulations on Animal Welfare and with Public Health Service recommendations. The experiments were performed on C57BL/6JRj mice (male and female) purchased from Janvier Laboratory. Mice were housed in cages in groups of 7, in a temperature (22±1.5° C.) and humidity-controlled environment, with a 12 h light/dark cycle. All animals used in the study were between 10 and 12 weeks old. Sample-size estimates for animal experiments were based on prior animal-modelling studies used in the Unit for the investigation of caecal ligation and puncture (CLP).

CLP mice were randomized to receive an intraperitoneal (IP) injection of 100 µL of isotonic saline solution (NaCl 0.9%), or of MnTE-2-Pyp5+ (BMX-010) at a dose of 2 mg/kg every 12 hours for 48 hours. At the end, two groups were compared: CLP-Placebo, CLP-BMX-010. We determined survival rate twice a day for 4 days after CLP."

Data Analysis and Statistics

Conventional Approach

Prism 6.0 (GraphPad Software Inc.®, USA) was used for statistical analysis. Two types of complementary approaches were used. First, molecular, cellular and behavioral parameters over the course of sepsis were analyzed with the Mann-Whitney test or Student's t-test after being assessed for normality. Qualitative traits were analyzed with a Chi2 test. Second, two-way analyses of variances (ANOVAs) (CLP vs control×MnTBAP vs placebo) were performed to compare the effects of treatments on molecular, cellular and behavioral parameters. Significant differences between groups were further evaluated using Tukey's post hoc tests. In order to remain focused on the study of a specific effect of MnTBAP on our model of sepsis, the interpretation of the tests focusses only on significant interactions. Positive analyses which were specific to the condition or treatment criteria will not be addressed here.

Statistical significance is shown on the graphs (ns, not significant; *$p<0.05$; $p<0.01$; *$p<0.001$; ****$p<0.0001$). Statistics used for each data set are indicated in the respective figure legend.

Clustering Analysis

Specifically, for morphological analysis, in a second time, Prism data were transferred into JMP® version 11.0 (Statistical Analysis System Institute Inc., USA) and a complete multivariate analysis by cell population was done. A principal component analysis (PCA) was performed to identify the correlation between the different analysed features. To detect and characterize the sub-population of microglial cells, a k-means clustering method, appropriated for a large set of data, has been applied (k=4). The statistics of each cluster (mean and frequency) were used to characterize sub-populations and determine their phenotype.

Results

Figure 5A:
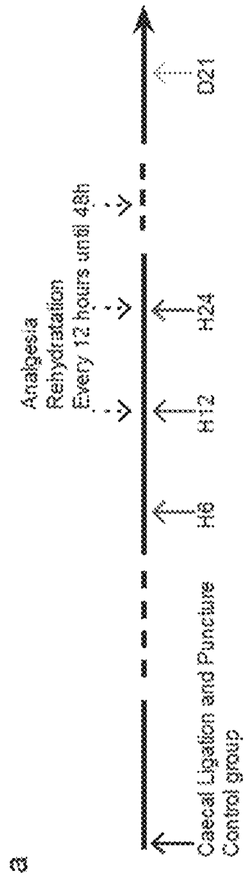
Figure 5B:
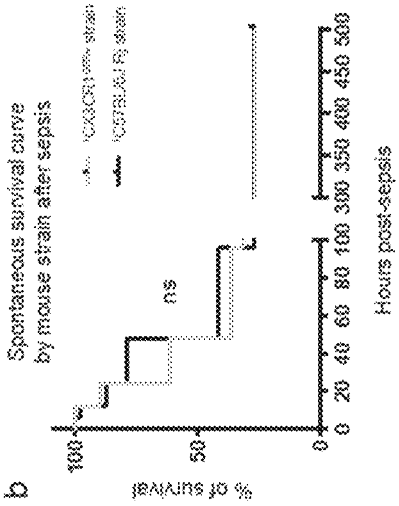
Figure 5C:
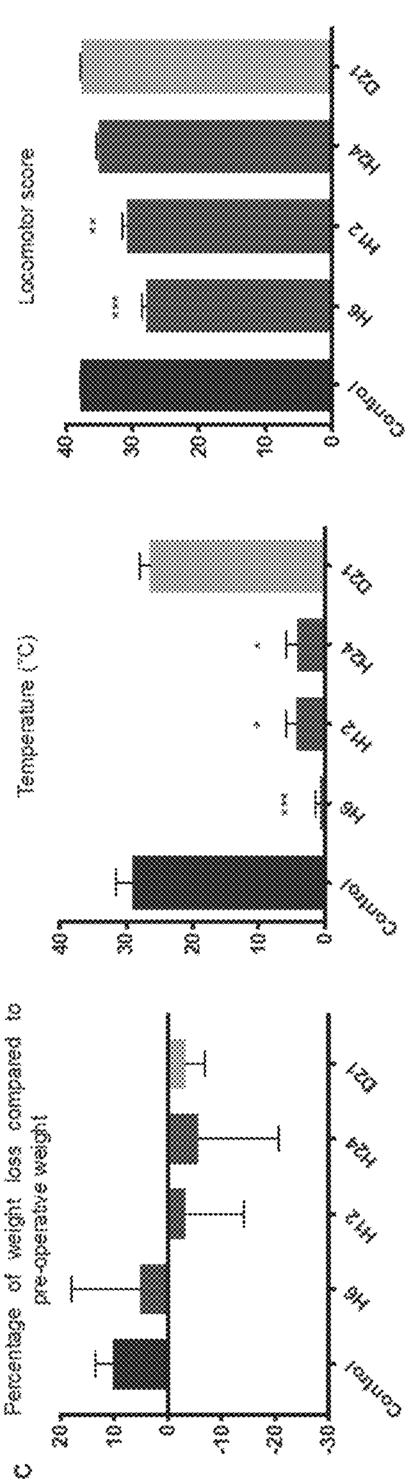
Figure 5D:
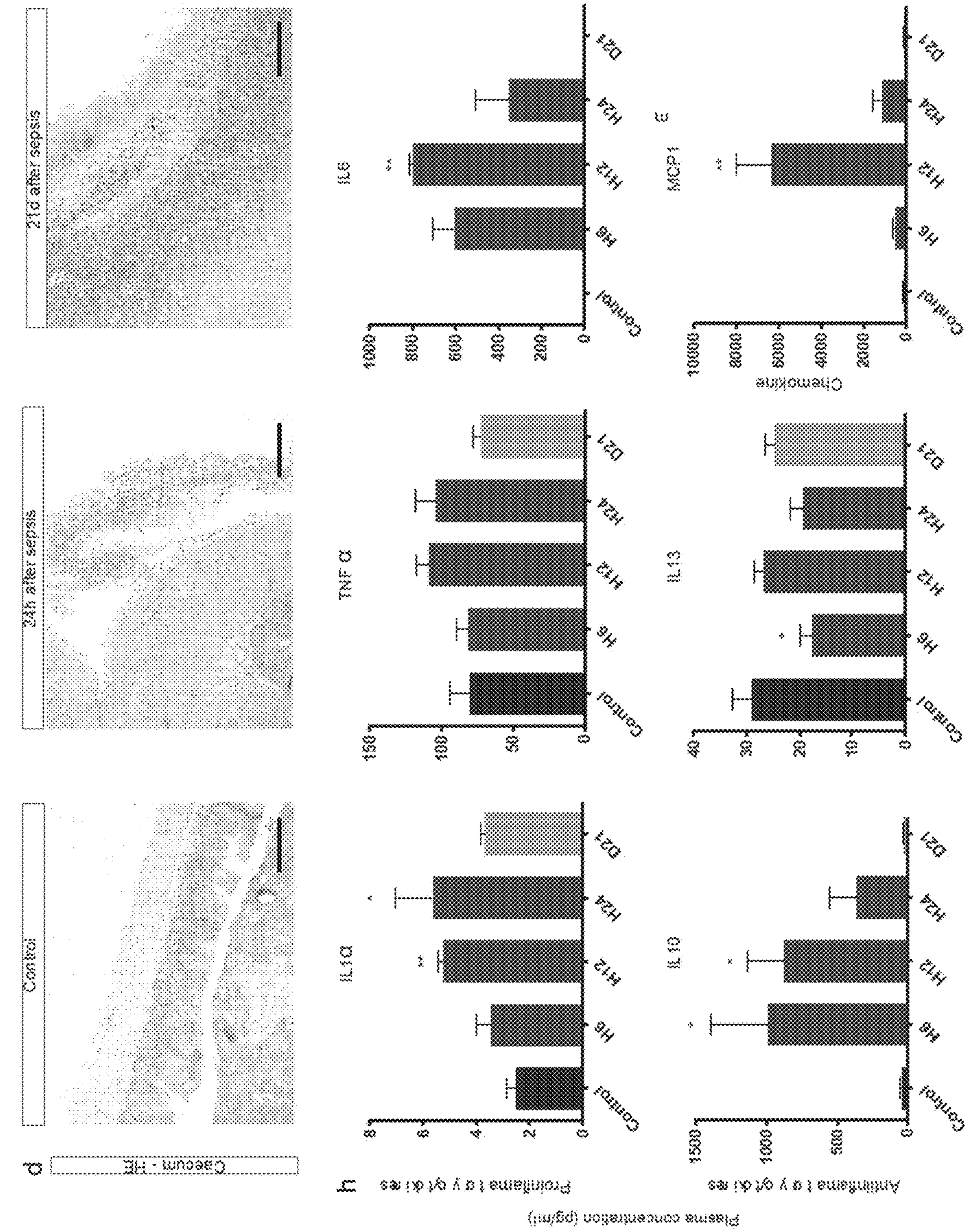

Sepsis Induces Long Term Morphological and Phenotypic Microglial Alterations in Survivors Systemic Level CLP induced a high mortality rate in both C57BL/6JRj and CX3CR1$^{GFP/+}$ mouse strains (73% of mortality 21 days after CLP) (FIG. 5*b*) and clinical alterations (FIG. 5*b*-*d*). An early (i.e. 6 hours) and short (up to 24 hours) systemic inflammatory response occurred in septic mice (FIG. 5*e*; Table 3). Concurrently, severe sickness behavior (FIG. 6*a*) and neuro-inflammation (FIG. 6*b*; Table 3) is observed. Twenty-one days after CLP, in survivors, these clinical and inflammatory parameters were back to baseline and did not differ from the control group.

TABLE 3

| | Control | H6 | H12 | H24 | D21 | ANOVA | Control vs H6 | Control vs H12 | Control vs H24 | Control vs D21 |
|---|---|---|---|---|---|---|---|---|---|---|
| Plasma Cytokines | | | | | | | | | | |
| IL-1α | 2.58 | 3.03 | 5.32 | 4.27 | 3.80 | 0.0079 | ns | 0.0038 | 0.0238 | ns |
| IL-1β | 14.66 | 16.17 | 26.26 | 14.52 | 12.45 | 0.0321 | ns | ns | ns | ns |
| IL-6 | 4.63 | 633.68 | 816.22 | 193.45 | 2.25 | 0.0005 | ns | 0.0071 | ns | ns |
| IL-10 | 32.53 | 612.65 | 974.48 | 92.09 | 24.80 | 0.0012 | 0.045 | 0.0351 | ns | ns |
| IL-12(p40) | 163.32 | 88.20 | 742.63 | 118.84 | 106.42 | 0.0082 | ns | ns | ns | ns |
| IL-12(p70) | 180.50 | 155.12 | 262.22 | 231.47 | 174.46 | ns | NA | NA | NA | NA |
| IL-13 | 25.39 | 18.41 | 25.51 | 18.03 | 23.23 | 0.0148 | 0.0238 | ns | ns | ns |
| IL-17 | 7.09 | 11.41 | 34.43 | 6.74 | 5.46 | 0.01 | ns | 0.0417 | ns | ns |
| GM-CSF | 49.92 | 41.10 | 69.75 | 53.06 | 23.44 | 0.0264 | ns | ns | ns | ns |
| IFN-g | 25.33 | 20.03 | 45.49 | 37.57 | 19.02 | 0.0297 | ns | ns | ns | ns |
| KC | 39.91 | 4678.28 | 4842.61 | 2825.07 | 49.48 | 0.0008 | 0.0237 | 0.0036 | ns | ns |
| MCP1 | 115.91 | 420.70 | 8016.18 | 422.78 | 104.14 | 0.0004 | ns | 0.002 | ns | ns |
| MIP1a | 5.21 | 13.83 | 16.68 | 9.23 | 4.88 | 0.0041 | 0.0397 | 0.0272 | ns | ns |
| TNFα | 74.53 | 79.12 | 114.68 | 114.14 | 70.08 | ns | NA | NA | NA | NA |
| RANTES | 48.14 | 62.74 | 124.93 | 156.43 | 45.90 | 0.0016 | ns | 0.0209 | 0.0351 | ns |
| Brain Cytokines | | | | | | | | | | |
| IL-1α | 5.49 | 6.95 | 9.49 | 14.66 | 5.95 | 0.001 | ns | 0.039 | 0.005 | ns |
| IL-1β | 4.17 | 3.86 | 3.38 | 3.00 | 3.19 | 0.023 | ns | ns | 0.027 | 0.031 |
| IL-6 | 1.10 | 2.37 | 6.90 | 1.70 | 0.95 | 0.0006 | ns | 0.007 | ns | ns |
| IL-10 | 5.04 | 6.90 | 6.37 | 4.68 | 4.19 | 0.005 | ns | ns | ns | ns |
| IL-12(p40) | 76.87 | 63.21 | 75.64 | 62.59 | 62.62 | ns | NA | NA | NA | NA |
| IL-12(p70) | 40.17 | 33.30 | 35.57 | 37.41 | 37.86 | ns | NA | NA | NA | NA |
| IL-13 | 22.38 | 18.96 | 18.77 | 18.35 | 18.06 | ns | NA | NA | NA | NA |
| IL-17 | 9.24 | 8.20 | 7.75 | 10.71 | 10.98 | ns | NA | NA | NA | NA |
| GM-CSF | 3.44 | 3.69 | 3.22 | 3.10 | 3.36 | ns | NA | NA | NA | NA |
| IFN-g | 9.98 | 7.95 | 8.36 | 12.85 | 8.83 | ns | NA | NA | NA | NA |
| KC | 38.52 | 335.37 | 1070.00 | 213.59 | 50.72 | 0.0004 | ns | 0.0003 | ns | ns |
| MCP1 | 80.88 | 105.90 | 170.07 | 156.13 | 76.48 | 0.003 | ns | 0.013 | 0.057 | ns |
| MIP1a | 9.51 | 10.23 | 8.22 | 9.49 | 9.03 | ns | NA | NA | NA | NA |
| TNFα | 68.17 | 97.20 | 65.56 | 83.03 | 83.93 | 0.041 | 0.016 | ns | ns | ns |
| RANTES | 6.17 | 5.17 | 5.50 | 4.96 | 5.77 | ns | NA | NA | NA | NA |

CLP Induces Increased Cytokine and Chemokine Levels in the Brain Parenchyma and in the Plasma According to Different Time Courses The data shown represent the level of protein expression in pg mg-1 of tissue and in pg ml-1 of plasma using Luminex®. Control mice were non-operated but anesthetized. The data shown represent median values of n=5 mice per group. Kruskal Wallis tests were performed to compare the Control, H6, H12, H24 and D21 groups. In case of statistical significance, multiple comparisons were performed and indicated on the table. ns: not significant.

Cellular Level

Figure 6C:
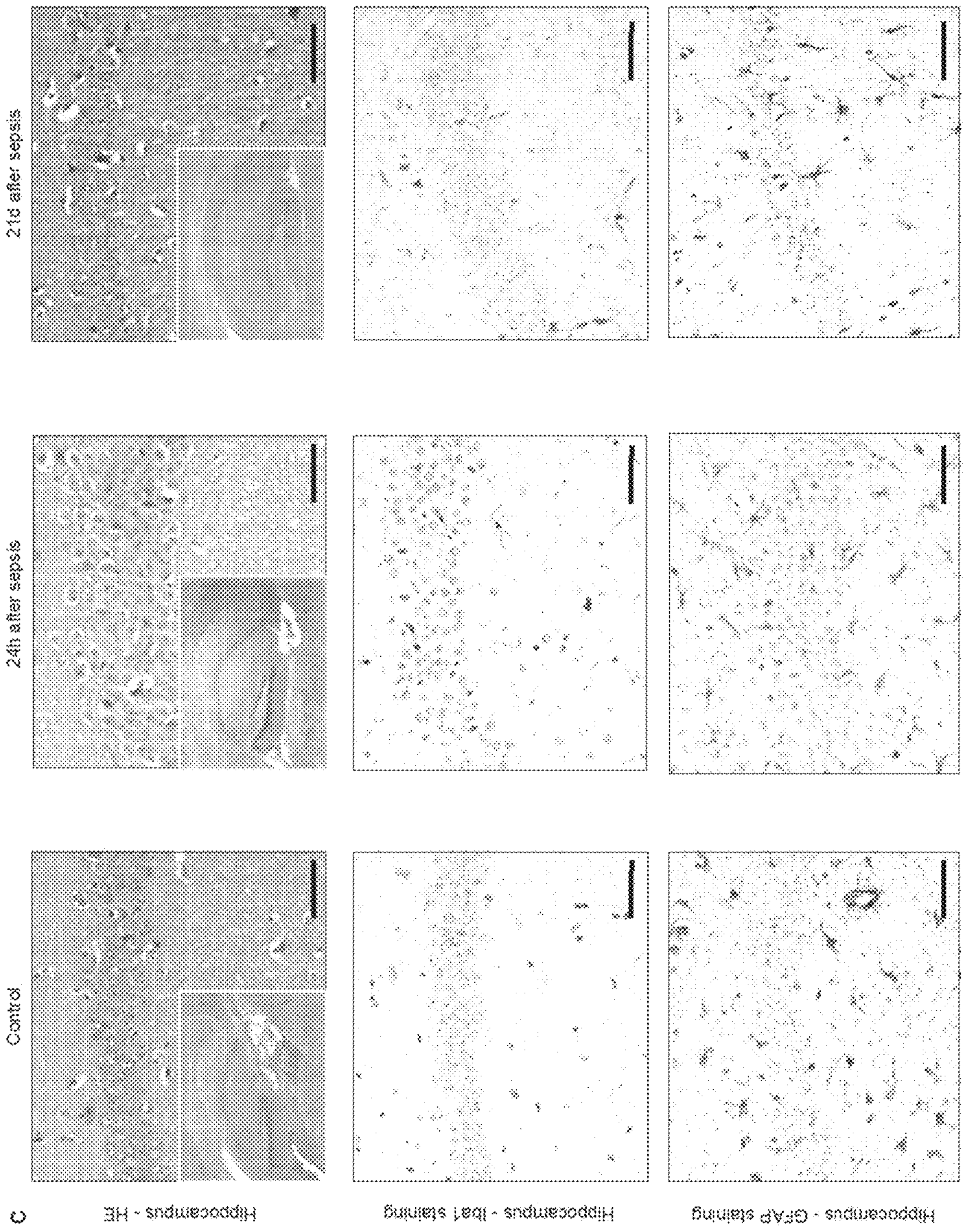

At any timepoints (24 h or 21 days after sepsis), analyses by an independent neuropathologist on haematoxylin and eosin (HE) brain sections revealed no evident histopathological abnormalities (FIG. 6*c*). However, we analyzed their morphology using the transgenic CX3CR1$^{GFP/+}$ model, applying an innovative powerful and precise method of cell modelization that has been recently described (Verdonk et al., 2016b). Compared to control mice, CLP induced early changes (i.e. from 6 h) in microglial morphology and density in the four major brain regions (frontal cortex, hippocampus, striatum and cerebellum) (FIG. 1*a*, *b*).

Figure 1D:
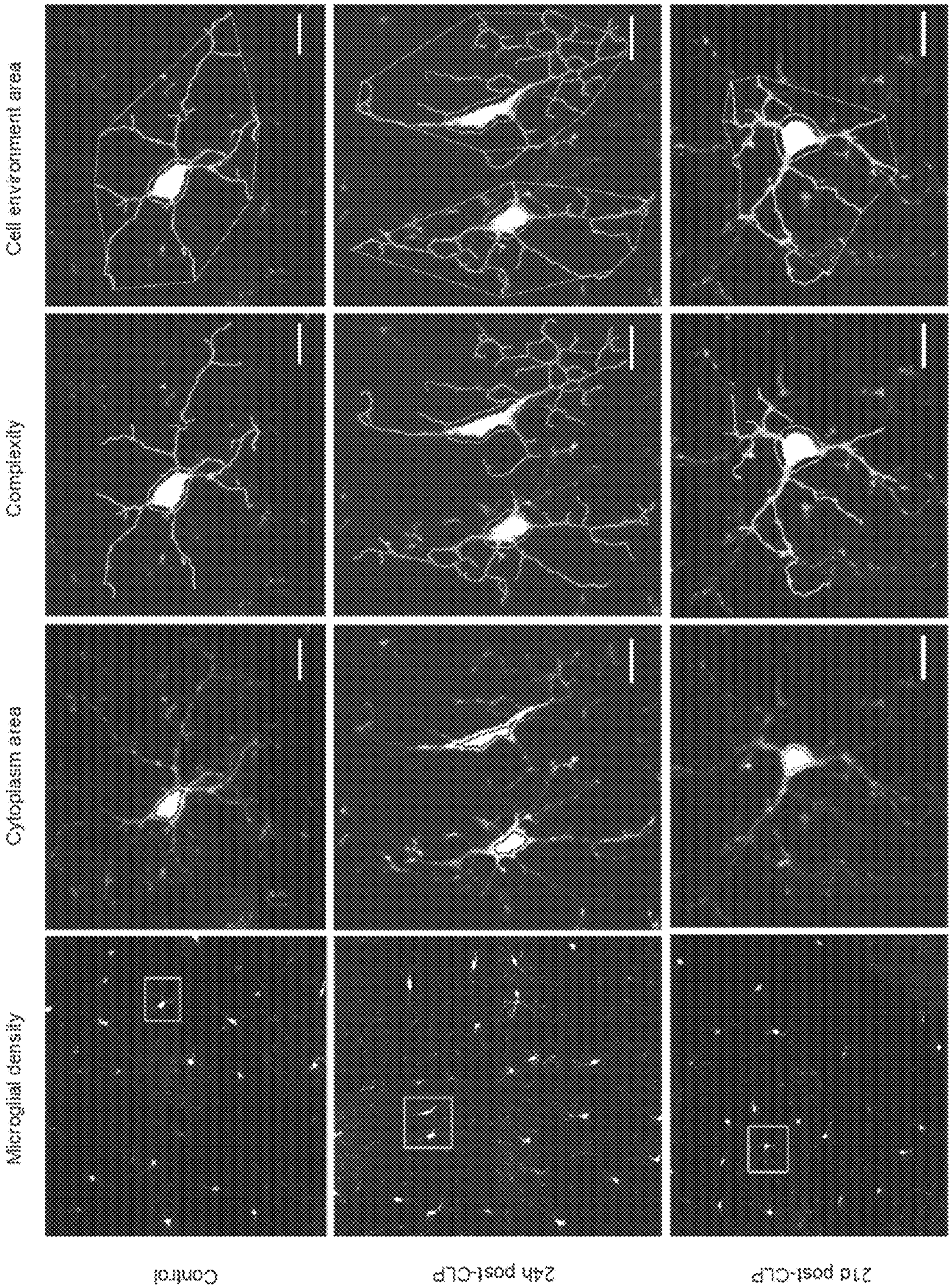

Twenty-one days after CLP in survivors, microglial cells still presented higher median cell body (26.3 vs 21.8 $\mu m^2$, p=0.001, respectively), and cytoplasm (179 vs 66.1 $\mu m^2$, p<0.0001, respectively) areas compared to control group. Microglial density in the brain tissue (4,744 vs 2,509 cells/12.68 $mm^2$, p=0.0026, respectively) and the percentage of amoeboid cells (37 vs 9 cells/12.68 $mm^2$, p=0.005, respectively) remained also significantly different in sepsis survivors than in the control group (FIG. 1*a*). Following previous study (Verdonk et al., 2016a) we showed that the regional distribution of microglial sub-populations varied significantly between the control and sepsis survivors' groups (p<0.0001) (FIG. 1*c*-*d*).

Immuno-Phenotype Level

In comparison to control mice, CLP induces an over-transcription of IL1β but also of M1 phenotype markers such as CD32 gene and M2b phenotype marker such as IL1-RA in the 24 first hours, corresponding to an early cytotoxic microglial phenotype.

Twenty-one days after CLP, while M2b markers were back to baseline, the microglial M1 and M2a phenotypes were predominant with overexpression of Ptgs2 and LGALS3 in sepsis survivors in comparison to control mice (Table 1) suggesting a neurotoxic microglial phenotype.

TABLE 1

Gene expression profiles of microglial phenotype markers relative to control group

| Phenotype | Control | H6 | H12 | H24 | D21 | ANOVA | Control vs H6 | Control vs H12 | Control vs H24 | Control vs D21 |
|---|---|---|---|---|---|---|---|---|---|---|
| M1 phenotype | | | | | | | | | | |
| CD32 | 1.02 | 1.04 | 1.895 | 1.88 | 1.11 | <0.0001 | ns | ns | 0.034 | ns |
| CD86 | 0.99 | 1.11 | 1.86 | 1.895 | 1.36 | 0.0066 | ns | 0.0414 | 0.0206 | ns |
| Ptgs2 | 1.175 | 2.2 | 2.595 | 3.055 | 2.22 | 0.0306 | ns | ns | 0.0489 | 0.0368 |
| M2a phenotype | | | | | | | | | | |
| LGALS3 | 0.995 | 1.08 | 1.93 | 2.45 | 2.6 | 0.0161 | ns | ns | ns | 0.0289 |
| IGF1 | 0.99 | 0.93 | 0.99 | 0.615 | 1.72 | ns | NA | NA | NA | NA |
| CD206 | 1 49 | 0.68 | 2.05 | 1.775 | 1 48 | ns | NA | NA | NA | NA |
| MM phenotype | | | | | | | | | | |
| IL-1β | 0.98 | 20.31 | 4.195 | 5.32 | 2.23 | 0.0012 | 0.0005 | ns | ns | ns |
| IL-4α | 0.895 | 0.6 | 1.32 | 1.98 | 0.56 | 0.0123 | ns | ns | ns | ns |
| SOCS3 | 1 | 1.13 | 0.86 | 1.2 | 0.41 | ns | NA | NA | NA | NA |
| **Cytokines** | **Control** | **H6** | **H12** | **H24** | **D21** | **ANOVA** | **Control vs H6** | **Control vs H12** | **Control vs H24** | **Control vs D21** |
| Pro-inflammatory | | | | | | | | | | |
| IL1β | 1.18 | 0.68 | 2.495 | 3.335 | 1.53 | 0.0122 | ns | ns | 0.0414 | ns |
| TNFα | 1.155 | 0.54 | 1.915 | 2.56 | 0.47 | 0.0069 | ns | ns | ns | ns |
| Anti-inflarnmatory | | | | | | | | | | |
| IL4 | 0.895 | 0.6 | 1.32 | 1.98 | 0.56 | ns | NA | NA | NA | NA |
| CD206 | 1.09 | 1.08 | 1.03 | 0.805 | 1.21 | ns | NA | NA | NA | NA |

Quantification of pro-inflammatory markers (Cd32, Cd86 and Ptgs2 mRNA), anti-inflammatory markers (Lgals3, Igf1 and Cd206 mRNA), immuno-regulator markers (Il1rn, 114ra and Socs3 mRNA) and cytokine mRNA by RT-qPCR in Cd11b+ microglial cells magnetically sorted from mice brain at different time points after induction of sepsis. Data represent median values of n=5 mice per group. Kruskal Wallis tests were performed to compare the Control (non-operated but anesthetized), H6, H12, H24 and D21 groups. The last five columns indicate p values. In case of statistical significance, multiple comparisons were performed and indicated on the table. ns: not significant. Data are represented as fold changes using the 2-ΔΔCT method.

Sepsis Induces Lasting Metabolic Reprogramming in Microglial Cells

To gain insight into how sepsis induces changes in the microglial metabolic state, we assessed the levels of two major reactive species, namely ROS $H_2O_2$ and RNS peroxynitrite, which relative values and the so-called nitroso (RNS)-redox(ROS) balance are affected in several stress-induced conditions and pathologies (Doridot et al., 2014; Cortese-Krott et al., 2017; Chatre et al., 2015). The cumulative ROS and RNS signal, detected with the fluorogenic dye CellROX that is oxidized by both ROS and RNS, decreased with CLP in microglial cells since 12 hours and remained below control levels 21 days after sepsis (FIG. 2*a*).

Figure 7A:
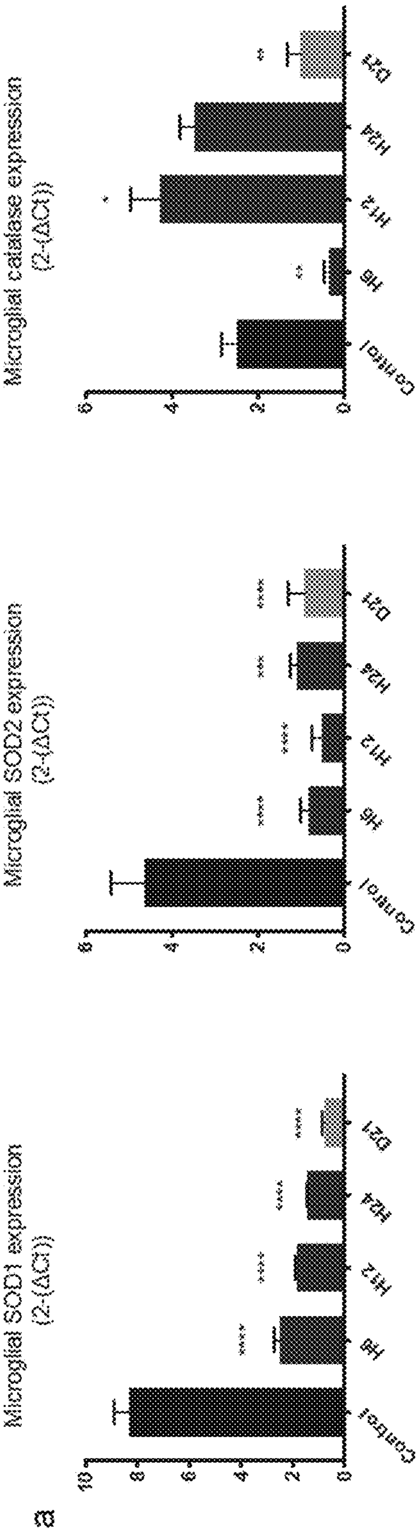

In a same manner, the expression of antioxidant defense genes NRF2 transcription factor (nuclear factor erythroid 2-related factor 2), superoxide dismutases 1 and 2 (SOD1 and mitochondrial SOD2) and catalase, as well the SOD activity decreased and remained below control levels as soon as 6 hours and up to 21 days after sepsis, suggesting that contained or lower levels of ROS and RNS in these cells was likely due to reduced generation rather than active antioxidant activity (FIG. 2*a*; FIG. 7*a*)). Therefore, in CLP mice, reprogramming of the nitroso-redox balance and of the antioxidant defense in microglial cells may reflect metabolic changes including in the major reactive species source which are the mitochondria (Sies and Jones, 2020).

Figure 2A:
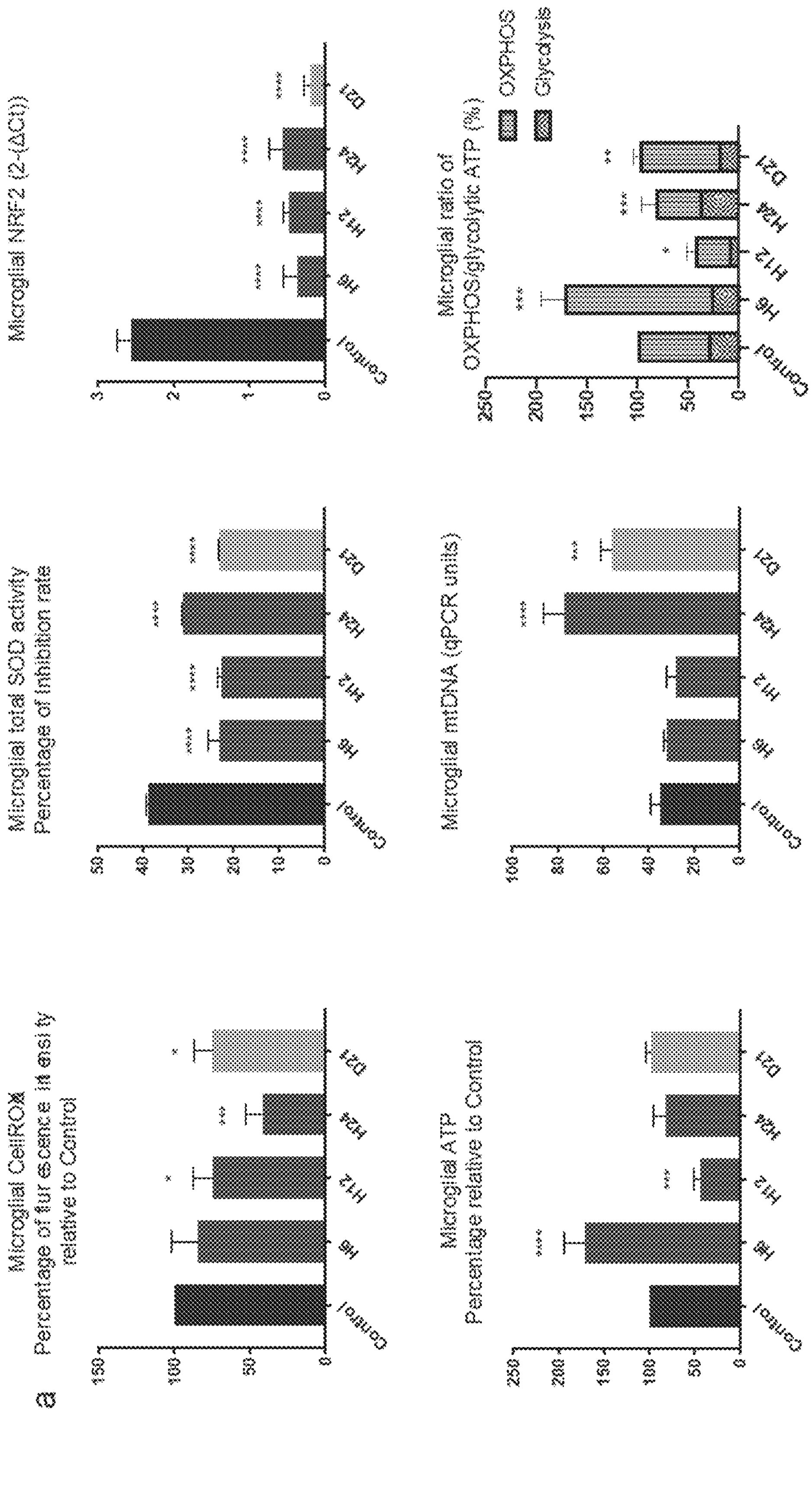
Figure 7B:
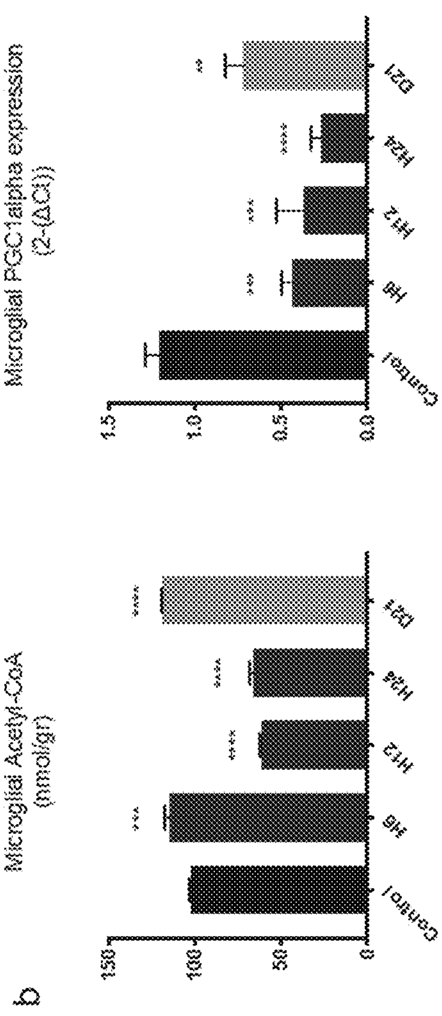
Figure 7C:
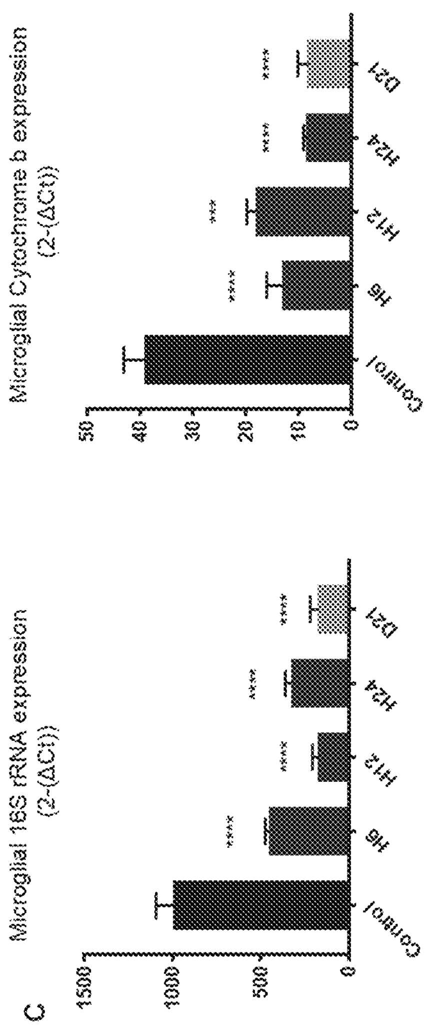

In CLP mice, 6 h after sepsis microglial cells display a larger ATP production than cells from control mice (FIG. 2*a*). As the proportion of glycolysis strongly decreases 6 h after sepsis, this ATP production is largely due to mitochondrial oxidative phosphorylation (OXPHOS) (FIG. 2*a*). Total ATP level returns to normal at 24 h post-sepsis associated with glycolysis upregulation and thus OXPHOS reduction (FIG. 2*a*). However, lately at 21 days, microglial cells are shown to produce their ATP mostly due to OXPHOS over-activation as glycolysis is reduced (FIG. 2*a*). Reflecting bioenergetic metabolism dynamics through the coordination of glycolysis with OXPHOS, the central metabolic intermediate Acetyl-CoA whose abundance reflects the bioenergetic state was measured in CLP mice (Pietrocola et al., 2015). Indeed, from 6 h to 21 days after sepsis, the profound dysregulation of Acetyl-Coa levels confirms that sepsis induces lasting metabolic reprogramming in microglial cells (FIG. 7*b*). Such rapid and profound metabolic reprogramming through mitochondria suggests a major sepsis-induced mitochondrial remodeling including mitochondrial biogenesis, metabolism markers (PGC1 alpha), mitochondrial DNA (mtDNA) and RNA (mtRNA) (Doridot et al., 2014; Rocheteau et al., 2015; Chatre et al., 2015). Once again, the expression of PGC1 alpha decreases in microglia during sepsis and until 21 days (FIG. 7*b*). Finally, from 24 h to 21 days after sepsis, the mtDNA content strongly increases while, at the same time, the levels of mtRNAs 16S and CytB strongly decrease (FIG. 2*a*; FIG. 7*c*). Thus, all these metabolic data confirm that sepsis induces from early stage to 21 days in survivors from sepsis a major metabolic reprogramming in microglial cells with ultimately a metabolic shift towards mitochondrial OXPHOS.

Figure 2B:
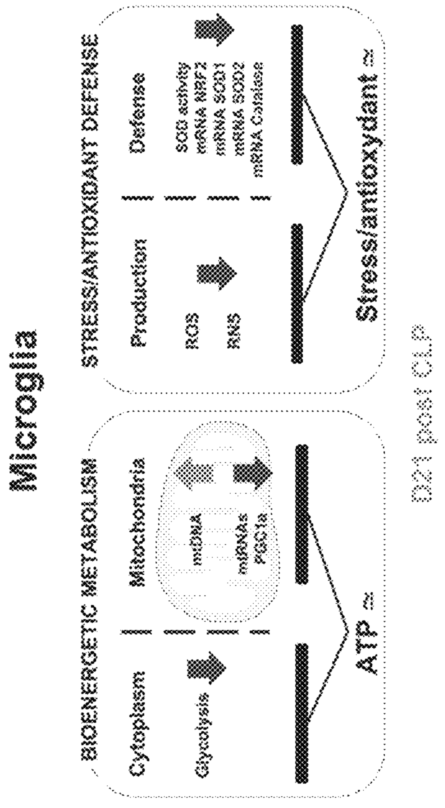
Figure 2C:
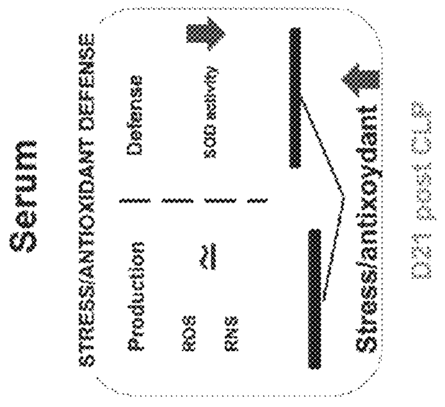

Altogether, from early stages to 3 weeks after sepsis in survivors, microglial cells display a strong reduction in oxidative and nitrosative stress associated with a strong reduction in antioxidant defense and with a major bioenergetic metabolism reprogramming leading to an overactivation of mitochondrial OXPHOS in survivors. (FIG. 2*b*).

Figure 2D:
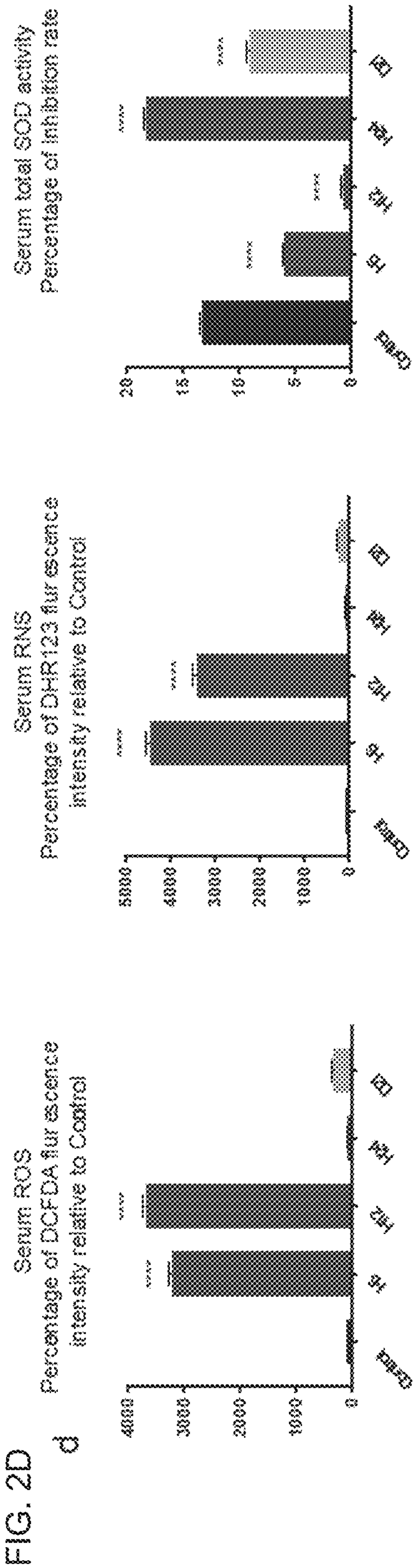

As a second step, we questioned whether this microglia reprogramming is associated with a deleterious nitroso-redox stress coming from the microglial environment and especially from the blood (FIG. 2*b-d*)) (Lauro and Limatola, 2020; Devanney et al., 2020). Indeed, during the first 12 h after sepsis, serum from CLP mice exhibited higher levels of ROS $H_2O_2$, higher levels of RNS peroxynitrite and lower levels of SOD activity compared with serum from control mice (FIG. 2*d*). Lately, at 21 days after sepsis, the SOD activity remained lower in CLP mice. Altogether, our data suggest that the initiation of nitroso-redox balance, antioxidant defense and metabolic reprogramming in microglial cells may be caused by a rapid and deleterious systemic nitroso-redox accumulation. Thus, challenging this microglial reprogramming by directly targeting together ROS, RNS peroxynitrite and SOD activity in blood may be of particular interest and a potential powerful therapy to counteract sepsis-induced microglia alterations.

MnTBAP Counteracts the Sepsis-Induced Metabolic Reprogramming in Microglial Cells To address this hypothesis, we tested early injection of MnTBAP, a ROS/RNS modulator superoxide dismutase (SOD) mimetic, to reverse sepsis-induced microglial reprogramming, cellular and cognition alterations.

Figure 3A:
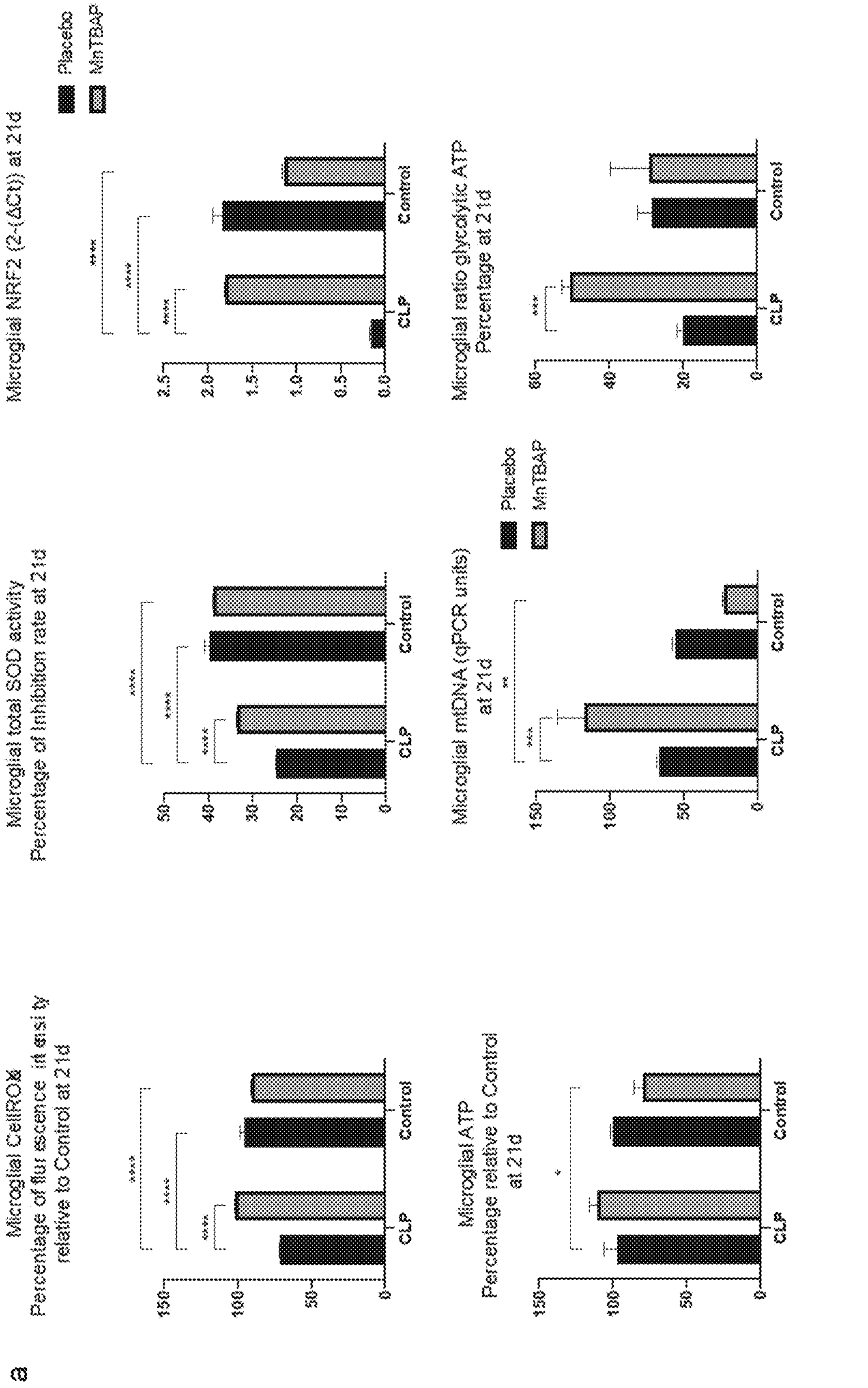
Figure 8A:
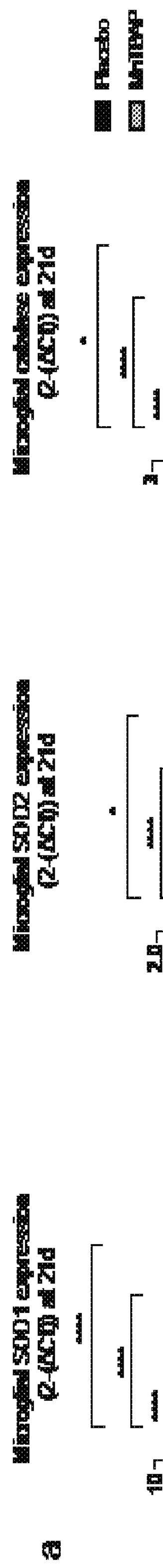
Figure 8B:
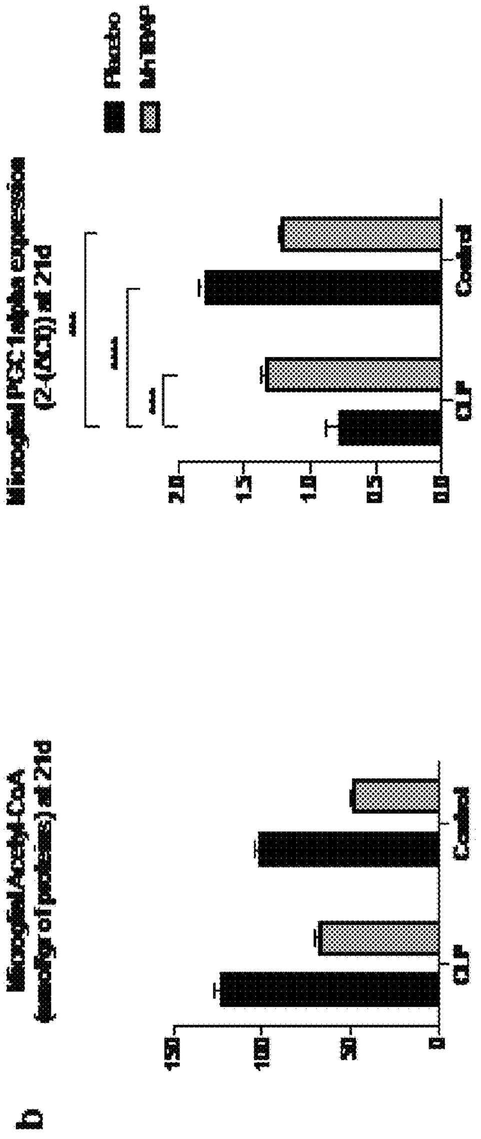
Figure 8C:
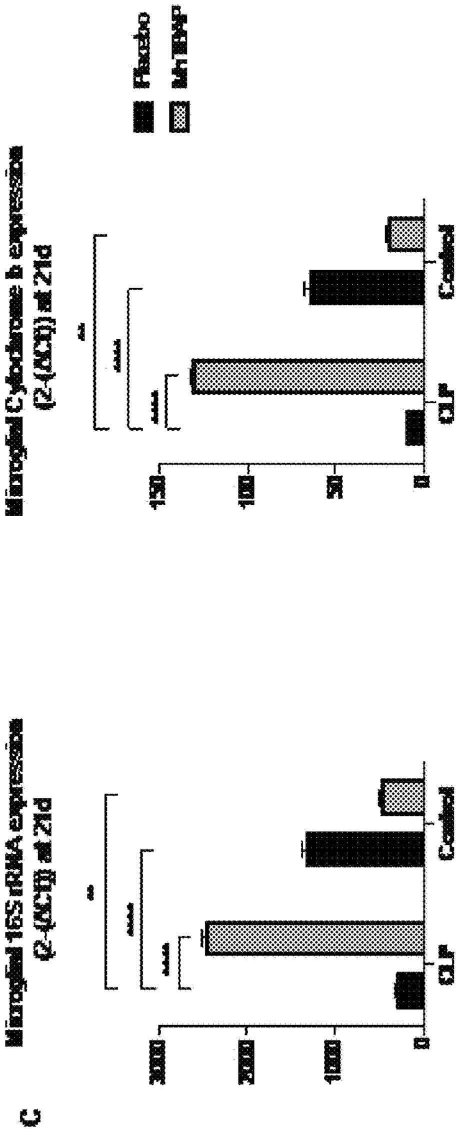

Interestingly, MnTBAP in control mice slightly reduced microglial ROS/RNS levels (p=0.005), SOD1 (p<0.0001), SOD2 (p=0.0003), catalase (p=0.0036) and NRF2 (p<0.0001) expression, did not affect microglial SOD activity, ATP generation neither glycolysis contribution, reduced microglial PGC1 alpha expression (p=0.0003), mtDNA content (0.01), mtRNAs 16S (p<0.0001) and CytB (p<0.0001 levels compared with Control-placebo mice (FIG. 3*a*; FIG. 8*a-c*).

A significant CLP vs control×MnTBAP vs placebo interaction was observed in all the studied microglial metabolic parameters except for the acetyl-coA levels. MnTBAP counteracted the effects of CLP on ROS/RNS levels, SOD activity, expression of SOD1, SOD2, catalase and NRF2 transcripts by significantly increasing them but all of them remained different from the Control-Placebo group. MnTBAP also significantly induced a strong microglial metabolic shift from mitochondrial OXPHOS to glycolysis, a strong mtDNA content increase, an increase in PGC1 alpha expression and a strong increase in mtRNAs 16S and CytB expression in CLP mice compared to CLP-placebo mice (FIG. 3*a*; FIG. 8*a-c*).

Thus, MnTBAP successfully reversed the sepsis-induced microglial reprogramming and alterations in CLP mice, 21 days after sepsis (FIG. 3*b*).

MnTBAP Also Counteracts the Sepsis-Induced Alterations in Brain

Then, we checked whether the sepsis-induced alterations in the brain microglial cells are counteracted by the injection of MnTBAP in a same manner than within the microglial cells at 21 days after sepsis.

Interestingly and differently from microglial cells, MnTBAP in control mice induced an increase in ROS/RNS levels (p=0.001), in SOD activity (p<0.0001), in SOD1 (p<0.0001), SOD2 (p<0.0001) and NRF2 expression (p<0.0001), in ATP production (p<0.0001), in mtDNA content (p<0.0001) associated with an increase in mtRNAs 16S (p=0.0005) and CytB (p=0.04) levels, did not affect catalase and PGC1 alpha expression neither Acetyl-coA levels in comparison to Control-placebo mice.

Figure 4B:
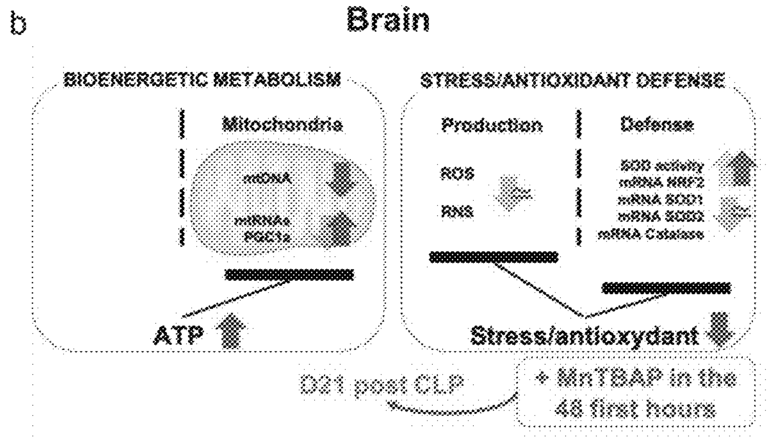
Figures 9A, 9B, 9C:
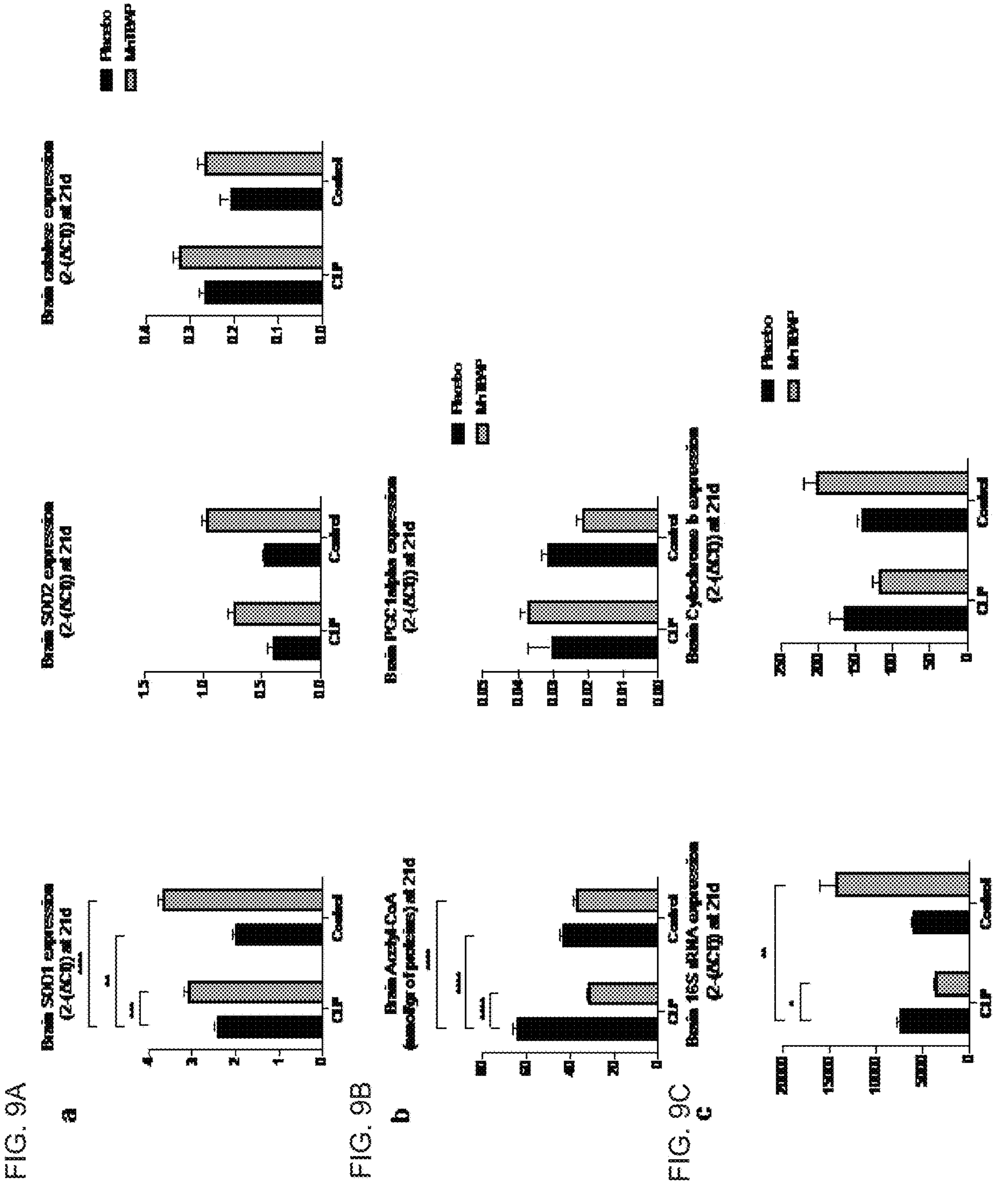

In the brain, a significant CLP vs control×MnTBAP vs placebo interaction was also observed in a majority of brain metabolic parameters. As in microglial cells, MnTBAP counteracted the sepsis-induced alterations in brain on ROS/RNS and SOD activity levels, SOD1 expression, ATP production by significantly increasing them but all of them remained different from the Control-Placebo group. Conversely, MnTBAP strongly decreased acetyl-coA and mtRNAs 16S levels (FIG. 4*a*; FIG. 9*a-c*). Thus, MnTBAP counteracted the sepsis-induced brain alterations in CLP mice (FIG. 4*b*).

Thus, as for microglial cells, MnTBAP is inducing a global brain remodeling in terms of nitroso-redox balance, antioxidant defense and bioenergetic metabolism related to mitochondrial function. (FIG. 4*a*; FIG. 9*a-c*)

MnTBAP Inhibits CLP-Induced Long Term Microglial Neurotoxic Polarization

MnTBAP alone did not alter the microglial immunophenotype. There was a significant CLP vs control×MnTBAP vs placebo interaction for CD86 (F (1, 16)=6.637, p=0.0203), Ptgs2 (F (1, 16)=6.122,p=0.0249), SOCS3 (F (1, 16)=5.859, p=0.0278), IL-1RA (F (1, 16)=4.507, p=0.0497) and Lgals3 (F (1, 16)=5.605, p=0.0309) gene expression in extracted microglial cells. In septic mice, MnTBAP significantly reduced Ptgs2 (p=0.026) (M1 maker) and IL1RA (p=0.047) (M2b marker) transcripts compared to the placebo group and these levels did not differ from the Control-placebo group. In a same manner, CLP-MnTBAP group presented a significantly lower IL1β expression than the CLP-placebo group (p=0.01) that did not differ from the Control-placebo group (Table 2). The CLP-MnTBAP group presented with a significantly lower Lgals3 (M2a) gene expression than the CLP-placebo group (p=0.023) and did not differ from transcript levels in the Control-placebo group. (Table 2). Altogether these results indicate that MnTBAP shifts microglial immunoprofile from a neurotoxic toward a neuroprotective phenotype in septic mice.

On a tissue level, the 23 measured cytokines did not show any CLP vs control×MnTBAP vs placebo interaction, or difference linked to condition or treatment between the groups (Table 4).

TABLE 2

| Gene expression profiles of microglial immuno-phenotype markers at 21 days relative to the Control/Placebo group | | | | | | | |
|---|---|---|---|---|---|---|---|
| Phenotype | Control/ placebo | Control/ MnTBAP | CLP/ Placebo | CLP/ MnTBAP | Interaction | Condition | Treatment |
| M1 phenotype | | | | | | | |
| CD32 | 1.07 | 0.81 | 0.71 | 0.85 | ns | ns | ns |
| CD86 | 1.015 | 0.77 | 0.8 | 0.85 | 0.0203 | ns | ns |
| Ptgs2 | 0.435 | 1.22 | 7.67 | 1.33 | 0.0249 | ns | ns |
| M2a phenotype | | | | | | | |
| Lgals3 | 0.74 | 1.06 | 2.85 | 1.035 | 0.0309 | 0.0215 | ns |
| IGF1 | 0.88 | 0.95 | 0.97 | 1.09 | ns | ns | ns |
| CD206 | 1.08 | 0.63 | 1 | 0.705 | ns | ns | ns |
| M2b phenotype | | | | | | | |
| IL1rn | 0.725 | 0.74 | 2.07 | 1.22 | 0.0497 | ns | ns |
| Il4raα | 0.53 | 1.18 | 2.13 | 0.51 | ns | ns | ns |
| Socs3 | 1.01 | 1.14 | 1.29 | 0.575 | 0.0278 | ns | ns |
| Cytokines | Control/ placebo | Control/ MnTBAP | CLP/ Placebo | CLP/ MnTBAP | Interaction | Condition | Treatment |
| Pro-inflammatory | | | | | | | |
| IL1β | 1.18 | 0.81 | 2.01 | 1.065 | 0.0081 | 0.0271 | 0.0458 |
| Anti-inflammatory | | | | | | | |
| IL10 | 0.74 | 1.56 | 3.3 | 1.69 | ns | ns | ns |

Quantification of pro-inflammatory markers (CD32, CD86 and Ptgs2 mRNA), anti-inflammatory markers (Lgals3, IGF1 and CD206 mRNA) and immuno-regulator markers (IL1-RA, IL4-Rα and SOCS3 mRNA) by RT-qPCR in Cd11b+ microglial cells magnetically sorted from the brain at 21 days. Control mice were non-operated but anesthetized. The data shown represent median values of n=5 mice per group. Two-way analyses of variance (ANOVAs) CLP vs Control×MnTBAP vs Placebo were performed. The "interaction" column indicates if an interaction between the condition (CLP or Control) and the treatment (MnTBAP or Placebo) could affect the results, the "Condition" and "Treatment" columns indicate if the condition (CLP or Control) or the treatment (MnTBAP or Placebo) could by itself affect the results. ns: not significant. Data are represented as fold changes using the 2-ΔΔCT method.

TABLE 4

| Brain Cytokines | Control/ placebo | Control/ MnTBAP | CLP/ Placebo | CLP/ MnTBAP | Interaction | Condition | Treatment |
|---|---|---|---|---|---|---|---|
| IL-1α | 6.05 | 6.19 | 2.97 | 3.36 | ns | ns | ns |
| IL-1β | 3.98 | 3.50 | 2.70 | 3.22 | ns | ns | ns |
| IL-6 | 1.14 | 1.30 | 0.90 | 0.84 | ns | ns | ns |
| IL-10 | 4.88 | 3.69 | 3.94 | 4.43 | ns | ns | ns |
| IL-12(p40) | 75.82 | 62.34 | 72.95 | 79.42 | ns | ns | ns |
| IL-12(p70) | 42.93 | 33.39 | 34.38 | 34.35 | ns | ns | ns |
| IL-13 | 23.36 | 19.25 | 33.56 | 29.31 | ns | ns | ns |
| IL-17 | 9.21 | 7.49 | 8.04 | 8.34 | ns | ns | ns |
| GM-CSF | 3.19 | 3.63 | 5.46 | 5.74 | ns | ns | ns |
| IFN-g | 10.27 | 9.17 | 9.50 | 8.85 | ns | ns | ns |
| KC | 41.16 | 66.11 | 110.11 | 70.42 | ns | ns | ns |
| MCP1 | 86.45 | 85.62 | 119.28 | 98.24 | ns | ns | ns |
| MIP1a | 8.92 | 7.36 | 6.74 | 7.18 | ns | ns | ns |
| TNFα | 89.89 | 99.51 | 81.68 | 75.05 | ns | ns | ns |
| RANTES | 10.71 | 10.38 | 8.71 | 8.19 | ns | ns | ns |

Cytokine and Chemokine Levels in Mice Brain at 21 Days After CLP in Survivors The data represent the level of protein expression in pg $mg^{-1}$ of brain tissue using Luminex®. Control mice were non-operated but anesthetized. Median values of n=5 mice per group are represented. Two-way analyses of variance (ANOVAs) CLP vs Control×MnTBAP vs Placebo were performed. The "interaction" column indicates if an interaction between the condition (CLP or Control) and the treatment (MnTBAP or Placebo) could affect the results, the "Condition" and "Treatment" columns indicate if the condition (CLP or Control) or the treatment (MnTBAP or Placebo) could by itself affect the results. ns: not significant.

MnTBAP Restores CLP-Induced Long-Term Cognitive Impairment

In the Novel Object Recognition test (NOR) a significant CLP vs control×MnTBAP vs placebo interaction was observed (F(1,29)=13.15, p=0.0011) for the exploration time. Indeed. the time of new object exploration (mean difference 10%, p=0.006) was was significantly greater in the CLP-MnTBAP group than in the CLP-placebo group (mean difference 27%, p=0.0001). Importantly, it did not statistically differ between the Control-MnTBAP and Control-placebo groups (mean difference 7%, p=0.99) (FIG. 4*c*).

Figure 4C:
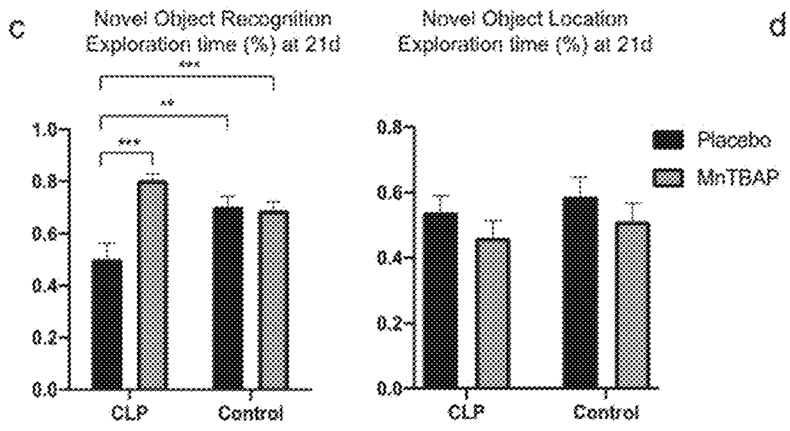

Conversely, the Novel Object Location test (NOL) revealed no significant CLP vs control×MnTBAP vs placebo interaction (F(1,29)=0.0007, p=0.98) for the exploration time (FIG. 4*c*).

MnTBAP Significantly Reduces CLP-Induced Mortality

Figure 4D:
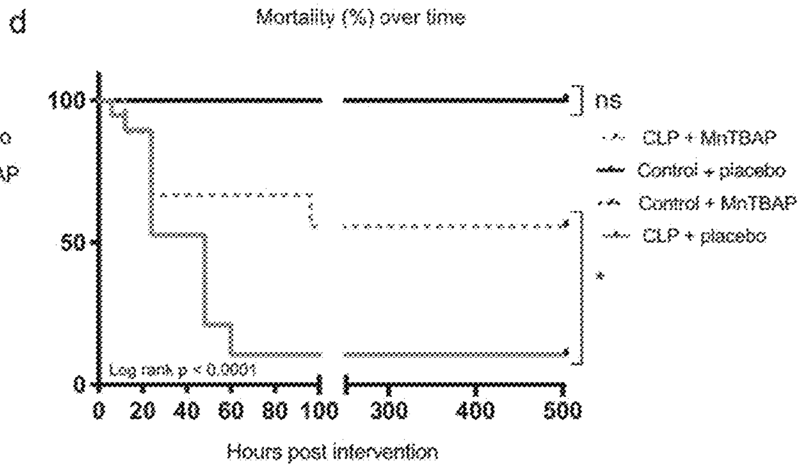

A significant improvement in survival rate of MnTBAP mice compared with placebo mice was found after CLP (FIG. 4*d*). In CLP-placebo mice, 52% were alive at 24 h and 10.5% at 21 days after CLP, compared to 66% at 24 h and 55% at 21 days in CLP-MnTBAP mice (p<0.0001)

MnTBAP Derivatives, Including MnTnBuOE-2-Pyp5+ and MnTE-2-Pyp5+

Tests with MnTBAP derivatives as disclosed herein, including MnTnBuOE-2-Pyp$^{5+}$ and MnTE-2-Pyp$^{5+}$, have been devised and are ongoing, using the methodology described above and herein for MnTBAP, which corresponds to an established protocol. This protocol is peritonitis induced by cecal ligation and puncture (CLP) as a model of sepsis (as disclosed in Rittirsch et al, 2009).

According to this protocol, CLP mice are randomized to receive an intraperitoneal (IP) injection of 100 μL of isotonic saline solution (NaCl 0.9%), or of MnTnBuOE-2-Pyp$^{5+}$ (BMX-001) or MnTE-2-Pyp$^{5+}$ (BMX-010) at a dose of 0.2-2 mg/kg every 12 hours for 48 hours. The dosage is adapted to the activity of the tested compounds. The skilled person can, in this respect, readily adapt dosage as needed for the effects sought. The survival is to be monitored until 21 days post-CLP, and other selected parameters as tested with MnTBAP-treated CLP mice, like the levels of serum ROS, are to be tested.

FIG. 10 depicts the results on survival of mice for administration of BMX-010 (versus placebo) hours post-CLP: BMX-010 outperforms the placebo. More specifically, FIG. 10 shows that treatment of CLP mice with 2 mg/kg of BMX-010 intra peritoneal every 12 hours during 48 hours (4 injections) resulted in more that doubles survival at 4 days post-CLP. N=12 mice C57BL6/group.

Discussion

Numerous clinical and experimental studies emphasize the role of mitochondrial dysfunction in the time-course and prognosis of sepsis (Kraft et al., 2019; Rahmel et al., 2020), but few have addressed whether metabolic changes persist after the resolution of sepsis (Arulkumaran et al., 2016; da Silva and Machado, 2017), limiting the opportunities to develop innovative preventive or curative treatments of late complications. These are characterized by development of secondary infections, high mortality and cognitive disorders at one year after sepsis (Drewry et al., 2014; Sun et al., 2016; Iwashyna et al., 2010a). In this study, we focused on the main cellular effector of the neuro-inflammation, the microglial cells as it is considered to play a key role in the translation from acute brain dysfunction toward cognitive decline in the sepsis setting (Annane and Sharshar, 2015b; Giridharan et al., 2019). Our main finding is that sepsis affects early and durably microglial cells as they have acquired, late after its resolution (i.e. day 21 from CLP), a specific morphological, immunological phenotype associated with a metabolic reprogramming. Furthermore, these long-term cellular alterations could be reversed by an early immune modulation targeting the systemic reactive oxygen species (ROS) and reactive nitrogen species (RNS) highlighting the deleterious cerebral effect of the systemic reactive oxygen/nitrogen species generated in the acute phase sepsis. To do so, we used the cecal ligation and puncture (CLP) as an extensively described model of experimental sepsis which is the most relevant to study sepsis-induced long-term cognitive alterations (Cunningham, 2011; Barichello et al., 2019).

Mitochondrial dysfunctions during and after sepsis in experimental or post-mortem human studies include morphological modifications, electron transport chain dysfunction and oxidative stress (Zhang et al., 2018) and have been described in many cells but never in microglial cells. In our model of sepsis survivors, we assessed that microglial cells exhibited a lasting impairment of nitroso-redox balance and production of ATP as well as major bioenergetic metabolism reprogramming. And since mitochondria have already been shown as involved in circulating immune cells function (Faas and de Vos, 2020), microglial cells exhibited neurotoxic immune phenotype as well as morphological alterations lately after sepsis resolution. Altogether, these results provide evidence to a physiological link between cellular metabolism and cellular function in microglial cells, which derive from the yolk sac as other erythro-myeloid progenitors. These late alterations are in line with the microglial "innate immune memory" theory that has been recently proposed as one of the precipitating of neurodegenerative diseases observed after systemic inflammation (Neher and Cunningham, 2019). This theory is based on long-lasting molecular reprogramming of microglial following inflammatory stimulus, such as single or repeated LPS injections, that results in altered microglial response to further brain insults, even after a long latent phase (Schaafsma et al., 2015).

Reduction of metabolic alterations is suggested as opportunity to improve recovery in organ function in patients who survive sepsis (Neri et al., 2016). Based on our findings and the scientific literature identifying overproduction of circulating ROS and RNS within the first 6 hours after CLP, as a biochemical hallmark of sepsis (Galley, 2011; Prauchner, 2017), we designed a randomized interventional study comparing the effects of an early intraperitoneal injection of a ROS/RNS modulator superoxide dismutase (SOD) mimetic to placebo in septic mice. Early injection of MnTBAP alleviates sepsis-induced alterations in both microglia and brain by remodeling the nitroso-redox balance, the antioxidant defense and bioenergetic metabolism including mitochondria. Importantly, in septic mice, MnTBAP induces an immune switch from neurotoxic to neuroprotective microglial phenotype, strengthening the metabolic-functional cellular link. As this drug poorly penetrates the BBB (Liu et al., 2013b) and has already been shown to lower the release of pro-inflammatory cytokines and oxidant injury in lung contusion (Suresh et al., 2013), to regulate the humoral immune response during viral infection (Crump et al., 2013), to attenuate vascular inflammation (Zhou et al., 2016), and to regulate mitochondrial metabolism in a progeroid disease (Chatre et al., 2015), we cannot exclude systemic effects on other cell-types function to explain these improvements.

Interestingly, we observed a preferential impairment of the non-spatial learning memory in survivors 21 days after CLP, involving hippocampal dorsal neurons but also other regions such as the perirhinal cortex or frontal cortex (Cohen et al., 2013). Applying an innovative and precise morphological approach to our study on four different major brain regions (frontal cortex, striatum, hippocampus and cerebellum), we emphasize the diffuse nature of these alterations at a microglial level. MnTBAP successfully restores long-term cognitive function. This confirms our hypothesis of a third oxidative/nitrosative pathway that participates to the pathophysiology of SAE and its late cognitive consequences, in addition to the neural pathway which implicated the stimulus of the vagus nerve (Ren et al., 2020), and the humoral pathway which involves the circumventricular organs (CVOs) located near neuroendocrine and neurovegetative nuclei (Heming et al., 2017). Numerous factors inherent to the brain and cerebral endothelial cells increase the brain sensitivity to oxidative/nitrosative stress such as the high neuronal oxygen consumption to maintain membrane potential, the polyunsaturated fatty acids constitutive of the neuronal membrane susceptible to lipid peroxidation and the blood brain barrier (BBB) energy-dependent transport mechanisms (Freeman and Keller, 2012). Furthermore, if brain from septic animals is liable to oxidative stress and mitochondrial dysfunction, our study clearly indicates that metabolic alterations of microglia during late stages after sepsis is singular as it differs from the one observed in the whole brain regarding antioxidant defense related to NRF2 expression and SOD activity, and mitochondrial function related to mtDNA content. In teleological point of view, this difference might be described as a microglial self-protective response to a systemic insult to avoid further intracellular damage and to maintain microglia for further activities when microglia activation will be engaged.

Combined microglial and brain effects of MnTBAP might explain the significant reduction of mortality in our experimental model. SAE has been described as an independent risk factor of mortality (Ren et al., 2020) due to brain cells apoptosis within autonomic centers (Sharshar et al., 2003; Semmler et al., 2007). As a result, early abolition of the cough reflex and oculocephalogyric response, two major brainstem reflexes, in critically ill patients was independently associated with increased ICU mortality (Sharshar et al., 2011). By reversing the metabolic impairment, MnTBAP might increase the brain cells survival and thus reduces mortality and long-term cognitive impairments in septic mice.

In conclusion, sepsis impaired durably microglial cells that acquired morphological and immunologic markers of activated and cytotoxic phenotypes combined with down-regulation of both the nitroso-redox stress and a mitochondrial metabolic reprogramming. This late dysfunction results from early systemic reactive oxygen/nitrogen species generation during sepsis and might contribute to development of neurocognitive disorders. Our study provides an insight into the role of mitochondrial dysfunction in the brain "'innate immune memory" but also into the relationship between neuro-inflammation and the pathophysiology of SAE and its consequences. In perspective, our results pave the way to redefining and deeply understanding microglia role in post-sepsis cognitive disorders, with implications for innovative therapeutic options in sepsis and more largely in neurodegenerative disorders.

Conclusions

In the course of their investigations, the inventors showed that reactive oxygen species (ROS) and reactive nitrogen species (RNS), the nitroso-redox species, as well as markers of systemic inflammation accumulate rather early in the plasma in the course of a sepsis event. In parallel, microglial cells have been found to be reactive to the inflammatory environment and to acquire a particular morphologic, immunologic, and metabolic phenotype that persists after the resolution of sepsis. These cells also engaged an autophagic activity and epigenetic reprogramming. Thus, the inventors hypothesized that microglial cells are activated shortly after sepsis, and this "priming" might contribute to development of neurodegeneration.

Furthermore, SAE (sepsis-associated encephalopathy) is an independent risk factor of long-term cognitive and psychological impairments. It is not related to direct brain infection but mainly to a neuro-inflammatory process of which microglial cells are a key effector.

So far, the post-sepsis microglial functional status and impact on cognitive capacities have been scantly assessed, thereby limiting the therapeutic strategies.

Using a mouse model of sepsis survival, it has been shown herein that 21 days after sepsis, microglial cells exhibit morphological and immunologic markers of activated and cytotoxic phenotypes combined with downregulation of both the nitroso-redox stress and the antioxidant defense, and a mitochondrial metabolic reprogramming. These microglial changes were associated with cognitive dysfunction and both reversed after intraperitoneal injection of a reactive oxygen/nitrogen species (ROS/RNS) modulator superoxide dismutase (SOD) mimetic (MnTBAP) within the early stages of sepsis. MnTBAP also significantly reduced mortality in septic mice. In conclusion, sepsis-associated cognitive impairment is partly related to protracted metabolic-related microglial dysfunction, which results from systemic reactive oxygen/nitrogen species generated in the acute phase of sepsis. The findings reported herein provide new pathophysiological insights and of SAE but also open new therapeutic perspectives.

REFERENCES

Annane, D., and T. Sharshar. 2015a. Cognitive decline after sepsis. Lancet Respir. Med. doi:10.1016/S2213-2600(14)70246-2.

Annane, D., and T. Sharshar. 2015b. Cognitive decline after sepsis. *Lancet. Respir. Med.* 3:61-9. doi:10.1016/S2213-2600(14)70246-2.

Arulkumaran, N., C. S. Deutschman, M. R. Pinsky, B. Zuckerbraun, P. T. Schumacker, H. Gomez, A. Gomez, P. Murray, and J. A. Kellum. 2016. Mitochondrial function in sepsis. Shock. doi:10.1097/SHK.0000000000000463.

Barichello, T., P. Sayana, V. V. Giridharan, A. S. Arumanayagam, B. Narendran, A. Della Giustina, F. Petronilho, J. Quevedo, and F. Dal-Pizzol. 2019. Long-Term Cognitive Outcomes After Sepsis: a Translational Systematic Review. *Mol. Neurobiol.* 56:186-251. doi:10.1007/s12035-018-1048-2.

Bozza, F. A., J. C. D'Avila, C. Ritter, R. Sonneville, T. Sharshar, and F. Dal-Pizzol. 2013. Bioenergetics, mitochondrial dysfunction, and oxidative stress in the pathophysiology of septic encephalopathy. Shock. 39 Suppl 1:10-6. doi:10.1097/SHK.0b013e31828fade1.

Chatre, L., D. S. F. Biard, A. Sarasin, and M. Ricchetti. 2015. Reversal of mitochondrial defects with CSB-dependent serine protease inhibitors in patient cells of the progeroid Cockayne syndrome. *Proc. Natl. Acad. Sci. U. S. A.* 112:E2910—E2919. doi:10.1073/pnas.1422264112.

Chhor, V., T. Le Charpentier, S. Lebon, M.-V. Oré, I. L. Celador, J. Josserand, V. Degos, E. Jacotot, H. Hagberg, K. Sävman, C. Mallard, P. Gressens, and B. Fleiss. 2013. Characterization of phenotype markers and neuronotoxic potential of polarised primary microglia in vitro. *Brain. Behay. Immun.* 32:70-85. doi:10.1016/j.bbi.2013.02.005.

Cohen, S. J., A. H. Munchow, L. M. Rios, G. Zhang, H. N. Ásgeirsdóttir, and R. W. Stackman. 2013. The rodent hippocampus is essential for nonspatial object memory. *Curr. Biol.* doi:10.1016/j.cub.2013.07.002.

Cortese-Krott, M. M., A. Koning, G. G. C. Kuhnle, P. Nagy, C. L. Bianco, A. Pasch, D. A. Wink, J. M. Fukuto, A. A. Jackson, H. Van Goor, K. R. Olson, and M. Feelisch. 2017. The Reactive Species Interactome: Evolutionary Emergence, Biological Significance, and Opportunities for Redox Metabolomics and Personalized Medicine. *Antioxidants Redox Signal*. 27:684-712. doi:10.1089/ars.2017.7083.

Courtright, K. R., L. Jordan, C. M. Murtaugh, Y. Barrón, P. Deb, S. Moore, K. H. Bowles, and M. E. Mikkelsen. 2020. Risk Factors for Long-term Mortality and Patterns of End-of-Life Care Among Medicare Sepsis Survivors Discharged to Home Health Care. *JAMA Netw. open.* doi:10.1001/jamanetworkopen.2020.0038.

Crump, K. E., P. K. Langston, S. Rajkarnikar, and J. M. Grayson. 2013. Antioxidant Treatment Regulates the Humoral Immune Response during Acute Viral Infection. *J. Virol.* doi:10.1128/jvi.02714-12.

Cunningham, C. 2011. Experimental models of cognitive dysfunction in infection and critical illness. In Brain Disorders in Critical Illness: Mechanisms, Diagnosis, and Treatment. Cambridge University Press. 97-107.

Cunningham, C., S. Campion, K. Lunnon, C. L. Murray, J. F. C. Woods, R. M. J. Deacon, J. N. P. Rawlins, and V. H. Perry. 2009. Systemic inflammation induces acute behavioral and cognitive changes and accelerates neurodegenerative disease. *Biol. Psychiatry*. 65:304-12. doi:10.1016/j.biopsych.2008.07.024.

Devanney, N. A., A. N. Stewart, and J. C. Gensel. 2020. Microglia and macrophage metabolism in CNS injury and disease: The role of immunometabolism in neurodegeneration and neurotrauma. *Exp. Neurol.* doi:10.1016/j.expneurol.2020.113310.

Doridot, L., L. Châtre, A. Ducat, J. L. Vilotte, A. Lombès, C. Méhats, S. Barbaux, R. Calicchio, M. Ricchetti, and D. Vaiman. 2014. Nitroso-redox balance and mitochondrial homeostasis are regulated by STOX1, a pre-eclampsia-associated gene. *Antioxidants Redox Signal.* 21:819-834. doi:10.1089/ars.2013.5661.

Drewry, A., N. Samra, L. Skrupky, B. Fuller, S. Compton, and R. Hotchkiss. 2014. Persistent lymphopenia after diagnosis of sepsis predicts mortality. Shock. doi:10.1097/SHK.0000000000000234.

Faas, M. M., and P. de Vos. 2020. Mitochondrial function in immune cells in health and disease. *Biochim. Biophys. Acta-Mol. Basis Dis.* doi:10.1016/j.bbadis.2020.165845.

Freeman, L. R., and J. N. Keller. 2012. Oxidative stress and cerebral endothelial cells: Regulation of the blood-brain-barrier and antioxidant based interventions. *Biochim. Biophys. Acta-Mol. Basis Dis.* doi:10.1016/j.bbadis.2011.12.009.

Galley, H. F. 2011. Oxidative stress and mitochondrial dysfunction in sepsis. *Br. J. Anaesth.* 107:57-64. doi:10.1093/bja/aer093.

Ginhoux, F., S. Lim, G. Hoeffel, D. Low, and T. Huber. 2013. Origin and differentiation of microglia. *Front. Cell. Neurosci.* 7:45. doi:10.3389/fncel.2013.00045.

Giridharan, V. V., F. Masud, F. Petronilho, F. Dal-Pizzol, and T. Barichello. 2019. Infection-induced systemic inflammation is a potential driver of Alzheimer's disease progression. *Front. Aging Neurosci.* doi:10.3389/fnagi.2019.00122.

Gofton, T. E., and G. B. Young. 2012. Sepsis-associated encephalopathy. *Nat. Rev. Neurol.* 8:557-66. doi:10.1038/nrneurol.2012.183.

Guerreiro M O, Petronilho F, Andrades M, Constantino L, et al. 2010. Plasma superoxide dismutase activity and mortality in septic patients [corrected]. *The Journal of trauma* 69: E102-6.

Heming, N., A. Mazeraud, F. Verdonk, F. A. Bozza, F. Chrétien, and T. Sharshar. 2017. Neuroanatomy of sepsis-associated encephalopathy. Crit. Care. 21:65. doi:10.1186/s13054-017-1643-z.

Hosokawa, K., N. Gaspard, F. Su, M. Oddo, J. L. Vincent, and S. S. Taccone. 2014. Clinical neurophysiological assessment of sepsis-associated brain dysfunction: A systematic review. *Crit. Care.* 18. doi:10.1186/s13054-014-0674-y.

Iwashyna, T. J., E. W. Ely, D. M. Smith, and K. M. Langa. 2010a. Long-term cognitive impairment and functional disability among survivors of severe sepsis. *JAMA-J. Am. Med. Assoc.* 304:1787-1794. doi:10.1001/jama.2010.1553.

Iwashyna, T. J., E. W. Ely, D. M. Smith, K. M. Langa, J. AF, A. PD, N. DM, I. TJ, R. R, F. TR, L. KM, F. TR, A. DC, Y. S, W. BD, B. CM, F. TG, H. C, H. MS, C. L, H. RO, K. A, M. GS, Q. H, F. S, H. AR, W. KA, L. KM, L. KM, O. MB, B.-H. J, Z. K, Y. K, M. KM, Z.-G. K, J. JC, G. TD, S. S, S. T, C. LA, S. WD, S. WD, K. H-K, L. KM, M. ME, K. HK, S. CL, E. EW, M. S, B. CM, B. CM, C. KE, and P. BL. 2010b. Long-term Cognitive Impairment and Functional Disability Among Survivors of Severe Sepsis. JAMA. 304:1787. doi:10.1001/jama.2010.1553.

Jung, S., J. Aliberti, P. Graemmel, M. J. Sunshine, G. W. Kreutzberg, A. Sher, and D. R. Littman. 2000. Analysis of fractalkine receptor CX(3)CR1 function by targeted deletion and green fluorescent protein reporter gene insertion. *Mol. Cell. Biol.* 20:4106-14.

de Kloet E R, Joels M, Holsboer F. 2005. Stress and the brain: from adaptation to disease. *Nature reviews Neuroscience* 6: 463-75.

Kraft, B. D., L. Chen, H. B. Suliman, C. A. Piantadosi, and K. E. Welty-Wolf. 2019. Peripheral Blood Mononuclear Cells Demonstrate Mitochondrial Damage Clearance during Sepsis. *Crit. Care Med.* doi:10.1097/CCM.0000000000003681.

Lauro, C., and C. Limatola. 2020. Metabolic Reprogramming of Microglia in the Regulation of the Innate Inflammatory Response. *Front. Immunol.* doi:10.3389/fimmu.2020.00493.

Leger, M., A. Quiedeville, V. Bouet, B. Haelewyn, M. Boulouard, P. Schumann-Bard, and T. Freret. 2013.

Object recognition test in mice. *Nat. Protoc.* 8:2531-2537. doi:10.1038/nprot.2013.155.

Liu, D., Y. Shan, L. Valluru, and F. Bao. 2013a. Mn (III) tetrakis (4-benzoic acid) porphyrin scavenges reactive species, reduces oxidative stress, and improves functional recovery after experimental spinal cord injury in rats: comparison with methylprednisolone. *BMC Neurosci.* 14:23. doi:10.1186/1471-2202-14-23.

Liu, D., Y. Shan, L. Valluru, and F. Bao. 2013b. Mn (III) tetrakis (4-benzoic acid) porphyrin scavenges reactive species, reduces oxidative stress, and improves functional recovery after experimental spinal cord injury in rats: Comparison with methylprednisolone. *BMC Neurosci.* doi:10.1186/1471-2202-14-23.

Manfredini, A., L. Constantino, M. C. Pinto, M. Michels, H. Burger, L. W. Kist, M. C. Silva, L. M. Gomes, D. Dominguini, A. Steckert, C. Simioni, M. Bogo, E. Streck, T. Barichello, J. De Quevedo, M. Singer, C. Ritter, and F. Dal-Pizzol. 2019. Mitochondrial dysfunction is associated with long-term cognitive impairment in an animal sepsis model. *Clin. Sci.* 133:1993-2004. doi:10.1042/CS20190351.

Mostel, Z., A. Perl, M. Marck, S. F. Mehdi, B. Lowell, S. Bathija, R. Santosh, V. A. Pavlov, S. S. Chavan, and J. Roth. 2019. Post-sepsis syndrome-A n evolving entity that afflicts survivors of sepsis. *Mol. Med.* 26. doi:10.1186/s10020-019-0132-z.

Neher, J. J., and C. Cunningham. 2019. Priming Microglia for Innate Immune Memory in the Brain. *Trends Immunol.* doi:10.1016/j.it.2019.02.001.

Neri, M., I. Riezzo, C. Pomara, S. Schiavone, and E. Turillazzi. 2016. Oxidative-Nitrosative Stress and Myocardial Dysfunctions in Sepsis: Evidence from the Literature and Postmortem Observations. *Mediators Inflamm.* doi:10.1155/2016/3423450.

Pandharipande, P. P., T. D. Girard, and E. W. Ely. 2014. Long-term cognitive impairment after critical illness. *N. Engl. J. Med.* 370:185-6. doi:10.1056/NEJMc1313886.

Perry, V. H., and C. Holmes. 2014. Microglial priming in neurodegenerative disease. *Nat. Rev. Neurol.* 10:217-224. doi:10.1038/nrneurol.1.2014.38.

Pietrocola, F., L. Galluzzi, J. M. Bravo-San Pedro, F. Madeo, and G. Kroemer. 2015. Acetyl coenzyme A: A central metabolite and second messenger. *Cell Metab.* doi:10.1016/j.cmet.2015.05.014.

Prauchner, C. A. 2017. Oxidative stress in sepsis: Pathophysiological implications justifying antioxidant cotherapy. *Burns.* 43:471-485. doi:10.1016/j.burns.2016.09.023.

Prescott, H.C., and D.C. Angus. 2018. Enhancing recovery from sepsis: A review. *JAMA-J. Am. Med. Assoc.* 319:62-75. doi:10.1001/jama.2017.17687.

Prescott, H. C., M. W. Sjoding, K. M. Langa, T. J. Iwashyna, and D. F. Mcauley. 2018. Late mortality after acute hypoxic respiratory failure. *Thorax.* doi:10.1136/thoraxjnl-2017-210109.

ProCESS Investigators, D. M. Yealy, J. A. Kellum, D. T. Huang, A. E. Barnato, L. A. Weissfeld, F. Pike, T. Terndrup, H. E. Wang, P. C. Hou, F. LoVecchio, M. R. Filbin, N. I. Shapiro, and D. C. Angus. 2014. A randomized trial of protocol-based care for early septic shock. *N. Engl. J. Med.* 370:1683-93. doi:10.1056/NEJMoa1401602.

Rahmel, T., B. Marko, H. Nowak, L. Bergmann, P. Thon, K. Rump, S. Kreimendahl, J. Rassow, J. Peters, M. Singer, M. Adamzik, and B. Koos. 2020. Mitochondrial dysfunction in sepsis is associated with diminished intramitochondrial TFAM despite its increased cellular expression. *Sci. Rep.* 10:1-11. doi:10.1038/s41598-020-78195-4.

Ren, C., R. Q. Yao, H. Zhang, Y. W. Feng, and Y. M. Yao. 2020. Sepsis-associated encephalopathy: A vicious cycle of immunosuppression. *J. Neuroinflammation.* doi:10.1186/s12974-020-1701-3.

Rittirsch, D., M. S. Huber-Lang, M. A. Flierl, and P. A. Ward. 2009. Immunodesign of experimental sepsis by cecal ligation and puncture. *Nat. Protoc.* 4:31-6. doi:10.1038/nprot.2008.214.

Rocheteau, P., L. Chatre, D. Briand, M. Mebarki, G. Jouvion, J. Bardon, C. Crochemore, P. Serrani, P. P. Lecci, M. Latif, B. Matot, P. G. Carlier, N. Latronico, C. Huchet, A. Lafoux, T. Sharshar, M. Ricchetti, and F. Chrétien. 2015. Sepsis induces long-term metabolic and mitochondrial muscle stem cell dysfunction amenable by mesenchymal stem cell therapy. *Nat. Commun.* 6:10145. doi:10.1038/ncomms10145.

Rogers, D. C., E. M. Fisher, S. D. Brown, J. Peters, A. J. Hunter, and J. E. Martin. 1997. Behavioral and functional analysis of mouse phenotype: SHIRPA, a proposed protocol for comprehensive phenotype assessment. *Mamm. Genome.* 8:711-3.

Rudd, K. E., S. C. Johnson, K. M. Agesa, K. A. Shackelford, D. Tsoi, D. R. Kievlan, D. V. Colombara, K. S. Ikuta, N. Kissoon, S. Finfer, C. Fleischmann-Struzek, F. R. Machado, K. K. Reinhart, K. Rowan, C. W. Seymour, R. S. Watson, T. E. West, F. Marinho, S. I. Hay, R. Lozano, A. D. Lopez, D. C. Angus, C. J. L. Murray, and M. Naghavi. 2020. Global, regional, and national sepsis incidence and mortality, 1990-2017: analysis for the Global Burden of Disease Study. *Lancet.* 395:200-211. doi:10.1016/50140-6736(19)32989-7.

Schaafsma, W., X. Zhang, K. C. van Zomeren, S. Jacobs, P. B. Georgieva, S. A. Wolf, H. Kettenmann, H. Janova, N. Saiepour, U. K. Hanisch, P. Meerlo, P. J. van den Eisen, N. Brouwer, H. W. G. M. Boddeke, and B. J. L. Eggen. 2015. Long-lasting pro-inflammatory suppression of microglia by LPS-preconditioning is mediated by RelB-dependent epigenetic silencing. *Brain. Behav. Immun.* doi:10.1016/j.bbi.2015.03.013.

Schang, A.-L., J. Van Steenwinckel, D. Cheyenne, M. Alkmark, H. Hagberg, P. Gressens, and B. Fleiss. 2014. Failure of thyroid hormone treatment to prevent inflammation-induced white matter injury in the immature brain. *Brain. Behav. Immun.* 37:95-102. doi:10.1016/j.bbi.2013.11.005.

Schmittgen, T. D., E. J. Lee, J. Jiang, A. Sarkar, L. Yang, T. S. Elton, and C. Chen. 2008. Real-time PCR quantification of precursor and mature microRNA. *Methods.* 44:31-8. doi:10.1016/j.ymeth.2007.09.006.

Semmler, A., C. Frisch, T. Debeir, M. Ramanathan, T. Okulla, T. Klockgether, and M. T. Heneka. 2007. Long-term cognitive impairment, neuronal loss and reduced cortical cholinergic innervation after recovery from sepsis in a rodent model. *Exp. Neurol.* 204:733-40. doi:10.1016/j.expneurol.2007.01.003.

Sharshar, T., F. Gray, G. Lorin de la Grandmaison, N. S. Hopkinson, E. Ross, A. Dorandeu, D. Orlikowski, J.-C. Raphael, P. Gajdos, and D. Annane. 2003. Apoptosis of neurons in cardiovascular autonomic centres triggered by inducible nitric oxide synthase after death from septic shock. *Lancet* (London, England). 362:1799-805.

Sharshar, T., R. Porcher, S. Siami, B. Rohaut, J. Bailly-Salin, N. S. Hopkinson, B. Clair, C. Guidoux, E. lacobone, R. Sonneville, A. Polito, J. Aboab, S. Gaudry, O. Morla, G. Amouyal, J. Azuar, J. Allary, A. Vieillard-Baron, M. Wolff, A. Cariou, D. Annane, and Paris-Ouest Study Group on Neurological Effect of Sedation (POSGNES). 2011. Brainstem responses can predict death and delirium in sedated patients in intensive care unit. *Crit. Care Med.* 39:1960-7. doi:10.1097/CCM.0b013e31821 b843b.

Sies, H., and D. P. Jones. 2020. Reactive oxygen species (ROS) as pleiotropic physiological signalling agents. *Nat. Rev. Mol. Cell Biol.* doi:10.1038/s41580-020-0230-3.

da Silva, F. P., and M. C. C. Machado. 2017. Septic shock and the aging process: A molecular comparison. *Front. Immunol.* doi:10.3389/fimmu.2017.01389.

Singer, M., C. S. Deutschman, C. W. Seymour, M. Shankar-Hari, D. Annane, M. Bauer, R. Bellomo, G. R. Bernard, J.-D. Chiche, C. M. Coopersmith, R. S. Hotchkiss, M. M. Levy, J. C. Marshall, G. S. Martin, S. M. Opal, G. D. Rubenfeld, T. van der Poll, J.-L. Vincent, and D. C. Angus. 2016. The Third International Consensus Definitions for Sepsis and Septic Shock (Sepsis-3). *JAMA*. 315:801-10. doi:10.1001/jama.2016.0287.

Uttara B, Singh A V, Zamboni P, Mahajan R T. 2009. Oxidative stress and neurodegenerative diseases: a review of upstream and downstream antioxidant therapeutic options. *Current neuropharmacology* 7: 65-74.

van der Slikke, E. C., A. Y. An, R. E. W. Hancock, and H. R. Bouma. 2020. Exploring the pathophysiology of post-sepsis syndrome to identify therapeutic opportunities. *EBioMedicine.* doi:10.1016/j.ebiom.2020.103044.

Staples, E., R. J. M. Ingram, J. C. Atherton, and K. Robinson. 2013. Optimising the quantification of cytokines present at low concentrations in small human mucosal tissue samples using Luminex assays. *J. Immunol. Methods*. 394:1-9. doi:10.1016/j.jim.2013.04.009.

Sun, A., G. Netzer, D. S. Small, A. Hanish, B. D. Fuchs, D. F. Gaieski, and M. E. Mikkelsen. 2016. Association between Index Hospitalization and Hospital Readmission in Sepsis Survivors. *Crit. Care Med.* doi:10.1097/CCM .0000000000001464.

Suresh, M. V., B. Yu, S. Lakshminrusimha, D. Machado-Aranda, N. Talarico, L. Zeng, B. A. Davidson, S. Pennathur, and K. Raghavendran. 2013. The protective role of MnTBAP in oxidant-mediated injury and inflammation in a rat model of lung contusion. *Surg.* (United States). doi:10.1016/j.surg.2013.05.023.

Verdonk, F., P. Roux, P. Flamant, L. Fiette, F. A. Bozza, S. Simard, M. Lemaire, B. Plaud, S. L. Shorte, T. Sharshar, F. Chrétien, and A. Danckaert. 2016a. Phenotypic clustering: a novel method for microglial morphology analysis. *J. Neuroinflammation.* 13:153. doi:10.1186/s12974-016-0614-7.

Verdonk, F., P. Roux, P. Flamant, L. Fiette, F. A. Bozza, S. Simard, M. Lemaire, B. Plaud, S. L. Shorte, T. Sharshar, F. Chrétien, and A. Danckaert. 2016b. Phenotypic clustering: a novel method for microglial morphology analysis. *J. Neuroinflammation.* 13:153. doi:10.1186/s12974-016-0614-7.

Vincent, J. L., G. Jones, S. David, E. Olariu, and K. K. Cadwell. 2019. Frequency and mortality of septic shock in Europe and North America: A systematic review and meta-analysis. *Crit. Care.* 23:1-11. doi:10.1186/s13054-019-2478-6.

Yan, C., Z. Ma, H. Ma, Q. Li, Q. Zhai, T. Jiang, Z. Zhang, and Q. Wang. 2020. Mitochondrial Transplantation Attenuates Brain Dysfunction in Sepsis by Driving Microglial M2 Polarization. *Mol. Neurobiol.* 57:3875-3890. doi:10.1007/s12035-020-01994-3.

Zaghloul, N., M. E. Addorisio, H. A. Silverman, H. L. Patel, S. I. Valdés-Ferrer, K. R. Ayasolla, K. R. Lehner, P. S. Olofsson, M. Nasim, C. N. Metz, P. Wang, M. Ahmed, S. S. Chavan, B. Diamond, K. J. Tracey, and V. A. Pavlov. 2017. Forebrain cholinergic dysfunction and systemic and brain inflammation in murine sepsis survivors. *Front. Immunol.* 8. doi:10.3389/fimmu.2017.01673.

Zhang, H., Y. W. Feng, and Y. M. Yao. 2018. Potential therapy strategy: Targeting mitochondrial dysfunction in sepsis. *Mil. Med. Res.* doi:10.1186/s40779-018-0187-0.

Zhou, Q., M. Einert, H. Schmitt, Z. Wang, F. Pankratz, C. B. Olivier, C. Bode, J. K. Liao, and M. Moser. 2016. MnTBAP increases BMPR-II expression in endothelial cells and attenuates vascular inflammation. *Vascul. Pharmacol.* doi:10.1016/j.vph.2016.07.001.

The invention claimed is:

1. A method for the treatment of sepsis-induced microglial cells alteration(s) in brain microglia comprising administering to a human subject diagnosed with sepsis-associated encephalopathy (SAE) an MnTBAP compound or Mn(III) substituted pyridylporphyrin (MnP) compound according to any one of the following formula:

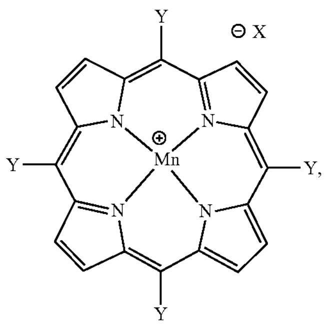

wherein

Y is

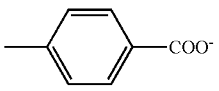 or 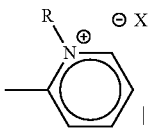, and

R is selected amongst ethyl (MnTE-2-Pyp5+), n-hexyl (MnTEHex-2-Pyp5+) and n-butyl-$OCH_2CH_2$— (MnTnBuOE-2-Pyp5+), and X is an anion, wherein the treatment reverses sepsis-induced microglial cells alteration(s) in brain microglia in the subject.

2. The method of claim 1, wherein said compound is administered to a subject diagnosed as a subject displaying symptom(s) corresponding to an acute change in total Sepsis-related Organ Failure Assessment score (SOFA score) equal or superior to 22 points subsequently to an infection.

3. The method of claim 1, wherein the subject suffers from behavioral impairment, cognitive dysfunction(s) or impairment, and brains disorder(s) including neuromyopathy.

4. The method of claim 3, wherein cognitive dysfunction(s) or impairment complication(s) is (are) alterations in memory, and/or alterations in attention, and/or alterations in concentration, and/or global loss of cognitive function.

5. The method of claim 1, wherein said compound induces a neuroprotective microglial phenotype.

6. The method of claim 1, wherein the antioxidant defence of the treated subject measured through SOD activity, is increased by the treatment.

7. The method of claim 1, wherein the said compound counteracts oxidative stress in the brain, thereby protecting the brain and/or cognitive function(s) of the treated subject.

8. The method of claim 1, wherein the subject is suffering from post-operative sepsis or neonatal sepsis or iatrogenic sepsis.

9. The method of claim 1, in an administration regime wherein the compound is first administered to a subject in need thereof between the moment of sepsis onset and 48 hours after the moment of sepsis onset, or between the moment of the diagnosis of the sepsis episode and 48 hours after the diagnosis of the sepsis episode, wherein the administration regime involves 1, 2, or 3, or 4, or 5 dose administration(s).

10. The method of claim 9, wherein the administration regime involves administration of 4 doses successively administered every 6 to 12 hours starting at sepsis onset or from the diagnosis of sepsis for the first administration.

11. The method of claim 1, wherein the compound is administered at a dose ranging from 5 to 15 mg/kg, calculated on the basis of the subject weight.

12. The method of claim 1, wherein the compound is administered through any one of the following routes: intranasal route, subcutaneous route, intradermal route, intravascular and intramuscular route.

13. The method of claim 1, wherein the compound is administered within a composition comprising said compound and at least one further pharmaceutical vehicle and/or adjuvant.

14. The method of claim 13, wherein the compound is administered at a dose of 10 mg/kg.

15. The method of claim 1, wherein the compound is administered at a dose ranging from 0.1 to 5 mg/kg, calculated on the basis of the subject weight.

16. The method of claim 15, wherein the compound is administered at a dose of 1 mg/kg.

17. The method of claim 1, wherein the treatment reverses sepsis-induced metabolic reprogramming of brain microglia.

* * * * *